US008778315B2

(12) United States Patent
Mehta et al.

(10) Patent No.: US 8,778,315 B2
(45) Date of Patent: Jul. 15, 2014

(54) MELANIN MODIFICATION COMPOSITIONS AND METHODS OF USE

(71) Applicant: Allergan, Inc., Irvine, CA (US)

(72) Inventors: Rahul C. Mehta, San Marcos, CA (US); Elizabeth Tsin Ho Makino, Carlsbad, CA (US); Sujatha D. Sonti, San Marcos, CA (US); John A. Garruto, Encinitas, CA (US)

(73) Assignee: Allergan, Inc., Irvine, CA (US)

( * ) Notice: Subject to any disclaimer, the term of this patent is extended or adjusted under 35 U.S.C. 154(b) by 34 days.

(21) Appl. No.: 13/777,552

(22) Filed: Feb. 26, 2013

(65) Prior Publication Data

US 2013/0177511 A1 Jul. 11, 2013

Related U.S. Application Data

(60) Division of application No. 13/532,289, filed on Jun. 25, 2012, which is a continuation of application No. 13/345,560, filed on Jan. 6, 2012, now Pat. No. 8,236,288.

(60) Provisional application No. 61/430,923, filed on Jan. 7, 2011.

(51) Int. Cl.
| | |
|---|---|
| A61K 8/00 | (2006.01) |
| A61K 8/18 | (2006.01) |
| A61Q 17/04 | (2006.01) |
| A61K 8/35 | (2006.01) |
| A61K 31/07 | (2006.01) |
| A61K 31/047 | (2006.01) |
| A61K 31/445 | (2006.01) |
| A61K 36/484 | (2006.01) |
| A61Q 19/02 | (2006.01) |
| A61K 8/97 | (2006.01) |
| A61K 8/33 | (2006.01) |
| A61K 31/375 | (2006.01) |
| A61K 31/122 | (2006.01) |
| A61K 8/67 | (2006.01) |
| A61K 8/49 | (2006.01) |

(52) U.S. Cl.
CPC .............. *A61K 8/33* (2013.01); *A61K 2800/92* (2013.01); *A61K 8/35* (2013.01); *A61K 31/07* (2013.01); *A61K 31/047* (2013.01); *A61K 31/445* (2013.01); *A61K 36/484* (2013.01); *A61Q 19/02* (2013.01); *A61K 8/97* (2013.01); *A61K 31/375* (2013.01); *A61K 31/122* (2013.01); *A61K 8/671* (2013.01); *A61K 8/4926* (2013.01)
USPC .......................................... 424/59; 424/400

(58) Field of Classification Search
USPC ............................................................ 424/59
See application file for complete search history.

(56) References Cited

U.S. PATENT DOCUMENTS

| | | |
|---|---|---|
| 3,598,122 A | 8/1971 | Zaffaroni |
| 3,598,123 A | 8/1971 | Zaffaroni |
| 3,710,795 A | 1/1973 | Higuchi et al. |
| 3,731,683 A | 5/1973 | Zaffaroni |
| 3,742,951 A | 7/1973 | Zaffaroni |
| 3,814,097 A | 6/1974 | Ganderton et al. |
| 3,845,138 A | 10/1974 | Dunlop et al. |
| 3,921,636 A | 11/1975 | Zaffaroni |
| 3,972,995 A | 8/1976 | Tsuk et al. |
| 3,993,072 A | 11/1976 | Zaffaroni |
| 3,993,073 A | 11/1976 | Zaffaroni |
| 3,996,934 A | 12/1976 | Zaffaroni |
| 4,126,695 A | 11/1978 | Razdan et al. |
| 4,147,770 A | 4/1979 | Sichak |
| 4,202,877 A | 5/1980 | Sato et al. |
| 4,290,974 A | 9/1981 | Boillon et al. |
| 4,391,603 A | 7/1983 | Rosenbaum et al. |
| 4,654,167 A | 3/1987 | Degner et al. |
| 4,668,712 A | 5/1987 | Hino et al. |
| 4,714,609 A | 12/1987 | Carden |
| 4,714,786 A | 12/1987 | Wuest et al. |
| 4,802,924 A | 2/1989 | Woznicki et al. |
| 4,857,328 A | 8/1989 | Trenzeluk |
| 4,992,445 A | 2/1991 | Lawter et al. |
| 4,997,850 A | 3/1991 | Kimura et al. |
| 5,001,139 A | 3/1991 | Lawter et al. |

(Continued)

FOREIGN PATENT DOCUMENTS

| | | |
|---|---|---|
| DE | 3214658 A1 | 11/1982 |
| EP | 0022229 A1 | 1/1981 |

(Continued)

OTHER PUBLICATIONS

Arnold et al. "Evaluation of chemotherapeutic agents in different mechanistic classes using a rat tracheal epithelial cell culture transformation assay," Cancer Res. 55:537, 1995.
Batt DG et al. "2-substituted-1-naphtols as potent 5-lipoxygenase inhibitors with topical antiinflammatory activity," J Med Chem 33:360-70, 1990.
Burton DE et al. "The mechanism of the antibacterial activity of phenols and salicylaldehydes. III. Substituted benzaldehydes," J Chem Soc 2458-60, 1964.

(Continued)

*Primary Examiner* — Mina Haghighatian
*Assistant Examiner* — Luke Karpinski
(74) *Attorney, Agent, or Firm* — Stephen Donovan

(57) ABSTRACT

A method for the modification of melanin distribution, and the composition thereof to modify melanin distribution are disclosed. A method for the reduction of melanin distribution, and the composition thereof to reduce melanin distribution are disclosed. A representative composition comprises 4-ethoxybenzaldehyde and one or more additional active agents as well as a pharmaceutically acceptable carrier or excipient. Carriers and excipients may be formulated for topical administration. Compositions may also be formulated for transdermal administration. The compositions may be used for the prevention and treatment of pigmentation disorders, by way of non-limited example, post-inflammatory hyperpigmentation and others. The compositions may be used for lightening skin.

7 Claims, 9 Drawing Sheets

(56) References Cited

U.S. PATENT DOCUMENTS

| | | |
|---|---|---|
| 5,023,252 A | 6/1991 | Hsieh |
| 5,100,654 A | 3/1992 | Pawelek et al. |
| 5,217,709 A | 6/1993 | Lagrange et al. |
| 5,508,310 A | 4/1996 | Rhodes |
| 5,601,838 A | 2/1997 | Hind |
| 5,614,179 A | 3/1997 | Murphy et al. |
| 5,626,852 A | 5/1997 | Suffis |
| 5,656,638 A | 8/1997 | Gaeta et al. |
| 5,668,182 A | 9/1997 | Abraham et al. |
| 5,733,535 A | 3/1998 | Hollingshead et al. |
| 5,747,537 A | 5/1998 | Gordon et al. |
| 5,760,085 A | 6/1998 | Beck et al. |
| 5,766,575 A | 6/1998 | Crotty et al. |
| 5,968,484 A | 10/1999 | Habeck et al. |
| 6,046,232 A | 4/2000 | Kelleher et al. |
| 6,086,903 A | 7/2000 | Trinh et al. |
| 6,126,930 A | 10/2000 | DuBois et al. |
| 6,146,650 A | 11/2000 | Redlinger |
| 6,204,229 B1 | 3/2001 | Hasegawa |
| 6,214,879 B1 | 4/2001 | Abraham |
| 6,248,763 B1 | 6/2001 | Scivoletto |
| 6,258,852 B1 | 7/2001 | Flitter et al. |
| 6,264,927 B1 | 7/2001 | Monahan |
| 6,284,234 B1 | 9/2001 | Niemiec et al. |
| 6,403,063 B1 | 6/2002 | Sawyer |
| 6,475,526 B1 | 11/2002 | Smith |
| 6,482,839 B1 | 11/2002 | Thornfeldt |
| 6,673,844 B2 | 1/2004 | Kumamoto et al. |
| 2003/0103916 A1 | 6/2003 | Imanaka et al. |
| 2003/0124157 A1 | 7/2003 | Engles et al. |
| 2003/0157154 A1 | 8/2003 | Fuller et al. |
| 2004/0254252 A1 | 12/2004 | Engles et al. |
| 2006/0257509 A1 | 11/2006 | Zimmerman et al. |
| 2008/0004354 A1 | 1/2008 | Engles et al. |
| 2009/0214628 A1 | 8/2009 | De Rijk |
| 2011/0217249 A1 | 9/2011 | Dreher |

FOREIGN PATENT DOCUMENTS

| | | |
|---|---|---|
| EP | 0044970 B1 | 2/1982 |
| EP | 0044976 | 2/1982 |
| EP | 0193257 | 9/1986 |
| EP | 0332175 A2 | 9/1989 |
| EP | 0395441 | 10/1990 |
| EP | 0635208 | 1/1995 |
| EP | 0914817 A1 | 5/1999 |
| EP | 0985408 | 3/2000 |
| GB | 1545954 | 4/1976 |
| GB | 2244645 A | 12/1991 |
| JP | 55-045656 | 3/1980 |
| JP | 55-045659 | 3/1980 |
| JP | 56-012310 | 2/1981 |
| JP | 60-067424 | 4/1985 |
| JP | 61-0257904 | 11/1986 |
| JP | 60-048929 | 2/1994 |
| JP | 06-329516 | 11/1994 |
| JP | 07-002640 | 1/1995 |
| JP | 07-242558 | 9/1995 |
| JP | 07-258042 | 10/1995 |
| JP | 07-258074 | 10/1995 |
| JP | 07-300412 | 11/1995 |
| JP | 01-106639 | 4/2001 |
| WO | 92-09276 | 6/1992 |
| WO | 97-47280 | 12/1997 |
| WO | 99-03446 | 1/1999 |
| WO | 99-06388 | 2/1999 |
| WO | 99-07336 | 2/1999 |
| WO | 99-22703 | 5/1999 |
| WO | 00-38653 | 7/2000 |
| WO | 00-74697 | 12/2000 |
| WO | 01-34106 A1 | 5/2001 |
| WO | 01-76626 | 10/2001 |
| WO | 02-083624 A1 | 10/2002 |
| WO | 03-000214 A1 | 1/2003 |
| WO | 2004-103233 | 12/2004 |
| WO | 2008-070368 | 6/2008 |

OTHER PUBLICATIONS

Chang et al. "Benzyloxybenzaldehyde analogues as novel adenyl cyclase activators," Bioorg Med Chem Lett 11:1871-1974, 2001.

Chen et al. "Effects of IH764-3 on chemotactic migration of neutrophils induced by rhIL-8," Chin J Pathophys 15:781, 1999. English Abstract.

PCT/US2012/020550 International Search Report and Written Opinion dated May 14, 2012.

Clerici et al. "In vitro immunomodulatory properties of Tucaresol in HIV infection," Clin Immunol 97:211, 2000.

Farah et al. "Pharmacologically active prenylpropanoids from *Senra incana*," Planta Medica 58:14-18, 1992.

Felton et al. "New class of broad spectrum antibacterials" TGA Cosmetic J 2:16-19, 1970.

Glenn "Anomalous biological effects of salicylates and prostaglandins," Agents Actions 9:257, 1979.

Inaoka et al. "Study on hair regrowth promoting substances from the potent herbs, especially *Polyporus umbellatus* F.," Tennen Yuki Kagobutsu Toronkai Koen Yoshishu 36:32, 1994. English Abstract.

Jimenez M et al. "Competitive inhibition of mushroom tyrosinase by 4-substitued benzaldehydes," J Agri Food Chem 49:4060-4063, 2001.

Kubo et al. "2-hydroxyl-4-methoxybenzaldehyde: a potent tyrosinase inhibitor in African medicinal plants," Planta Med 65:19, 1999.

Magae et al. "Antitumor protective property of an isoprenoid antibiotic, ascofuranone,"J Antibiotics 35:1547, 1982.

Nguyen et al. "Investigation on anti-acute inflammatory action of beta-aminoketone, a dervative of vaniline," Pharma J. 3:18, 2001. English translation.

Nomura M et al. "Studies on the use of cashew net shell oil. III. Synthesis of 6-[Z,ii7]-8,11,14-pentadecatrienyl] salicylic acid derivatives and their inhibition properties towards tyrosinase or hyaluronidase," Nippon Kagaku Kaishi 12:986-93, 1995.

Oikawa et al. "Oxidative DNA damage and apoptosis induced by metabolites of butylated hydroxytoluene," Biochem Pharmacol 56:361-370, 1998.

Opdyke DLJ "Monographs on fragrance raw materials p-ethoxybenzaldehyde," Food Cosm Toxicol 18:681, 1980.

Reddy et al. "Studies on anti-inflammatory activity of spice principles and dietary n-3 polyunsaturated fatty acids on carrageenan-induced inflammation in rats," Ann Nutr Metab 38:349-58, 1994.

Whitehouse et al. "Alternatives to aspirin, derived from biological sources," Agents Actions Suppl. 1:43-57, 1977.

Remington: The Science and Practice of Pharmacy, 20th Ed., pp. 836-844 and 917-918, 2000.

Van Den Worm et al. "Effects of methoxylation of apocyanin and analogs on the inhibition of reactive oxygen species production by stimulated human neutrophils," Eur J Pharmacol 433:225-230, 2001.

Inhibition of Prostaglandin F2 Alpha Levels

Assessment of Protection Factors from
Post-Inflammatory Hyperpigmentation Clinical Study Assessment of the Reduction in Hyperpigmentation Assessment of Skin Brightness Reduction in melanin Increase in Brightness of UV-Induced Pigmentation Significant Reduction in Hyperpigmentation Comparable Distribution of Results in Individual Subjects Better Subject Preference with Base + 0.5% 4-EB than with 4% Hydroquinone

MELANIN MODIFICATION COMPOSITIONS AND METHODS OF USE

CROSS-REFERENCE

This application is a divisional of U.S. patent application Ser. No. 13/532,289, filed Jun. 25, 2012, which is a continuation of U.S. patent application Ser. No. 13/345,560, filed Jan. 6, 2012 (now U.S. Pat. No. 8,236,288); which claims the benefit of U.S. Provisional Application No. 61/430,923, filed Jan. 7, 2011, all of which are incorporated herein by reference in their entirety.

BACKGROUND OF THE INVENTION

Melanin in humans is the primary determinant of skin color. Melanin in skin is produced by melanocytes in the epidermis in response to environmental triggers, such as increased sun exposure, or other physical or chemical perturbation. Melanin is also found in hair, the pigmented tissue underlying the iris of the eye, as well as the stria vascularis of the inner ear.

Environmental and/or physiological stress can cause disorders in melanin production. For example, post-inflammatory hyperpigmentation ("PIH") represents the sequelae of various cutaneous disorders, including infections, allergic reactions, mechanical injuries, reactions to medications, phototoxic eruptions, trauma (e.g., burns), inflammatory diseases (e.g., lichen planus, lupus erythematosus and atopic dermatitis), as well as reactions to devices, including electromagnetic devices such as ultrasound, radiofrequency, lasers, light-emitting diodes and visible light therapy, as well as microdermabrasion reactions. PIH occurs widely in the human population and can be the source of significant psychosocial distress for those affected with this disorder. PIH is a pathophysiologic response to cutaneous inflammation. Melanocytes can be stimulated by the inflammatory process to synthesize and secrete more melanin from melanocytes, or the number of melanocytes can increase in the epidermis, leading to hyperpigmentation of the skin. PIH can also occur when inflammation disrupts the basal cell layer, causing melanin pigment to be released and subsequently trapped by macrophages in the papillary dermis. Hyperpigmentation or hypermelanosis disorders due to environmental stressors, such as hormonal imbalance, can also affect melanin or pigmentation levels in the skin.

SUMMARY OF THE INVENTION

Provided herein are pharmaceutical and cosmetic compositions and methods of treating disorders relating to pigmentation or melanin levels. Provided herein are pharmaceutical and cosmetic compositions and methods of lightening skin. In some embodiments, the composition comprises a substituted benzaldehyde such as, for example 4-ethoxybenzaldehyde. In other embodiments, the composition comprises a substituted benzaldehyde and at least one additional active agent. Certain embodiments disclosed herein provide a method for modulating PGF2-alpha levels. Other embodiments provide a method for the treatment of pigmentation disorders comprising administration of the composition to an individual. The inventors of the present application identified for the first time that the compositions described herein may be use to treat post-inflammatory hyperpigmentation (PIH), where inflammation is not treated. It was also identified for the first time that the compositions described herein lighten skin.

In one aspect, provided herein is a method is presented for modifying melanin distribution in an individual, the method comprising administering to the individual in need thereof an effective amount of a composition comprising a substituted benzaldehyde and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a particular embodiment, the substituted benzaldehyde is 4-ethoxybenzaldehyde. In yet another embodiment, the substituted benzaldehyde is 2-ethoxybenzaldehyde.

In some embodiments, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In certain embodiments, the composition is topically administered to the skin of the individual. In other embodiments, the composition is transdermally administered to the skin of the individual.

In some embodiments, the compositions further comprise at least one additional active agent. In some embodiments, the compositions further comprise at least two additional active agents. In some embodiments, the compositions further comprise at least three additional active agents. An additional active agent may be, for example, an antioxidant, a sunscreen, a sunprotectant, a sunblock, a skin-lightening agent, an anti-inflammatory agent, an anti-acne agent or mixtures thereof. In other embodiments, the compositions further comprise one or more of a solvent, film former, preservative, viscosity increasing agent, fragrance, surfactant, chelating agent, humectant, or a combination thereof. In yet another embodiment, a composition comprises an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In yet another embodiment, a composition comprises niacinamide, butylene glycol, tetrahexyldecyl ascorbate, caprylic/capric triglycerides, polyacrylate-13, cetyl ethylhexanoate, phenoxyethanol, hexylresorcinol, ethyl linoleate, polyisobutene, 4-ethoxybenzaldehyde, squalene, tocopherol, potassium sorbate, retinol, polysorbate 20, ethylhexylglycerine, phytic acid, disodium EDTA, *dunaliella salina* extract and water.

In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g., undecylenoyl phenylalanine), phytic acid or combinations thereof.

In one aspect, provided herein is a composition comprising from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.5%.

In another aspect, provided herein is a composition comprising from about 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In yet another aspect, provided herein is a composition comprising about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Compositions described herein may be used to lighten skin as well as to treat hyperpigmentation or a hypermelanosis disorder. In one embodiment, the hyperpigmentation is post-inflammatory hyperpigmentation. Hyperpigmentation and hypermelanosis disorders may result from an environmental stressor, physiological stressor, or mechanical stressor.

Compositions described herein may reduce melanin distribution by about 10% to about 40% when applied to skin.

Compositions described herein may further comprise one or more additional active agents. An additional active agent may be, for example, an antioxidant, a sunscreen, a sunprotectant, a sunblock, a skin-lightening agent, an anti-inflammatory agent, an anti-acne agent or mixtures thereof.

In one embodiment, an antioxidant is selected from the group of vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, Tocopherol, *Dunaliella Salina* Extract or combinations thereof.

In one embodiment, a skin-lightening agent is selected from the group of hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

Pharmaceutically or cosmetically acceptable carriers for use in the present compositions are topical carriers. The topical carrier may be a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

The compositions described herein may also further comprise one or more of a solvent, film former, preservative, viscosity increasing agent, fragrance, surfactant, chelating agent, humectant, permeation enhancer, excipients, or a combination thereof.

In one embodiment, a composition comprises from about 0.1% to about 0.5% 4-ethoxybenzaldehyde, at least one additional active agent, and a pharmaceutically or cosmetically acceptable carrier. In other embodiment, a composition comprises from about 0.1% to about 0.5% 4-ethoxybenzaldehyde, at least two additional active agents, and a pharmaceutically or cosmetically acceptable carrier. In yet other embodiment, a composition comprises from about 0.1% to about 0.5% 4-ethoxybenzaldehyde, at least three additional active agents, and a pharmaceutically or cosmetically acceptable carrier. In yet other embodiment, a composition comprises from about 0.1% to about 0.5% 4-ethoxybenzaldehyde, at least four additional active agents, and a pharmaceutically or cosmetically acceptable carrier. In yet other embodiment, a composition comprises from about 0.1% to about 0.5% 4-ethoxybenzaldehyde, at least five additional active agents, and a pharmaceutically or cosmetically acceptable carrier. In yet other embodiment, a composition comprises from about 0.1% to about 0.5% 4-ethoxybenzaldehyde, at least six additional active agents, and a pharmaceutically or cosmetically acceptable carrier. In yet other embodiment, a composition comprises from about 0.1% to about 0.5% 4-ethoxybenzaldehyde, at least seven additional active agents, and a pharmaceutically or cosmetically acceptable carrier.

In one embodiment, a composition comprises about 0.5% 4-ethoxybenzaldehyde, at least one additional active agent, and a pharmaceutically or cosmetically acceptable carrier. In other embodiment, a composition comprises about 0.5% 4-ethoxybenzaldehyde, at least two additional active agents, and a pharmaceutically or cosmetically acceptable carrier. In yet other embodiment, a composition comprises about 0.5% 4-ethoxybenzaldehyde, at least three additional active agents, and a pharmaceutically or cosmetically acceptable carrier. In yet other embodiment, a composition comprises about 0.5% 4-ethoxybenzaldehyde, at least four additional active agents, and a pharmaceutically or cosmetically acceptable carrier. In yet other embodiment, a composition comprises about 0.5% 4-ethoxybenzaldehyde, at least five additional active agents, and a pharmaceutically or cosmetically acceptable carrier. In yet other embodiment, a composition comprises about 0.5% 4-ethoxybenzaldehyde, at least six additional active agents, and a pharmaceutically or cosmetically acceptable carrier. In yet other embodiment, a composition comprises about 0.5% 4-ethoxybenzaldehyde, at least seven additional active agents, and a pharmaceutically or cosmetically acceptable carrier.

In one embodiment, a composition comprises from about 0.1% to about 0.5% 4-ethoxybenzaldehyde, at least one skin lightening agent, at least one skin conditioning agent, at least one antioxidant, at least one occlusive, at least one emollient, at least one preservative, at least one viscosity increasing agent, at least one fragrance, at least one skin conditioning agent, at least one surfactant, at least one chlating agent, at least one humectant, and a pharmaceutically or cosmetically acceptable carrier.

On another embodiment, a composition comprises about 0.5% 4-ethoxybenzaldehyde, at least one skin lightening agent, at least one skin conditioning agent, at least one antioxidant, at least one occlusive, at least one emollient, at least one preservative, at least one viscosity increasing agent, at least one fragrance, at least one skin conditioning agent, at least one surfactant, at least one chlating agent, at least one humectant, and a pharmaceutically or cosmetically acceptable carrier.

In some embodiments, the substituted benzaldehyde composition modifies melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

Another aspect relates to a method of modifying melanin distribution in an individual, the method comprising contacting keratinocytes with an effective amount of a composition comprising a substituted benzaldehyde and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a particular embodiment, the substituted benzaldehyde is 4-ethoxybenzaldehyde. In yet another embodiment, the substituted benzaldehyde is 2-ethoxybenzaldehyde.

In some embodiments, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In certain embodiments, the composition is topically administered to the skin of the individual. In other embodiments, the composition is transdermally administered to the skin of the individual.

In some embodiments, the compositions further comprise at least one additional active agent. In particular embodiments, an additional active agent may be, for example, an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In some embodiments, the substituted benzaldehyde composition modifies melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In a further aspect, provided herein is a method of treating a melanin disorder in an individual comprising contacting keratinocytes with an effective amount of a composition comprising a substituted benzaldehyde and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In one embodiment, the cell is present in an individual. In another embodiment, the composition is topically administered to the skin of the individual. In yet another embodiment, the composition is transdermally administered to the skin of the individual.

In some embodiments, the compositions further comprise an additional active agent. In particular embodiments, the additional active agent is an antioxidant, a sunscreen, a sun-protectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropyl-cetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In a particular embodiment, the substituted benzaldehyde composition modifies melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In some embodiments, provided herein is a method of treating a hyperpigmentation skin disorder in an individual in need thereof, the method comprising administering to the skin of the individual an effective amount of a composition comprising a substituted benzaldehyde and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the hyperpigmentation skin disorder results from an environmental stressor, physiological stressor, or mechanical stressor. In a particular embodiment, the physiological stressor is a hormonal disorder. In yet another embodiment, the environmental stressor is excessive sun exposure or chemical exposure.

In some embodiments, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In some embodiments, the compositions further comprise an additional active agent. In particular embodiments, the additional active agent is an antioxidant, a sunscreen, a sun-protectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropyl-cetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In a particular embodiment, the substituted benzaldehyde composition modifies melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In some embodiments, provided herein are methods of treating hyperpigmentation or a hypermelanosis disorder in an individual, comprising administering to the individual in need thereof an effective amount of a composition comprising: from about 0.01% to about 2% substituted benzaldehyde and a pharmaceutically or cosmetically acceptable carrier.

In one embodiment, the method further comprises administering to the individual in need thereof an effective amount of about 0.01% to about 5.0% each of Retinol, Niacinamide, Tetrahexyldecyl Ascorbate, *Glycyrrhiza Glabra* (Licorice)

Root Extract, Hexyl Resorcinol, ethyl linoleate. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In another aspect, provided herein is a method of treating hyperpigmentation or a hypermelanosis disorder in an individual, comprising administering to the individual in need thereof an effective amount of a composition comprising: from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde is between about 0.1% to about 0.5%. In another embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.5%.

In another aspect, provided herein is a method of treating hyperpigmentation or a hypermelanosis disorder in an individual, comprising administering to the individual in need thereof an effective amount of a composition comprising: from about 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In another aspect, provided herein is a method of treating hyperpigmentation or a hypermelanosis disorder in an individual, comprising administering to the individual in need thereof an effective amount of a composition comprising: about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In some embodiments, the method reduces melanin distribution by about 10% to about 40%.

Application of the compositions in the methods described herein may be topical or transdermal administration to the skin of the individual.

In one embodiment, the pharmaceutically or cosmetically acceptable carrier is a topical carrier. Topical carriers include, for example, a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

In one embodiment, hyperpigmentation may result from an environmental stressor (e.g., excessive sun exposure or chemical exposure), physiological stressor (e.g., a hormonal disorder), or mechanical stressor.

Compositions described herein for use in such methods may further include one or more additional active agents. For example, an additional active agent may be an antioxidant, a sunscreen, a sunprotectant, a sunblock, a skin-lightening agent, an anti-inflammatory agent, an anti-acne agent or mixtures thereof. Compositions described herein for use in such methods may further include one or more of a solvent, film former, preservative, viscosity increasing agent, fragrance, surfactant, chelating agent, humectant, permeation enhancer, excipients, or a combination thereof.

Exemplary antioxidants include vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof.

Exemplary skin-lightening agents include hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

In another aspect, provided herein is a method of lightening skin in an individual, comprising administering to the individual in need thereof an effective amount of a composition comprising: from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.1% to about 0.5%.

In another aspect, provided herein is a method of lightening skin in an individual, comprising administering to the individual in need thereof an effective amount of a composition comprising: about 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In yet another aspect, provided herein is a method of lightening skin in an individual, comprising administering to the individual in need thereof an effective amount of a composition comprising: about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Also provided is a method of lightening skin in an individual, comprising administering to the individual in need thereof an effective amount of a composition comprising: from about 0.01% to about 2% substituted benzaldehyde and a pharmaceutically or cosmetically acceptable carrier.

In one embodiment, the method further comprises administering to the individual in need thereof an effective amount of about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In some embodiments, the methods decrease the level of pigmentation by about 5%, by about 10%, by about 20%, by about 30% or by about 40%.

The methods may be used to treat hyperpigmentation or a hypermelanosis disorder. In one embodiment, hyperpigmentation may result from an environmental stressor (e.g., excessive sun exposure or chemical exposure), physiological stressor (e.g., a hormonal disorder), or mechanical stressor.

In some embodiments, the method reduces melanin distribution by about 10% to about 40%.

Application of the compositions in the methods described herein may be topical or transdermal administration to the skin of the individual.

In one embodiment, the pharmaceutically or cosmetically acceptable carrier is a topical carrier. Topical carriers include, for example, a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

Compositions described herein for use in such methods may further include one or more additional active agents. For example, an additional active agent may be an antioxidant, a sunscreen, a sunprotectant, a sunblock, a skin-lightening agent, an anti-inflammatory agent, an anti-acne agent or mixtures thereof. Compositions described herein for use in such methods may further include one or more of a solvent, film former, preservative, viscosity increasing agent, fragrance, surfactant, chelating agent, humectant, permeation enhancer, excipient, or a combination thereof.

Exemplary antioxidants include vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, Tocopherol, *Dunaliella Salina* Extract or combinations thereof.

Exemplary skin-lightening agents include hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropyl-cetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

Provided herein are methods of modifying melanin distribution by modulating prostaglandin F2 alpha (PGF2 alpha) in a cell, comprising contacting said cell with a composition comprising from about 0.01% to about 2% substituted benzaldehyde and a pharmaceutically or cosmetically acceptable carrier.

In one embodiment, the method further comprises administering to the individual in need thereof an effective amount of about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate.

Provided is a method of modifying melanin distribution by modulating prostaglandin F2 alpha (PGF2 alpha) in skin cells in an individual, comprising administering to the individual in need thereof an effective amount of a composition comprising from about 0.01% to about 2% substituted benzaldehyde and a pharmaceutically or cosmetically acceptable carrier.

In one embodiment, the method further comprises administering to the individual in need thereof an effective amount of about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Provided is a method of modifying melanin distribution by modulating prostaglandin F2 alpha (PGF2 alpha) in a cell, comprising contacting said cell with a composition comprising from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the cells being treated are located in skin of an individual. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Provided is a method of modifying melanin distribution by modulating prostaglandin F2 alpha (PGF2 alpha) in skin cells in an individual, comprising administering to the individual in need thereof an effective amount of a composition comprising from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In one embodiment, the amount of substituted benzaldehyde is between about 0.1% to about 0.5%. In one embodiment, the amount of substituted benzaldehyde in the composition is about 0.5%.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.1% to about 0.5%. In one embodiment, the substituted benzaldehyde is 4-ethoxybenzaldehyde, which may be present in the composition in an amount of about 0.5%.

Also provided are methods of modifying melanin distribution by modulating prostaglandin F2 alpha (PGF2 alpha) in a cell, comprising contacting said cell with a composition comprising about 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the cells being treated are located in skin of an individual. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Provided herein is a method of modifying melanin distribution by modulating prostaglandin F2 alpha (PGF2 alpha) in a cell, comprising contacting said cell with a composition comprising about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the cells being treated are located in skin of an individual. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Also disclosed are methods of modifying melanin distribution by modulating prostaglandin F2 alpha (PGF2 alpha) in skin cells in an individual, comprising administering to the individual in need thereof an effective amount of a composition comprising about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the method reduces melanin distribution by about 10% to about 40%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Application of the compositions in the methods described herein may be topical or transdermal administration to the skin of the individual.

In one embodiment, the pharmaceutically or cosmetically acceptable carrier is a topical carrier. Topical carriers include, for example, a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

Compositions described herein for use in such methods may further include one or more additional active agents. For example, an additional active agent may be an antioxidant, a sunscreen, a sunprotectant, a sunblock, a skin-lightening agent, an anti-inflammatory agent, an anti-acne agent or mixtures thereof. Compositions described herein for use in such methods may further include one or more of a solvent, film former, preservative, viscosity increasing agent, fragrance, surfactant, chelating agent, humectant, permeation enhancer, excipient, or a combination thereof.

Exemplary antioxidants include vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, Tocopherol, *Dunaliella Salina* Extract or combinations thereof.

Exemplary skin-lightening agents include hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

In some embodiments, provided herein is a method of modifying melanin distribution in an individual, the method comprising administering to the individual in need thereof an effective amount of a composition comprising a substituted benzaldehyde, at least one additional active agent and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In some embodiments, the substituted benzaldehyde composition modifies melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In a further aspect, provided herein is a method of modifying melanin distribution in an individual, the method comprising contacting keratinocytes with an effective amount of a composition comprising a substituted benzaldehyde, at least one additional active agent and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In some embodiments, the substituted benzaldehyde composition modifies melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In another aspect, provided herein is a method of treating a melanin disorder in an individual, the method comprising contacting keratinocytes with an effective amount of a composition comprising a substituted benzaldehyde, at least one additional active agent and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the compositions further comprise a pharmaceutically or cosmetically acceptable carrier. In another embodiment, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In some embodiments, the cell is present on skin of an individual. In another embodiment, the composition is topically administered to the skin of the individual. In yet another embodiment, the composition is transdermally administered to the skin of the individual.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In some embodiments, the composition modifies melanin distribution by about 1%, about 2%, about 3%, about 4%, about 5%, about 6%, about 7%, about 8%, about 9%, about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In some embodiments, provided herein is a method of treating a hyperpigmentation skin disorder in an individual in need thereof, the method comprising administering to the skin of the individual an effective amount of a composition comprising a substituted benzaldehyde, at least one additional active agent and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the individual suffers from a hyperpigmentation disorder resulting from an environmental stressor, physiological stressor or mechanical stressor. In a particular embodiment, the physiological stressor is a hormonal disorder. In yet another embodiment, the environmental stressor is excessive sun exposure or chemical exposure.

In another embodiment, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), phytic acid or combinations thereof.

In some embodiments, the substituted benzaldehyde composition modifies melanin distribution by about 1%, about 2%, about 3%, about 4%, about 5%, about 6%, about 7%, about 8%, about 9%, about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In a further aspect, provided herein is a method of modulating the skin pigmentation of an individual, the method comprising administering to the skin of the individual an effective amount of a composition comprising a substituted benzaldehyde, at least one additional active agent and a pharmaceutically or cosmetically acceptable carrier, wherein the substituted benzaldehyde modulates PGF2-alpha in said individual. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the individual suffers from a hyperpigmentation disorder resulting from an environmental stressor, physiological stressor or mechanical stressor. In a particular embodiment, the physiological stressor is a hormonal disorder. In yet another embodiment, the environmental stressor is excessive sun exposure or chemical exposure.

In another embodiment, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), or phytic acid combinations thereof.

In some embodiments, the composition modifies melanin distribution by about 1%, about 2%, about 3%, about 4%, about 5%, about 6%, about 7%, about 8%, about 9%, about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

Another aspect provided herein relates to a method of modifying melanin distribution by modulating prostaglandin F2 alpha (PGF2 alpha) in a cell, the method comprising contacting said cell with a composition comprising a substituted benzaldehyde. In a particular embodiment, the composition modulates PGF2 alpha in a keratinocyte cell to modify melanin distribution. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the compositions further comprise a pharmaceutically or cosmetically acceptable carrier. In another embodiment, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In certain embodiments, the composition is topically administered to the skin of the individual. In other embodiments, the composition is transdermally administered to the skin of the individual.

In some embodiments, the compositions further comprise an additional active agent. In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), or phytic acid combinations thereof.

In some embodiments, the substituted benzaldehyde composition modifies melanin distribution by about 1%, about 2%, about 3%, about 4%, about 5%, about 6%, about 7%, about 8%, about 9%, about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In a further aspect, provided herein is a method of modifying melanin distribution by modulating prostaglandin F2 alpha (PGF2 alpha) in a cell, the method comprising contacting said cell with a composition comprising a substituted benzaldehyde and at least one additional active agent. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde.

In some embodiments, the compositions further comprise a pharmaceutically or cosmetically acceptable carrier. In another embodiment, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), or phytic acid combinations thereof.

In some embodiments, the composition modifies melanin distribution by about 1%, about 2%, about 3%, about 4%, about 5%, about 6%, about 7%, about 8%, about 9%, about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In a particular embodiment, the compositions disclosed herein modulate PGF2 alpha in a keratinocyte cell to modify melanin distribution. In some embodiments, the compositions disclosed herein modulate PGF2.

In a further aspect, provided herein are compositions comprising a combination of a substituted benzaldehyde, at least one additional active agent, and a pharmaceutically or cosmetically acceptable carrier. In some embodiments, the substituted benzaldehyde is 2-ethoxybenzaldehyde, 4-ethoxybenzaldehyde, 4-allyloxybenzaldehyde or 4-propoxybenzaldehyde. In a specific embodiment, the substituted benzaldehyde is 4-ethoxybenzaldehyde. In yet another embodiment, the substituted benzaldehyde is 2-ethoxybenzaldehyde. In some embodiments, the substituted benzaldehyde is a skin lightening agent.

In another embodiment, the pharmaceutically or cosmetically acceptable carrier is an oral or topical carrier. In other embodiments, the pharmaceutically or cosmetically acceptable topical carrier is a water-in-oil emulsion, cream, liquid, gel, oil, paste, ointment, suspension, foam, lotion, oil-in-water emulsion, water-in-oil-in-water emulsion, water-in-silicone emulsion, spray or serum carrier. In another embodiment, the composition is topically administered to the skin of the individual. In yet another embodiment, the composition is transdermally administered to the skin of the individual.

In another embodiment, an amount of the substituted benzaldehyde that is effective in reducing melanin levels in a subject is present in the composition. In some embodiments, the composition modifies melanin distribution by about 1%, about 2%, about 3%, about 4%, about 5%, about 6%, about 7%, about 8%, about 9%, about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In other embodiments, the composition reduces melanin distribution by about 10%, by about 15%, by about 20%, by about 25%, by about 30%, by about 35%, by about 40%, by about 45%, by about 50%, by about 55%, by about 60%, by about 65%, by about 70%, by about 75%, by about 80%, by about 85%, by about 90%, by about 95% or by about 100%. In another embodiment, the substituted benzaldehyde composition reduces melanin distribution by about 5% to about 50%. In yet another embodiment, the substituted benzaldehyde composition reduces melanin distribution by about 10% to about 40%.

In particular embodiments, the additional active agent is an antioxidant, a sunscreen, a sunprotectant, a sunblock, a skin-lightening agent, an anti-inflammatory agent, an anti-acne agent or mixtures thereof. In yet another embodiment, the compositions comprise an antioxidant selected from the group of niacinamide, vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, or combinations thereof. In another embodiment, the compositions comprise a skin-lightening agent selected from the group of hydroquinone, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, licorice extract (e.g., *Glycyrrhiza Glabra* (licorice) root extract), an alpha MSH antagonist (e.g. undecylenoyl phenylalanine), or phytic acid combinations thereof.

Another aspect provided herein relates to the use of the composition to treat a hyperpigmentation disorder. In some embodiments, the hyperpigmentation disorder is due to post-inflammatory hyperpigmentation disorder. In other embodiments, the post-inflammatory hyperpigmentation disorder is due to infections, allergic reactions, mechanical injuries, reaction to medications, phototoxic eruptions, trauma, or reaction to ultrasound, radiofrequency, lasers, light-emitting diodes, visible light therapy, microdermabrasion or chemical peel therapies.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the embodiments are set forth with particularity in the appended claims. A better understanding of the features and advantages of the present embodiments will be obtained by reference to the following detailed description that sets forth illustrative embodiments, in which the principles of the invention are utilized, and the accompanying drawings of which:

DETAILED DESCRIPTION OF THE INVENTION

Figure 1:
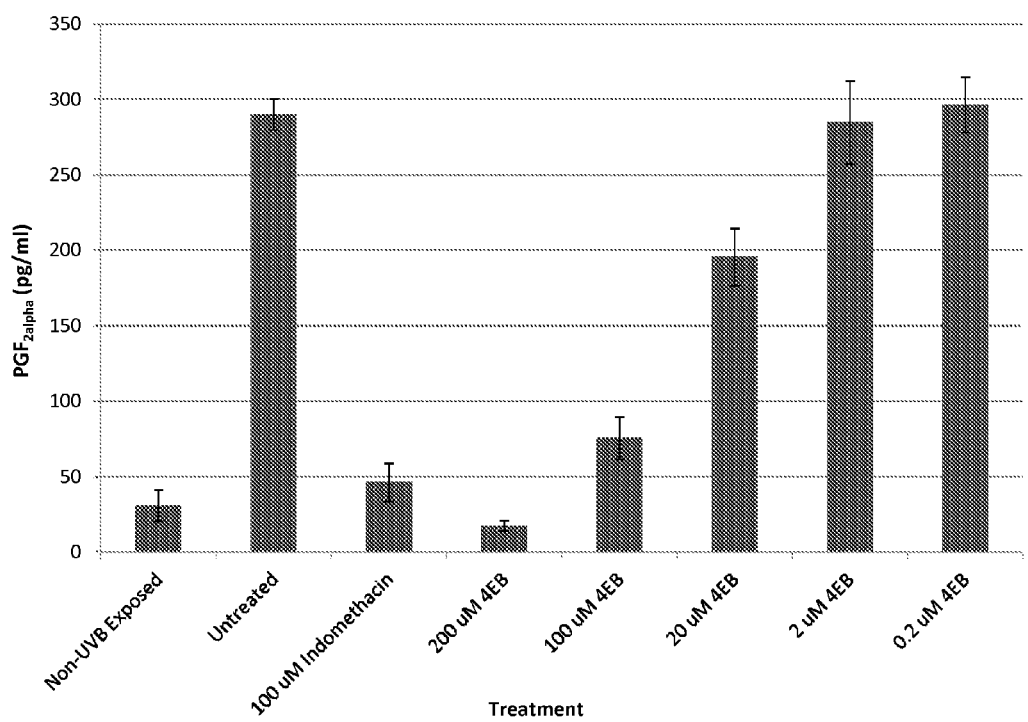
FIG. 1 is a graph that depicts 4-ethoxybenzaldehyde ("4EB") dose-dependent inhibition of PGF2 alpha in UVB-induced keratinocytes. Keratinocytes treated with indomethacin are used as a positive control.

The present disclosure relates to compositions comprising substituted benzaldehydes and optionally at least one additional active agent, and methods for using the compositions. The compositions disclosed may be used for the treatment of skin disorders, including the treatment of melanin or pigmentation disorders, including but not limited to hyperpigmentation or hypermelanosis disorders that affect melanin or pigmentation levels in the skin. Such disorders may be due to environmental stressors, such as excessive sun, or physiological stressors, such as hormonal imbalance. Such disorders include melasma, chloasma, post-inflammatory hyperpigmentation, acanthosis nigricans, pigmented purpura, urticaria, pityriasis, solar lentigines, vitiligo, birthmarks, port-wine stains, dark spots, age spots, freckles or sun spots. Other examples of uses of the disclosed compositions include hyper or hypopigmentation due to scarring, or exposure to environmental antigens or allergens, including phytodermatitis or phytophotodermatitis. In addition, the disclosed compositions may be used in conjunction with and/or for the treatment of skin disorders or trauma as a result of a mechanical injury or therapy, including but not limited to laser treatment, chemical peels, intense pulsed light, dermabrasion or cryotherapy.

The disclosed compositions may modify melanin and/or melanocyte distribution and/or levels for the treatment of melanin or pigmentation disorders. The disclosed compositions may modify melanin and/or melanocyte distribution and/or levels by about 1%, about 2%, about 3%, about 4%, about 5%, about 6%, by about 7%, about 7%, about 8%, about 9%, by about 10%, by about 12%, by about 15%, by about 20%, by about 25%, by about 30%, by about 35%, by about 35%, by about 40%, by about 45%, by about 50%, by about 55%, by about 60%, by about 70%, by about 80%, by about 90%, by about 100%, by about 125% or by about 150%. The disclosed compositions may decrease or increase melanin and/or melanocyte distribution and/or levels. For example, in the treatment of hyperpigmentation or hypermelanosis disorders, the disclosed compositions may decrease melanin and/or melanocyte distribution and/or levels by about 1%, about 2%, about 3%, about 4%, about 5%, about 6%, by about 7%, about 7%, about 8%, about 9%, by about 10%, by about 12%, by about 15%, by about 20%, by about 25%, by about 30%, by about 35%, by about 35%, by about 40%, by about 45%, by about 50%, by about 55%, by about 60%, by about 70%, by about 80%, by about 90% or by about 100%. In another embodiment, melanin distribution may be decreased by about 5% to about 50%. In yet another embodiment, melanin distribution may be decreased by about 10% to about 40%. The disclosed compositions may optionally modify or treat other cosmetic or therapeutic disorders, including dry skin, eczema or other cosmetic or dermatological disorders. The formulations disclosed herein may comprise a form for topical administration, including a lotion, emulsion, cream, gel, ointment, foam, liquid, paste or other topically administrable form. Alternatively, the formulations disclosed herein may comprise a form suitable for transdermal administration, including a transdermal patch, transdermal lotion, transdermal cream, transdermal gel, transdermal ointment, transdermal foam, transdermal liquid, transdermal paste or other transdermally-administrable form.

In some embodiments, an additional active agent(s) may be used in combination with the substituted benzaldehyde compositions disclosed. For example, other skin lightening agents may be used in combination with the substituted benzaldehydes, including hydroquinone, retinoids, corticosteroids, glycolic acid, other fruit acids, azelaic acid, vitamin C, licorice extract (e.g., *Glycyrrhiza Glabra* (licorice) root extract), an alpha MSH antagonist (e.g. undecylenoyl phenylalanine), phytic acid or mixtures thereof. In addition, skin or dermatological agents may also be used in combination with the substituted benzaldehyde compositions disclosed herein, including antioxidants, sunscreen and sunprotectants, emollients, barrier treatments, topical steroids, antibiotics, antimicrobials, acne medications, antiperspirants, deodorants, perfuming agents and other skin or dermatological agents or mixtures thereof. Alternatively, pre, simultaneous or subsequent dermatological treatments may also take place in combination with the compositions disclosed herein, including laser treatment, chemical peels, intense pulsed light, dermabrasion or cryotherapy.

In one aspect, provided herein is a composition comprising from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.5%.

In another aspect, provided herein is a comprising from 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In yet another aspect, provided herein is a comprising about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Compositions described herein may be used to lighten skin as well as to treat hyperpigmentation or a hypermelanosis disorder. In one embodiment, the hyperpigmentation is post-inflammatory hyperpigmentation. Hyperpigmentation and hypermelanosis disorders may result from an environmental stressor, physiological stressor, or mechanical stressor.

Compositions described herein may reduce melanin distribution by about 10% to about 40% when applied to skin.

Compositions described herein may further comprise one or more additional active agents. An additional active agent may be, for example, an antioxidant, a sunscreen, a sunprotectant, a sunblock, a skin-lightening agent, an anti-inflammatory agent, an anti-acne agent or mixtures thereof.

In one embodiment, an antioxidant is selected from the group of vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, Tocopherol, *Dunaliella Salina* Extract or combinations thereof.

In one embodiment, a skin-lightening agent is selected from the group of hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

Pharmaceutically or cosmetically acceptable carriers for use in the present compositions are topical carriers. The topical carrier may be a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

The compositions described herein may also further comprise one or more of a solvent, film former, preservative, viscosity increasing agent, fragrance, surfactant, chelating agent, humectant, permeation enhancer (skin penetrator), excipients, or a combination thereof.

In one embodiment, a composition comprises about 0.5% 4-ethoxybenzaldehyde, at least one additional active agent, and a pharmaceutically or cosmetically acceptable carrier. In other embodiment, a composition comprises about 0.5% 4-ethoxybenzaldehyde, at least two additional active agents, and a pharmaceutically or cosmetically acceptable carrier. In yet other embodiment, a composition comprises about 0.5% 4-ethoxybenzaldehyde, at least three additional active agents, and a pharmaceutically or cosmetically acceptable carrier. In yet other embodiment, a composition comprises about 0.5% 4-ethoxybenzaldehyde, at least four additional active agents, and a pharmaceutically or cosmetically acceptable carrier. In yet other embodiment, a composition comprises about 0.5% 4-ethoxybenzaldehyde, at least five additional active agents, and a pharmaceutically or cosmetically acceptable carrier. In yet other embodiment, a composition comprises about 0.5% 4-ethoxybenzaldehyde, at least six additional active agents, and a pharmaceutically or cosmetically acceptable carrier.

In another embodiment, a composition comprises from about 0.1% to about 0.5% 4-ethoxybenzaldehyde, at least one skin lightening agent, at least one skin conditioning agent, at least one antioxidant, at least one occlusive, at least one emollient, at least one preservative, at least one viscosity increasing agent, at least one fragrance, at least one skin conditioning agent, at least one surfactant, at least one chelating agent, at least one humectant, and a pharmaceutically or cosmetically acceptable carrier.

In another embodiment, a composition comprises about 0.5% 4-ethoxybenzaldehyde, at least one skin lightening agent, at least one skin conditioning agent, at least one antioxidant, at least one occlusive, at least one emollient, at least one preservative, at least one viscosity increasing agent, at least one fragrance, at least one skin conditioning agent, at least one surfactant, at least one chelating agent, at least one humectant, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In some embodiments, the combination compositions disclosed herein may act additively or synergistically. In some embodiments, a "synergistic effect" may be seen where the combination of the substituted benzaldehyde and additional active agent(s) results in an activity that is more than the effect of the two individual agents alone. In other embodiments, a "synergistic effect" may be seen where a combination of the substituted benzaldehyde and additional active agent(s) results in a modulation in melanin distribution, but no effect is seen when the agents are used individually. In yet other embodiments, a "synergistic effect" may allow a decrease in the amount of substituted benzaldehyde and/or additional active agent(s) used, thereby decreasing the incidence of adverse side effects, such as itching, pruritis, skin irritation or other adverse side effects.

As used in the specification and the appended claims, the singular forms "a", "an" and "the" include plural references unless the context clearly dictates otherwise. Thus for example, reference to "the method" includes one or more methods, and/or steps of the type described herein and/or which will become apparent to those persons skilled in the art upon reading this disclosure.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "acyl" refers to a radical formed by removal of a hydroxyl group from an organic acid and has the general formula —C(O)—X where X is hydrogen, substituted or unsubstituted alkyl, substituted or unsubstituted cycloalkyl, substituted or unsubstituted cycloheteroalkyl, substituted or unsubstituted aryl, substituted or unsubstituted arylalkyl, substituted or unsubstituted heteroalkyl, substituted or unsubstituted heteroaryl, substituted or unsubstituted heteroarylalkyl as defined herein. Representative examples include, but are not limited to, formyl, acetyl, cylcohexylcarbonyl, cyclohexylmethylcarbonyl, benzoyl, benzylcarbonyl and the like.

"Acyloxy" refers to the group or radical —OC(O)R23 where R23 is hydrogen, substituted or unsubstituted alkyl, substituted or unsubstituted aryl or substituted or unsubstituted cycloalkyl.

The term "alkyl" as used herein refers to saturated or unsaturated, straight- or branched-chain hydrocarbon radicals derived from a hydrocarbon moiety containing between one and twenty carbon atoms by removal of a single hydrogen atom. Alkyl groups as used herein may optionally include one or more further substituent groups. This term is exemplified by groups such as methyl, ethyl, n-propyl, isopropyl, n-butyl, iso-butyl, tert-butyl, n-hexyl, n-octyl, tert-octyl and the like, and may be substituted or unsubstituted. The term "lower alkyl" refers to alkyl groups having 1 to 6 carbon atoms. The term "alkyl" also includes "cycloalkyls" as defined below.

"Alkynyl" refers to acetylenically or alkynically unsaturated hydrocarbyl groups particularly having 2 to 11 carbon atoms and more particularly 2 to 6 carbon atoms which can be straight-chained or branched and having at least 1 and particularly from 1 to 2 sites of alkynyl unsaturation. Particular non-limiting examples of alkynyl groups include substituted or unsubstituted acetylenic, substituted or unsubstituted ethynyl (—C≡CH), substituted or unsubstituted propargyl (—CH2C≡CH), and the like.

The term "aminoalkyl" as used herein, refers to an amino substituted alkyl radical. This term is meant to include alkyl groups having an amino substituent at any position and wherein the alkyl group attaches the aminoalkyl group to the parent molecule. The alkyl and/or amino portions of the aminoalkyl group can be further substituted with substituent groups.

As used herein, the term "alkoxy" refers to a radical formed between an alkyl group and an oxygen atom wherein the oxygen atom is used to attach the alkoxy group to a parent molecule. Alkoxy groups as used herein may optionally include further substituent groups. Particular alkoxy groups include, by way of example, substituted or unsubstituted methoxy, substituted or unsubstituted ethoxy, substituted or unsubstituted n-propoxy, substituted or unsubstituted isopropoxy, substituted or unsubstituted n-butoxy, substituted or unsubstituted tert-butoxy, substituted or unsubstituted sec-butoxy, substituted or unsubstituted n-pentoxy, substituted or unsubstituted n-hexoxy, substituted or unsubstituted 1,2-dimethylbutoxy, and the like.

As used herein, the term "alkenyl" refers to a straight or branched hydrocarbon chain radical containing up to twenty four carbon atoms and having at least one carbon-carbon double bond. Alkenyl groups as used herein may optionally include one or more further substituent groups. Particular alkenyl groups include substituted or unsubstituted ethenyl (—CH=CH2), substituted or unsubstituted n-propenyl (—CH2CH=CH2), substituted or unsubstituted isopropenyl (—C(CH3)=CH2), substituted or unsubstituted vinyl and substituted vinyl, and the like.

As used herein, the term "aryl" refers to a mono- or polycyclic carbocyclic ring system radicals having one or more aromatic rings. Aryl groups as used herein may optionally include further substituent groups. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like, and may be substituted or unsubstituted. Particularly, an aryl group comprises from 6 to 14 carbon atoms.

"Alkaryl" refers to an aryl group, as defined above, substituted with one or more substituted or unsubstituted alkyl groups, as defined above.

"Aralkyl" or "arylalkyl" refers to an alkyl group, as defined above, substituted with one or more substituted or unsubstituted aryl groups, as defined above.

"Aryloxy" refers to substituted or unsubstituted —O-aryl groups wherein "aryl" is as defined above.

"Alkylamino" refers to the group alkyl-NR28R29, wherein each of R28 and R29 are independently selected from hydrogen and substituted or unsubstituted alkyl.

"Arylamino" refers to the group aryl-NR30R31, wherein each of R30 and R31 are independently selected from hydrogen, substituted or unsubstituted aryl and substituted or unsubstituted heteroaryl.

"Alkoxyamino" refers to a radical —N(H)OR32 where R32 represents a substituted or unsubstituted alkyl or substituted or unsubstituted cycloalkyl group as defined herein.

"Alkoxycarbonyl" refers to a substituted or unsubstituted radical —C(O)-alkoxy where alkoxy is as defined herein.

"Alkylarylamino" refers to a substituted or unsubstituted radical —NR33R34 where R33 represents an alkyl or cycloalkyl group and R34 is an aryl as defined herein.

"Alkylsulfonyl" refers to a substituted or unsubstituted radical —S(O)2R35 where R35 is an alkyl or cycloalkyl group as defined herein. Representative examples include, but are not limited to, methylsulfonyl, ethylsulfonyl, propylsulfonyl, butylsulfonyl and the like.

"Alkylsulfinyl" refers to a substituted or unsubstituted radical —S(O)R35 where R35 is an alkyl or cycloalkyl group as defined herein. Representative examples include, but are not limited to, methylsulfinyl, ethylsulfinyl, propylsulfinyl, butylsulfinyl and the like.

"Alkylthio" refers to a substituted or unsubstituted radical —SR35 where R35 is an alkyl or cycloalkyl group as defined herein that may be optionally substituted as defined herein. Representative examples include, but are not limited to, methylthio, ethylthio, propylthio, butylthio, and the like.

"Amino" refers to the radical —NH2.

"Substituted amino" includes those groups recited in the definition of "substituted" herein, and particularly refers to the group —N(R36)2 where each R36 is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —N(R36)2 is an amino group.

"Aminocarbonyl" refers to the group —C(O)NR37R37 where each R37 is independently hydrogen, substituted or unsubstituted alkyl, substituted or unsubstituted aryl and substituted or unsubstituted cycloalkyl, or where the R37 groups are joined to form an alkylene group.

"Aminocarbonylamino" refers to the group —NR38C(O)NR38R38 where each R38 is independently hydrogen, substituted or unsubstituted alkyl, substituted or unsubstituted aryl or substituted or unsubstituted cycloalkyl, or where two R groups are joined to form an alkylene group.

"Aminocarbonyloxy" refers to the group —OC(O)NR39R39 where each R39 is independently hydrogen, substituted or unsubstituted alkyl, substituted or unsubstituted aryl or substituted or unsubstituted cycloalkyl, or where the R groups are joined to form an alkylene group.

"Arylalkyloxy" refers to a substituted or unsubstituted —O-arylalkyl radical where arylalkyl is as defined herein.

"Arylamino" means a substituted or unsubstituted radical —NHR40 where R40 represents an aryl group as defined herein.

"Aryloxycarbonyl" refers to a substituted or unsubstituted radical —C(O)—O-aryl where aryl is as defined herein.

"Arylsulfonyl" refers to a r substituted or unsubstituted radical —S(O)2R41 where R41 is an aryl or heteroaryl group as defined herein.

"Azido" refers to the radical —N3.

"Bicycloaryl" refers to a monovalent aromatic hydrocarbon group derived by the removal of one hydrogen atom from a single carbon atom of a parent bicycloaromatic ring system. Typical bicycloaryl groups include, but are not limited to, groups derived from indane, indene, naphthalene, tetrahydronaphthalene, and the like, and may be substituted or unsubstituted. Particularly, an aryl group comprises from 8 to 11 carbon atoms.

"Bicycloheteroaryl" refers to a monovalent bicycloheteroaromatic group derived by the removal of one hydrogen atom from a single atom of a parent bicycloheteroaromatic ring system. Typical bicycloheteroaryl groups include, but are not limited to, groups derived from benzofuran, benzimidazole, benzindazole, benzdioxane, chromene, chromane, cinnoline, phthalazine, indole, indoline, indolizine, isobenzofuran, isochromene, isoindole, isoindoline, isoquinoline, benzothiazole, benzoxazole, naphthyridine, benzoxadiazole, pteridine, purine, benzopyran, benzpyrazine, pyridopyrimidine, quinazoline, quinoline, quinolizine, quinoxaline, benzomorphan, tetrahydroisoquinoline, tetrahydroquinoline, and the like, and may be substituted or unsubstituted. Preferably, the bicycloheteroaryl group is between 9-11 membered bicycloheteroaryl, with 5-10 membered heteroaryl being particularly preferred. Particular bicycloheteroaryl groups are those derived from benzothiophene, benzofuran, benzothiazole, indole, quinoline, isoquinoline, benzimidazole, benzoxazole and benzdioxane.

"Carbamoyl" refers to the radical —C(O)N(R42)2 where each R42 group is independently hydrogen, substituted or unsubstituted alkyl, substituted or unsubstituted cycloalkyl or substituted or unsubstituted aryl, as defined herein, which may be optionally substituted as defined herein.

"Carboxy" refers to the radical —C(O)OH.

"Carboxyamino" refers to the radical —N(H)C(O)OH.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like, and may be substituted or unsubstituted.

"Cycloalkoxy" refers to the group —OR43 where R43 is substituted or unsubstituted cycloalkyl. Such cycloalkoxy groups include, by way of example, substituted or unsubstituted cyclopentoxy, substituted or unsubstituted cyclohexoxy and the like.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as substituted or unsubstituted cyclohexenyl, substituted or unsubstituted cyclopentenyl, substituted or unsubstituted cyclopropenyl, and the like.

"Fused Cycloalkenyl" refers to a substituted or unsubstituted cycloalkenyl having two of its ring carbon atoms in common with a second aliphatic or aromatic ring and having its olefinic unsaturation located to impart aromaticity to the cycloalkenyl ring.

"Cyanato" refers to the radical —OCN.

"Cyano" refers to the radical —CN.

"Dialkylamino" means a radical —NR44R45 where R44 and R45 independently represent an alkyl, substituted alkyl, aryl, substituted aryl, cycloalkyl, substituted cycloalkyl, cycloheteroalkyl, substituted cycloheteroalkyl, heteroaryl, or substituted heteroaryl group as defined herein.

The terms "halo" and "halogen" as used herein refer to an atom selected from fluorine, chlorine, bromine, and iodine.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. cycloheteroalkyl, aryl, e.g. heteroaryl, cycloalkenyl, cycloheteroalkenyl, and the like having from 1 to 5, and especially from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is between 5-15 membered heteroaryl, with 5-10 membered heteroaryl being particularly preferred. Particular heteroaryl groups are those derived from thiophene, pyrrole, benzothiophene, benzofuran, indole, pyridine, quinoline, imidazole, oxazole and pyrazine.

"Substituted" refers to a group in which one or more hydrogen atoms are each independently replaced with the same or different substituent(s). Typical substituents include, but are not limited to, —X, —R46, —O—, =O, —OR46, —SR46, —S—, =S, —NR46R47, =NR46, —CX3, —CF3, —CN, —OCN, —SCN, —NO, —NO2, =N2, —N3, —S(O)2O—, —S(O)2OH, —S(O)2R46, —OS(O2)O—, —OS(O)2R46, —P(O)(O—)2, —P(O)(OR46)(O—), —OP(O)(OR46)(OR47), —C(O)R46, —C(S)R46, —C(O)OR46, —C(O)NR46R47, —C(O)O—, —C(S)OR46, —NR48C(O)NR46R47, —NR48C(S)NR46R47, —NR49C(NR48)NR46R47 and —C(NR48)NR46R47, where each X is independently a halogen; each R46, R47, R48 and R49 are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR50R51, —C(O)R50 or —S(O)2R50 or optionally R50 and R51 together with the atom to which they are both attached form a cycloheteroalkyl or substituted cycloheteroalkyl ring; and R50 and R51 are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Benzaldehyde" refers to an aryl group substituted with a formyl group or radical (i.e. —C(O)H). Examples of representative substituted benzaldehydes (Formula I) and the hemiacetal (Formula II) and acetal (Formula III) equivalents include the following:

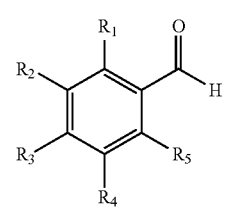

Formula I

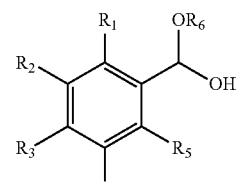

Formula II

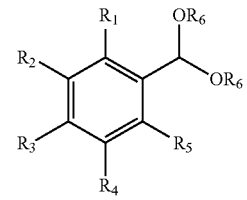

Formula III wherein each $R_1$, $R_2$, $R_3$, $R_4$, and $R_5$ is independently selected from hydrogen, halogen, alkyl, alkenyl, alkynyl, acyloxy, cycloalkyl, cycloheteroalkyl, alkoxy, alkoxyamino, alkoxycarbonyl, cycloalkoxy, cycloalkenyl, cyano, cyanato, aryl, arylalkyl, alkylaryl, aryloxy, heteroaryl, heteroaryloxy, amino, aminoalkyl, alkylarylamino, alkylamino, aminocarbonylamino, aminocarbonyloxy, arylamino, azido, bicycloaryl, carbamoyl, carboxy, carboxyamino, heteroarylamino, alkylsulfonyl, alkyl thio, and sulfone;

wherein at least one of $R_1$, $R_2$, $R_3$, $R_4$, or $R_5$ is not hydrogen; and each $R_6$ is independently alkyl.

"Pharmaceutically acceptable" means approved by a regulatory agency of the Federal or a state government or listed in the U.S. Pharmacopoeia or other generally recognized pharmacopoeia for use in animals, and more particularly in humans.

"Cosmetically acceptable" means suitable for cosmetic applications, including topical application of the compositions disclosed herein in the absence of significant adverse side effects upon application of the composition or compounds disclosed herein. Other applications include skin care applications, including but not limited to lotions, cream, cleansing creams or lotions, soaps and other cleansers, antiperspirant and/or deodorants, makeup products, such as face powders, foundations, rouge, eye shadow, mascara, eyeliner or lipstick, sun protection products, such as sunscreen or other UV-protective cosmetics, lotions or creams, hairdressing products, such as shampoo, rinses, or treatment setting agents. The phrases "pharmaceutically acceptable" and "cosmetically acceptable" are not meant to imply mutual exclusiveness in all applications. In some embodiments, a composition may be both "pharmaceutically acceptable" and "cosmetically acceptable," dependent upon the need and course of action of the compositions disclosed herein.

"Pharmaceutically acceptable salt" refers to a salt of a compound disclosed herein that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. In some embodiments, a "pharmaceutically acceptable salt" may also be used in conjunction with cosmeceutically-acceptable compositions.

The term "pharmaceutically acceptable cation" refers to a non toxic, acceptable cationic counter-ion of an acidic functional group. Such cations are exemplified by sodium, potassium, calcium, magnesium, ammonium, tetraalkylammonium cations, and the like. In some embodiments, a "pharmaceutically acceptable cation" may also be used in conjunction with cosmeceutically-acceptable compositions.

"Pharmaceutically acceptable vehicle" refers to a diluent, adjuvant, excipient or carrier with which a disclosed compound is administered. In some embodiments, a "pharmaceutically acceptable vehicle" may also be used in conjunction with cosmetically-acceptable compositions.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Prodrugs" refers to compounds, including derivatives of disclosed compounds, which have cleavable groups and become by solvolysis or under physiological conditions of compounds which are pharmaceutically active in vivo. Such examples include, but are not limited to, choline ester derivatives and the like, N-alkylmorpholine esters and the like.

"Solvate" refers to forms of the compound that are associated with a solvent, usually by a solvolysis reaction. Conventional solvents include water, ethanol, acetic acid and the like. The compounds disclosed herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Effective amount" means the amount of a compound that, when administered to a subject for treating a disease, cosmetic or dermatological condition, is sufficient to effect such treatment for the disease, cosmetic or dermatological condition. The "effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same. In a still further embodiment, "treating" or "treatment" refers to administration of the compound or compositions disclosed herein for cosmetic purposes.

Other derivatives of the disclosed compounds have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the disclosed compounds are preferred prodrugs. In some cases it is desirable to prepare double ester type prodrugs such as (acyloxy) alkyl esters or ((alkoxycarbonyl)oxy)alkylesters. Preferred are the C1 to C8 alkyl, C2-C8 alkenyl, aryl, C7-C12 substituted aryl, and C7-C12 arylalkyl esters of the disclosed compounds herein.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium (2H or D), carbon-13 (13C), nitrogen-15 (15N), or the like. It will be understood that, in a compound where such isotopic substitution is made, the following atoms, where present, may vary, so that for example, any hydrogen may be 2H/D, any carbon may be 13C, or any nitrogen may be 15N, and that the presence and placement of such atoms may be determined within the skill of the art. Likewise, the disclosed compounds may include the preparation of isotopic variants with radioisotopes, in the instance for example, where the resulting compounds may be used for drug and/or substrate tissue distribution studies. The radioactive isotopes tritium, i.e. 3H, and carbon-14, i.e. 14C, are particularly useful for this purpose in view of their ease of incorporation and ready means of detection. Further, compounds may be prepared that are substituted with positron emitting isotopes, such as 11C, 18F, 15O and 13N, and would be useful in Positron Emission Topography (PET) studies for examining substrate receptor occupancy.

All isotopic variants of the compounds provided herein, radioactive or not, are intended to be encompassed within the scope of the contemplated compounds.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The disclosed compounds may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

Melanin Disorders

As discussed above, melanin in humans is the primary determinant of skin color. Melanin pigments (eumelanin, pheomelanin and neuromelanin) are derivatives of the amino acid tyrosine, and production of melanin pigments is catalysed by the enzyme tyrosinase. Melanin is also found in hair, the pigmented tissue underlying the iris of the eye, as well as the stria vascularis of the inner ear. Melanin disorders can thus affect a variety of physiological systems, including the skin, hair, eye, inner ear, as well as neurological structures in the brain, where tissues with melanin include the medulla and zona reticularis of the adrenal gland, and pigment-bearing neurons within areas of the brainstem, such as the locus coeruleus and the substantia nigra.

Environmental and/or physiological stress can cause disorders in melanin production, as well as various genetic abnormalities. With regards to hypopigmentation disorders, there are approximately ten different types of oculocutaneous albinism, which is mostly an autosomal recessive disorder. Hypopigmentation occurs when pigment-producing cells (melanocytes) are either destroyed or inactive. Other hypopigmentation disorders include conditions due to skin damage (e.g. burn or ablative laser resurfacing) or due to autoimmune disease where the immune system attacks melanocytes, as in vitiligo. Vitiligo can also be caused by physical trauma or certain diseases, such as Addison's disease or diabetes.

Hyperpigmentation or hypermelanosis disorders result in an increase in melanin or melanocyte production and/or distribution. For example, post-inflammatory hyperpigmentation ("PIH") represents the sequelae of various cutaneous disorders, including infections, allergic reactions, mechanical injuries, reactions to medications, phototoxic eruptions, trauma (e.g. burns), as well as reactions to devices, including electromagnetic devices such as ultrasound, radiofrequency, lasers, light-emitting diodes and visible light therapy, as well as microdermabrasion reactions, shaving, chemical peels or other dermatological procedures. PIH occurs widely in the human population and can be the source of significant psychosocial distress for those affected with this disorder. PIH may occur as a pathophysiologic response to cutaneous inflammation. Melanocytes can be stimulated by the inflammatory process to synthesize and secrete more melanin from melanocytes, or the number of melanocytes can increase in the epidermis, leading to hyperpigmentation of the skin. PIH can also occur when inflammation succeeds in disrupting the basal cell layer, causing melanin pigment to be released and subsequently trapped by macrophages in the papillary dermis. PIH also occurs in instances where inflammation is untreated. One example of PIH as a result of inflammation is acne scarring. Hyperpigmentation or hypermelanosis disorders due to environmental stressors, such as hormonal imbalance, can also affect melanin or pigmentation levels in the skin. Other hyperpigmentation disorders include café au lait macules, melasma, choasma, age spots, drug-induced hyperpigmentation, Addison's disease, epheides (freckles), seborrheic keratosis, acanthosis nigricans, solar lentigines (sun spots), photoxic/photoallergic reaction, hemochromatosis and diabetic dermopathy.

Current treatment of hyperpigmentation disorders include topical lightening agents, laser/intense pulsed light, cryotherapy and chemical peels. However, for many individuals, cosmetic camouflaging of hyper or hypopigmentation cutaneous manifestations is the only viable alternative. Effective treatment of hypo and hyperpigmentation disorders, therefore, is needed.

The compositions disclosed herein seek to treat melanin disorders, including PIH and other hyperpigmentation disorders by modifying melanin distribution and/or production.

The compositions disclosed herein also seek to treat melanin disorders in conjunction with treatments and/or procedures that may cause hypermelanosis or hyperpigmentation disorders. Accordingly, the compositions disclosed herein may be used in conjunction with the treatment of skin disorders or trauma as a result of a mechanical injury or therapy, including but not limited to laser treatment, chemical peels, intense pulsed light, dermabrasion or cryotherapy.

Compounds

Disclosed herein are compositions comprising substituted benzaldehydes, at least one or a blend of pharmaceutically or cosmetically active agents, and a pharmaceutically or cosmetically acceptable carrier. In some embodiments, the substituted benzaldehydes disclosed herein are used in combination with at least one additional therapeutic agent.

In some embodiments, the composition comprises a substituted benzaldehyde of Formula I:

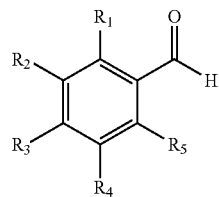

Formula I wherein each $R_1$, $R_2$, $R_3$, $R_4$, and $R_5$ is independently selected from hydrogen, halogen, alkyl, alkenyl, alkynyl, aryloxy, cycloalkyl, cycloheteroalkyl, alkoxy, alkoxyamino, alkoxycarbonyl, cycloalkoxy, cycloalkenyl, cyano, cyanato, aryl, arylalkyl, alkylaryl, aryloxy, heteroaryl, heteroaryloxy, amino, aminoalkyl, alkylarylamino, alkylamino, aminocarbonylamino, aminocarbonyloxy, arylamino, azido, bicycloaryl, carbamoyl, carboxy, carboxyamino, heteroarylamino, alkylsulfonyl, alkyl thio, and sulfone; and wherein at least one of $R_1$, $R_2$, $R_3$, $R_4$, or $R_5$ is not hydrogen.

In specific embodiments, R3 is ethoxy. In other embodiments, R1, R2, R4, and R5 are hydrogen.

Specific compounds of Formula I are shown below:

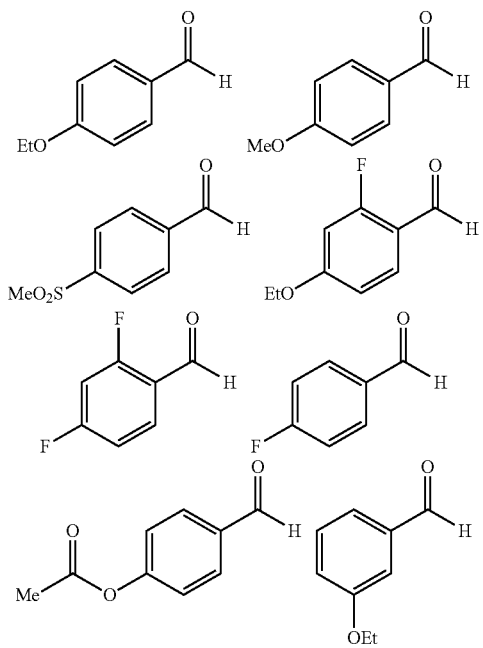

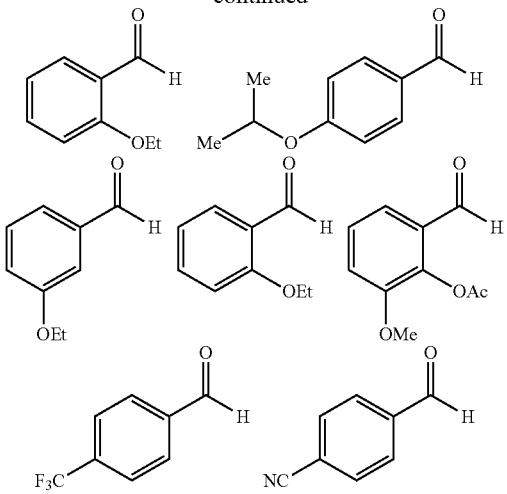

Non-limiting examples of substituted benzaldehydes include alkoxy-substituted benzaldehydes (e.g., 4-ethoxybenzaldehyde, 2-ethoxybenzaldehyde, 2-acetoxy-3-methoxybenzaldehye, 4-allyloxybenzaldehyde, 4-propoxybenzaldehyde, 4-butoxtbenzaldehyde, 2-fluoro-4-ethoxybenzaldehyde), amino-substituted benzaldehydes, alkyl-substituted benzaldehydes, aryl-substituted benzaldehydes, and sulfone-substituted benzaldehydes. In one embodiment, the substituted benzaldehyde is 4-ethoxybenzaldehyde, 2-ethoxybenzaldehyde, 4-allyloxybenzaldehyde and/or 4-propoxybenzaldehyde. In one particular embodiment, the substituted benzaldehyde is 4-ethoxybenzaldehyde.

In certain embodiments, the substituted benzaldehyde compounds include their acetal and hemiacetal equivalents (i.e., ~C(OR$_6$)(OH) and ~C(OR$_6$)$_2$ replaces the formyl group or ~C(O)H of the benzaldehyde, wherein R is an alkyl group). In some embodiments, the composition comprises the hemiacetal of Formula II:

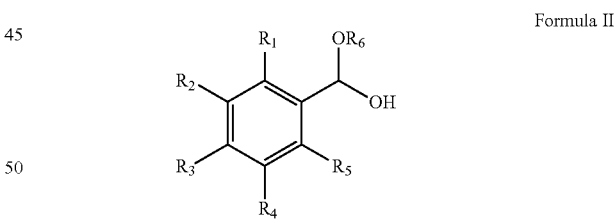

Formula II wherein each $R_1$, $R_2$, $R_3$, $R_4$, and $R_5$ is independently selected from hydrogen, halogen, alkyl, alkenyl, alkynyl, acyloxy, cycloalkyl, cycloheteroalkyl, alkoxy, alkoxyamino, alkoxycarbonyl, cycloalkoxy, cycloalkenyl, cyano, cyanato, aryl, arylalkyl, alkylaryl, aryloxy, heteroaryl, heteroaryloxy, amino, aminoalkyl, alkylarylamino, alkylamino, aminocarbonylamino, aminocarbonyloxy, arylamino, azido, bicycloaryl, carbamoyl, carboxy, carboxyamino, heteroarylamino, alkylsulfonyl, alkyl thio, and sulfone;

wherein at least one of $R_1$, $R_2$, $R_3$, $R_4$, or $R_5$ is not hydrogen; and each $R_6$ is independently alkyl.

In other embodiments, the composition comprises the acetal of Formula III:

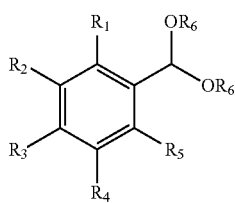

Formula III wherein each $R_1$, $R_2$, $R_3$, $R_4$, and $R_5$ is independently selected from hydrogen, halogen, alkyl, alkenyl, alkynyl, acyloxy, cycloalkyl, cyclohetероalkyl, alkoxy, alkoxyamino, alkoxycarbonyl, cycloalkoxy, cycloalkenyl, cyano, cyanato, aryl, arylalkyl, alkylaryl, aryloxy, heteroaryl, heteroaryloxy, amino, aminoalkyl, alkylarylamino, alkylamino, aminocarbonylamino, aminocarbonyloxy, arylamino, azido, bicycloaryl, carbamoyl, carboxy, carboxyamino, heteroarylamino, alkylsulfonyl, alkyl thio, and sulfone;

wherein at least one of $R_1$, $R_2$, $R_3$, $R_4$, or $R_5$ is not hydrogen; and each $R_6$ is independently alkyl.

Additional Active Agents

In one embodiment, the composition further comprises an active ingredient. Suitable active ingredients include, but are not limited to botanicals, nutraceuticals, cosmeceuticals, therapeutics, pharmaceuticals, antimicrobials, steroidal hormones, antidandruff agents, anti-acne components, sunscreens, sunblocks, sunprotectants, antibiotics, antivirals, antifungals, steroids, analgesics, antitumor drugs, investigational drugs, skin conditioning agents, or any compounds which would result in a complimentary or synergistic combination with the factors in the metabolized conditioned media or metabolized cell extract.

In a further embodiment, also included are topical formulations that comprise a composition for cosmetic or dermatological use, which composition comprises a cosmetically and/or dermatologically effective amount of the combination stated above, wherein the like acting agent is a cosmetically active agent. More particularly, the like-acting agent is a skin lightening or skin bleaching compound. In some embodiments, the skin lightening or skin bleaching compound is hydroquinone, kojic acid, ascorbic acid, magnesium ascorbyl phosphate or ascorbyl glucosamine, or mixtures thereof.

In another embodiment of the combination described above, the additional pharmaceutical or cosmetic agent is a skin care active agent. In some embodiments, the skin care active agent is an abrasive, an absorbent, an astringent, an aesthetic component, such as fragrances, pigments, colorings/colorants, essential oils, skin sensates, astringents and other aesthetic components, an antioxidant, a free-radical scavenging agent, a reducing agent, a sequestrant, a skin bleaching or lightening agent, a skin conditioning agent, for example humectants and emollients, a skin soothing agent, a skin healing agent, such as pathenol and derivatives, *aloe vera*, pantothenic acid, allantoin, bisbolol, dipotassium glycyrrhizinate, skin treating agents, vitamins and derivatives, such as a retinoid, or mixtures thereof. In some embodiments, the retinoid is retinol, retinal, retinol esters, retinyl propionate, retinoic acid, retinyl palmitate, or mixtures thereof.

In other embodiments, the composition comprises one or more antioxidant(s). Non-limiting examples of antioxidants are selected from the group consisting of niacinamide, vitamin E, Coenzyme Q10, idebenone, lycopene, green tea polyphenols, silybin, resveratrol, genistein, and pycnogenol.

Other embodiments include phenols and phenolic acids (guaiacol, hydroquinone, vanillin, gallic acids and their esters, protocatechuic acid, quinic acid, syringic acid, ellagic acid, salicylic acid, nordihydroguaiaretic acid (NDGA), eugenol); curcumins, tocopherols (including tocopherols (alpha, beta, gamma, delta) and their derivatives, such as tocopheryl-acylate (e.g., -acetate, -laurate, myristate, -palmitate, -oleate, -linoleate, etc., or an y other suitable tocopheryllipoate), tocopheryl-POE-succinate; *Dunaliella Salina* Extract; trolox and corresponding amide and thiocarboxamide analogues; ascorbic acid and its salts, isoascorbate, alkylascorbic acids, ascorbyl esters (e.g., 6-o-lauroyl, myristoyl, palmitoyl-, oleoyl, or linoleoyl-L-ascorbic acid, etc.). Also useful are oxidized compounds, such as sodium bisulphite, sodium metabisulphite, thiourea; chelating agents, such as EDTA (e.g., disodium EDTA), EGTA, desferral; transferrin, lactoferrin, ferritin, cearuloplasmin, haptoglobion, heamopexin, albumin, glucose, ubiquinol-10; enzymatic antioxidants, such as superoxide dismutase and metal complexes with a similar activity, including catalase, glutathione peroxidase, and less complex molecules, such as beta-carotene, bilirubin, uric acid; flavonoids (flavones, flavonols, flavonones, flavanonals, chacones, anthocyanins), N-acetylcystein, mesna, glutathione, thiohistidine derivatives, triazoles; tannines, cinnamic acid, hydroxycinnamatic acids and their esters (coumaric acids and esters, caffeic acid and their esters, ferulic acid, (iso-) chlorogenic acid, sinapic acid). Also included are extracts, including but not limited to plant extracts or cell extracts containing antioxidants, including grape seed extract, pomegranate extract, spice extracts (e.g., from clove, cinnamon, sage, rosemary, mace, oregano, allspice, nutmeg); oat flour extracts, such as avenanthramide 1 and 2; thioethers, dithioethers, sulphoxides, tetralkylthiuram disulphides and extracts from other plant derived material. Also included is carnosic acid, carnosol, carsolic acid; rosmarinic acid, rosmaridiphenol, gentisic acid, ferulic acid; phytic acid, steroid derivatives (e.g., U74006F); tryptophan metabolites (e.g., 3-hydroxykynurenine, 3-hydroxyanthranilic acid), and organochalcogenides.

In other embodiments, the composition comprises at least one additional skin lightening agent. Non-limiting examples of skin-lightening agents are selected from the group of hydroquinone, licorice extract (e.g., *Glycyrrhiza Glabra* (licorice) root extract), an alpha MSH antagonist (e.g. undecylenoyl phenylalanine), phytic acid, monobenzyl ether of hydroquinone, azelaic acid, kojic acid, mequinol, retinoids (e.g., tretinoin, adapalene), soy proteins, alpha-hydroxy acids (e.g., glycolic acid), trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, and tranexaminc acid.

In other embodiments, the composition comprises at least one botanical ingredient and/or extract. Non-limiting examples of botanical extracts are selected from the group arbutin, alpha-arbutin, deoxyarbutin, aloesin, flavonoids, isoflavones (e.g., 6,7,4'-trihydroxyisoflavone, glycitein, daidzein, genistein), flavonones (e.g., hesperidin, eriodictyol, and naringenin), flavonols, p-coumaric acid, gentisic acid, licorice extracts (e.g., glabridin, liquiritin, glabrene, isoliquiritigenin licuraside, isoliquiritin, licochalcone A), niacinamide, yeast derivatives, polyphenols, (e.g., proanthocyanidins, procyanidins, ellagic acid), ammonium glycyrrhizinate, icariin, piceid, salidroside, epigallocatechin-3-gallate, *glycyrrhiza* cinnamic aid, cinnamic acid, sophorcarpidine, *aloe vera* extract, *alaria esculenta* extract, alfalfa extract, algae extract, *althaea* extract, *angelica* extract, apple extract, *arnica* extract, ascorbyl palmitate, avocado oil, babassu palm tree fruit, balm mint extract, bamboo extract, bergamot oil, *betula* extract, bilberry, birch leaf extract, bisabolol, blackcurrant extract, black raspberry seed oil, bladderwrack extract, blue-green algae, blue malva extract, borage seed oil, *boswellia serrata, buddleja davidii* extract, buckthorn, buckwheat seed extract, burdock root extract, burdock, butcher's broom, *calendula, calendula* extract, *camellia* oil, capsaicin, carrageenan extract, carrot extract, cascara sagrada, castor oil, cayenne, cedarwood, chamomile, chamomile extract, chamomile oil, chaparral extract, chaste tree berry extract, chia seed oil, chickpea seed extract, *chlorella*, chrysanthellis, cinnamon bark, citrus extract, clover, clover blossom extract, clover extract, clover flower oil, cocoa extract, cocoa seed butter, codonopsis, *coleus forskohlli*, coriander, corn oil, cottonseed oil, couch grass, *crambe abyssinica* seed extract, cranberry protein, *crithmum maritimum* extract, cupuacu, cypress oil, dandelion, dandelion extract, dong quai, *Dunaliella Salina* extract, *Echinacea angustifolia purpurea, echium plantagineum*, elderberry, esculin, eucalyptus, evening primrose oil, fennel, *ferula foetida* root extract, flaxseed oil, fucoidan extract, *garcinia cambogia*, garlic, *geranium* extract, *geranium* oil, ginger, ginger root extract, *ginkgo biloba, ginseng, ginseng* extract, glucosamine, golden seal extract, gotu kola, grapefruit extract, grapeseed, grapeseed extract, grapeseed oil, green tea, green tea extract, guarana, guggul gum extract, *gymnesa sylvestre*, hazel oil, hawthorn, *holarrhena antidysenterica* extract, honeysuckle extract, hops extract, horse chestnut, horsetail extract, hybrid safflower oil, hydrolyzed soy protein, *imperata* cylindrical root extract, ivy leaf extract, jasmine oil, jojoba oil, juniper oil, kelp, kiwi seed fruit oil, kukui nut oil, lactic acid, lactospore, *laminaria digitata*, lavandin oil, lavender, lavender oil, lavender extract, L-carnitine, lecithin, lemon balm, lemon extract, lemon fruit extract, lemon oil, lemon verbena botanical plant essence, lemongrass extract, licorice extract (e.g., *Glycyrrhiza Glabra* (licorice) root extract), lime oil, linden extract, *lycium barbarum* fruit extract, lysate extract, lysine, maca root, *macadamia* oil, magnesium ascorbyl phosphate, *Mahonium aquifolium* (Oregon grape root) extract, maitake extract, mallow extract, maracuja, *marrubium vulgare* extract, marshmallow, manila oil, *matricaria* oil, meadowsweet. Melissa extract, menthol, milk thistle, moms alba root extract, mulberry extract (e.g., mulberroside F, gallic acid, quercetin, linoleic acid, palmitic acid), nettle extract, nettle root, nori sea lettuce, nutmeg oil, oat amino acids, oat extract, oat kernel meal, oligophycocorail (sea algae) extract, olive oil, olive leaf extract, squalene (e.g., olive squalen), orange blossom, orange oil, orange fruit extract, orange peel extract, orchid extract, *panax ginseng* extract, pansy extract, panthenol, papaya enzyme, passion fruit oil, *patchouli* oil, pea extract, pea protein, peach extract, peanut oil, pecan oil, pepper, peppermint, peppermint oil, *perilla* seed oil, pine leaf oil, pineapple enzyme, plankton extract, plantain extract, *polygonum fagopyrum* seed extract, pomegranate extract, pomegranate seed oil, *portulaca* extract, *psyllium*, pumpkin seed oil, raspberry extract, red clover, red clover extract, red marine algae extract, reishii, resveratrol, retinyl palmitate, rice bran oil, *rhodiola*, rhubarb, rice protein, *Rosa roxburghii* fruit extract, rose geranium botanical plant essence, rosehip extract, rosemary, *sccharomyces boulardii*, safflower oil, sage, sage extract, *sambucus Canadensis* extract, sandalwood, turmeric (*Curcuma longa* root) extract, *Bulbine frutescens* extract, *Bulbine frutescens* gel, and phytessence wakame (sea kelp).

In yet other embodiments, the composition comprises at least one sunscreen, sunprotectant or sunblock agent. "Sunscreen", "sunprotectant" or "sunblock" as used herein defines ultraviolet ray-blocking compounds exhibiting absorption or blockage within the wavelength region between about 290 and 420 nm. Such agents may be classified into five groups based upon their chemical structure: para-amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide and polymer particles such as those of polyethylene and polyamides. Specific suitable sunscreen agents include, for example: p-aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (amyl, phenyl, benzyl, menthyl, glyceryl, and dipropylene glycol esters); Cinnamic acid derivatives (methyl and benzyl esters, alpha-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol-3,3-disulfonic and of 2-naphthol-6,8-disulfonic acids); Dihydroxynaphthoic acid and its salts; o- and p-Hydroxybiphenyldisulfonates; Coumarin derivatives (7-hydroxy, 7-methyl, 3-phenylyll); Diazoles (2-acetyl-3-bromoindazole, phenyl benzoxazole, methyl naphthoxalole, various aryl benzothiazoles); Quinine salts (bisulfate, sulfate, chloride, oleate, and tannate); quinoline derivatives (8-hydroxyquinoline salts, 2-phenylquinoline); Hydroxy- or methoxy substituted benzophenones; Uric and vilouric acids; Tannic acid and its derivatives (e.g., hexaethylether); (Butyl carbityl) (6-propyl piperonyl)ether; Hydroquinone; Benzophenones (Oxybenzene, Sulisobenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyhldibenzoylmethane; Butylmethoxydibenzoylmethane; Etocrylene; and 4-isopropyl-di-benzoylmethane; titanium dioxide, iron oxide, zinc oxide, and mixtures thereof. Other cosmetically-acceptable sunscreens and concentrations (percent by weight of the total cosmetic sunscreen composition) include diethanolamine methoxycinnamate (10% or less), ethyl-[bis(hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less). Yet other cosmetically-acceptable sunscreens and concentrations (reported as a percentage by weight of the total cosmetic sunscreen composition, and referring to the final percentage of the sunscreen) include: aminobenzoic acid (also called para-aminobenzoic acid and PABA; 15% or less; a UVB absorbing organic sunscreen), avobenzone (also called butyl methoxy dibenzoylmethane; 3% or less, a UVA I absorbing organic sunscreen), cinoxate (also called 2-ethoxyethyl p-methoxycinnamate; 3% or less, a UVB absorbing organic sunscreen), dioxybenzone (also called benzophenone-8; 3% or less, a UVB and UVA II absorbing organic sunscreen), homosalate (15% or less, a UVB absorbing organic sunscreen), menthyl anthranilate (also called menthyl 2-aminobenzoate; 5% or less, a UVA II absorbing organic sunscreen), octocrylene (also called 2-ethylhexyl-2-cyano-3,3 diphenylacrylate; 10% or less, a UVB absorbing organic sunscreen), octyl methoxycinnamate (7.5% or less, a UVB absorbing organic sunscreen), octyl salicylate (also called 2-ethylhexyl salicylate; 5% or less, a UVB absorbing organic sunscreen), oxybenzone (also called benzophenone-3; 6% or less, a UVB and UVA II absorbing organic sunscreen), padimate 0 (also called octyl dimethyl PABA; 8% or less, a UVB absorbing organic sunscreen), phenylbenzimidazole sulfonic acid (water soluble; 4% or less, a UVB absorbing organic sunscreen), sulisobenzone (also called benzophenone-4; 10% or less, a UVB and UVA II absorbing organic sunscreen), titanium dioxide (25% or less, an inorganic physical blocker of UVA and UVB), trolamine salicylate (also called triethanolamine salicylate; 12% or less, a UVB absorbing organic sunscreen), and zinc oxide (25% or less, an inorganic physical blocker of UVA and UVB).

In still other embodiments, the composition comprises at least one anti-acne agent. Suitable anti-acne agents may include salicylic acid; 5-octanoyl salicylic acid; resorcinol; retinoids such as retinoic acid and its derivatives; sulfur-containing D and L amino acids other than cysteine; lipoic acid; antibiotics and antimicrobials such as benzoyl peroxide, octopirox, tetracycline, 2,4,4'-trichloro-2'-hydroxydiphenyl ether, 3,4,4'-trichlorobanilide, azelaic acid, phenoxyethanol, phenoxypropanol, phenoxisopropanol, ethyl acetate, clindamycin and melclocycline; flavonoids; and bile salts such as scymnol sulfate, deoxycholate and cholate.

In yet still other embodiments, the composition comprises at least one anti-inflammatory agent. Suitable anti-inflammatory agents include, but are not limited to, non-steroidal anti-inflammatory drugs such as salicylic acid, acetylsalicylic acid, methyl salicylate, aspirin, ibuprofen, naproxen, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; and other anti-inflammatory agents including, but not limited to, methotrexate, colchicine, allopurinol, probenecid, sulfinpyrazone and benzbromarone. Additional anti-inflammatories useful in topical applications include corticosteroids, such as, but not limited to, flurandrenolide, clobetasol propionate, halobetasol propionate, fluticasone propionate, betamethasone dipropionate, betamethasone benzoate, betamethasone valerate, desoximethasone, dexamethasone, diflorasone diacetate, mometasone furoate, amcinodine, halcinonide, fluocinonide, fluocinolone acetonide, desonide, triamcinolone acetonide, hydrocortisone, hydrocortisone acetate, fluoromethalone, prednisone, methylprednisolone, and predinicarbate.

In yet still other embodiments, the composition comprises at least one skin conditioning agents. Suitable skin conditioning agents include, but are not limited to, butylene glycol and ethylhexylglycerin.

In one embodiment, the composition contains the following additional active ingredients: Retinol, Niacinamide, Tetrahexyldecyl Ascorbate, Licorice root extract, Resorcinol, and ethyl linoleate. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Pharmaceutically or Cosmetically Suitable Carriers and Compositions

One aspect of the disclosed embodiments extends to a formulation that comprises a combination of a substituted benzaldehyde, additional active agents, and a carrier. In some embodiments, the active agent is selected from an antioxidant or a skin-lightening agent. In specific embodiments, the substituted benzaldehyde and active agents are administered in the form of a pharmaceutical or cosmetic composition. Such compositions can be prepared by procedures well known in the pharmaceutical and cosmetic arts. The compositions disclosed herein can contain a cosmetically or pharmacologically acceptable carrier. Such carriers are compatible with skin, nails, mucous membranes, tissues and/or hair, and can include any conventionally used cosmetic or pharmacological carrier. The compositions disclosed herein can be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (O/W or oil in water) or, conversely, (W/O or water in oil), microemulsions or alternatively microcapsules, microparticles or lipid vesicle dispersions of ionic and/or nonionic type. These compositions can be prepared according to conventional methods. Other than the agents disclosed, the amounts of the various constituents of the compositions are those conventionally used in the art. These compositions in particular constitute protection, treatment or care creams, milks, lotions, gels or foams for the face, for the hands, for the body and/or for the mucous membranes, or for cleansing the skin. The compositions can also consist of solid preparations constituting soaps or cleansing bars.

In some embodiments, the compositions disclosed herein are administered in an effective amount to treat a melanin disorder. Examples of routes of administration include, but are not limited to, oral, buccal, inhalation, intradermal, subcutaneous, transmucosal, transdermal, or topical administration. Topical administration may also involve the use of transdermal administration such as transdermal patches or iontophoresis devices. The construction and use of transdermal patches for the delivery of pharmaceutical agents is well known in the art. See, e.g., U.S. Pat. Nos. 5,023,252, 4,992, 445, and 5,001,139. Such patches can be constructed for continuous, pulsatile, or on demand delivery of pharmaceutical agents.

Pharmaceutically or cosmetically appropriate vehicles for such formulations include, for example, lower aliphatic alcohols, polyglycols (e.g., glycerol or polyethylene glycol), esters of fatty acids, oils, fats, silicones, and the like. Such preparations can also include preservatives (e.g., p-hydroxybenzoic acid esters) and/or antioxidants (e.g., ascorbic acid and tocopherol). See also Dermatological Formulations: Percutaneous absorption, Barry (Ed.), Marcel Dekker Incl, 1983.

In other embodiments, the composition further comprises at least one of water, a preservative, a surfactant, an emulsifier, a conditioner, an emollient, a wax, an oil, a polymer, a thickener (viscosity increasing agent), a fixative, a colorant, a humectant, a moisturizer, a stabilizer, a diluent, a solvent and a fragrance.

In one embodiment, the composition further comprises at least one preservative. Suitable preservatives include, but are not limited to, potassium sorbate, acids, alcohols, glycols, parabens, quaternary-nitrogen containing compounds, isothiazolinones, aldehyde-releasing compounds and halogenated compounds. Illustrative alcohols include phenoxyethanol, isopropyl alcohol, and benzyl alcohol; illustrative glycols include propylene, butylene and pentylene glycols; illustrative parabens include (also known as parahydroxybenzioc acids) methyl, propyl and butyl parabens; illustrative quaternary nitrogen containing compounds include benzalkonium chloride, Quartenium 15; illustrative isothiazoles include methylisothiazoline, methychlorolisothiazoline; illustrative aldehyde releasing agents include DMDM hydantion, imiadolidinyl urea and diazolidinyl urea; illustrative antioxidants include butylated hydroxytoluene, tocopherol and illustrative halogenated compounds include triclosan and chlorohexidene digluconate. Examples of preservatives useful for the purpose of the present disclosure can be found in Steinberg, D. "Frequency of Use of Preservatives 2007". Cosmet. Toilet. 117, 41-44 (2002) and, "Preservative Encyclopedia" Cosmet. Toilet. 117, 80-96 (2002). In addition, enzyme preservative systems such as those described in the article by Ciccognani D. Cosmetic Preservation Using Enzymes, in "Cosmetic and Drug Microbiology", Orth DS ed., Francis & Taylor, Boca Raton, Fla. (2006) can also be effective for use with the composition of the present disclosure.

In one embodiment, the composition further comprises at least one occlusive. Suitable occlusives include, but are not limited to, capryllic/capric triglycerides, and the like.

In one embodiment, the composition further comprises at least one emollient. Suitable emollients include, but are not limited to, cetyl ethylhexanoate, mineral oils, lanolin, petrolatum, capric/caprylic triglyceraldehydes, cholesterol, silicones such as dimeticone, cyclometicone, almond oil, jojoba oil, avocado oil, castor oil, sesame oil, sunflower oil, coconut oil and grape seed oil, cocoa butter, olive oil aloe extracts, fatty acids such as oleic and stearic, fatty alcohols such as cetyl and hexadecyl, diisopropyl adipate, hydroxybenzoate esters, benzoic acid esters of C9-15-alcohols, isononyl isononanoate, ethers such as polyoxypropylene butyl ethers and polyoxypropylene cetyl ethers, and C12-15-alkyl benzoates, and mixtures thereof.

In one embodiment, the composition further comprises at least one film fomers. Suitable film fomers include, but are not limited to, polyacrylate-13, Opadry II® or similar materials, e.g., such as those described in U.S. Pat. No. 4,802,924, incorporated herein by reference, may be used as a film former.

In yet other embodiments, the compound of Formula (I) is formulated for transdermal administration. Transdermal formulations may employ transdermal delivery devices and transdermal delivery patches and can be lipophilic emulsions or buffered, aqueous solutions, dissolved and/or dispersed in a polymer or an adhesive. In various embodiments, such patches are constructed for continuous, pulsatile, or on demand delivery of pharmaceutical agents. In additional embodiments, the transdermal delivery of the compounds of Formula (I) is accomplished by means of iontophoretic patches and the like. In certain embodiments, transdermal patches provide controlled delivery of the compounds of Formula (I). The rate of absorption may be slowed by using rate-controlling membranes or by trapping the compound within a polymer matrix or gel. Alternatively, absorption enhancers are used to increase absorption. Absorption enhancers or carriers include absorbable pharmaceutically acceptable solvents that assist passage through the skin. For example, in one embodiment, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Transdermal formulations described herein may be administered using a variety of devices which have been described in the art. For example, such devices include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. Transdermal drug delivery systems are topically administered medicaments and may be in the form of patches that deliver drugs for systemic effects at a predetermined and controlled rate. The components of transdermal devices include: (1) polymer matrix or matrices, (2) the drug, (3) permeation enhancers and (4) other excipients.

The polymer controls the release of the drug from the device. Useful polymers for transdermal devices include, but are not limited to Natural Polymers (e.g., Cellulose derivatives, Zein, Gelatin, Shellac, Waxes, Proteins, Gums and their derivatives, Natural rubber, Starch, etc.); Synthetic Elastomers (e.g., Polybutadieine, Hydrin rubber, Polysiloxane, Silicone rubber, Nitrile, Acrylonitrile, Butyl rubber, Styrenebutadieine rubber, Neoprene, etc.); and Synthetic Polymers (e.g., Polyvinyl alcohol, Polyvinyl chloride, Polyethylene, Polypropylene, Polyacrylate, Polyamide, Polyurea, Polyvinylpyrrolidone, Polymethylmethacrylate, Epoxy, etc.)

Solvents increase penetration possibly by enclosing the polar pathway and/or by fluidizing lipids. Examples include water alcohols (e.g., methanol and ethanol); alkyl methyl sulfoxides (e.g., dimethyl sulfoxide, alkyl homologs of methyl sulfoxide dimethyl acetamide and dimethyl formamide); pyrrolidones (e.g., 2 pyrrolidone, N-methyl, 2-purrolidone); laurocapram (Azone), miscellaneous solvents (e.g., propylene glycol, glycerol, silicone fluids, isopropyl palmitate).

Surfactants may enhance polar pathway transport, especially of hydrophilic drugs. The ability of a surfactant to alter penetration is a function of the polar head group and the hydrocarbon chain length. Anionic surfactants include, but are not limited to, Dioctyl sulphosuccinate, Sodium lauryl sulphate, and Decodecylmethyl sulphoxide. Nonionic surfactants include, but are not limited to, Pluronic F127, and Pluronic F68. Bile salts include, but are not limited to, Sodium ms taurocholate, Sodium deoxycholate, and Sodium tauroglycocholate. Others include, for example, Propylene glycol-oleic acid and 1,4-butane diol-linoleic acid, urea, N,N-dimethyl-m-toluamide, calcium thioglycolat, anticholinergic agents, eucalyptol, di-o-methyl-β-cyclodextrin and soyabean casein.

The fastening of all transdermal devices to the skin has so far been done by using a pressure sensitive adhesive which can be positioned on the face of the device or in the back of the device and extending peripherally. Adhesive systems should adhere to the skin aggressively, but be easily removed. They should also not leave an unwashable residue on the skin, and they should not irritate or sensitize the skin.

The face adhesive system should also be physically and chemically compatible with the drug, excipients and enhancers of the device of which it is a part. Permeation of drug should not be affected and the delivery of simple or blended permeation enhancers should not be affected.

Backing membranes are flexible and they provide a good bond to the drug reservoir, prevent drug from leaving the dosage form through the top, and accept printing. Backing membranes are impermeable substances that protect the product during use on the skin (e.g., metallic plastic laminate, plastic backing with absorbent pad and occlusive base plate (aluminum foil), adhesive foam pad (flexible polyurethane) with occlusive base plate (aluminum foil disc), etc.).

In addition, transdermal formulations can include additional components such as, but not limited to, gelling agents, creams and ointment bases, and the like. In some embodiments, the transdermal formulation further includes a woven or non-woven backing material to enhance absorption and prevent the removal of the transdermal formulation from the skin. In other embodiments, the transdermal formulations described herein maintain a saturated or supersaturated state to promote diffusion into the skin Compositions disclosed herein may be formulated in conventional manner using one or more pharmaceutically or cosmetically acceptable carriers comprising excipients and auxiliaries which facilitate processing of the substituted benzaldehydes and optional combination agents. Proper formulation is dependent upon the route of administration chosen and standard therapeutic practice. As used herein, the term "pharmaceutically or cosmetically acceptable carrier" means an inert, non toxic solid or liquid filler, diluent or encapsulating material, not reacting adversely with the active compound or with the subject. Suitable carriers are well known, and include water, saline, aqueous dextrose, sugar solutions, ethanol, glycols and oils, including those of petroleum, animal, vegetable, or synthetic origin, for example, peanut oil, soybean oil and mineral oil. In other embodiments, an agent or combination of agents of the instant embodiments can be formulated in an oleaginous hydrocarbon base, an anhydrous absorption base, a water-in-oil absorption base, an oil-in-water water-removable base and/or a water-soluble base. Examples of such carriers and excipients include, but are not limited to, humectants (e.g., urea), glycols (e.g., propylene glycol), alcohols (e.g., ethanol), fatty acids (e.g., oleic acid), surfactants (e.g., polysorbate-80, isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Compositions can also contain adjuvants common to the cosmetic and dermatological fields, such as hydrophilic or lipophilic gelling agents, hydrophilic or lipophilic active agents, preserving agents, antioxidants, solvents, fragrances, fillers, sunscreens, odor-absorbers and dyestuffs. The amounts of these various adjuvants are those conventionally used in the fields considered and, for example, are from about 0.01% to about 20% of the total weight of the composition. Depending on their nature, these adjuvants can be introduced into the fatty phase, into the aqueous phase and/or into the lipid vesicles.

The compositions may be in the form of tablets, capsules, skin patches, inhalers, eye drops, nose drops, ear drops, suppositories, creams, ointments, injectables, hydrogels and into any other appropriate formulation known to one of skill in the art. For oral administration the pharmaceutical compositions may take the form of, for example, tablets or capsules prepared by conventional means with acceptable excipients or carriers such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolae); or wetting agents (e.g., sodium lauryl sulphate). Tablets may be coated using methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with acceptable excipients or carriers such as suspending agents (e.g., sorbitol syrup cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Topical compositions disclosed herein may be in the form of a viscous liquid, solution, suspension, liposomal formulations, gel, jelly, cream, lotion, ointment, suppository, foam, aerosol spray aqueous or oily suspensions or solutions, emulsions, or emulsion ointments. Topical formulation for application to skin may include ointments, lotions, pastes, creams, gels, drops, suppositories, sprays, liquids, powders, shampoos, and transdermal patches. In one embodiment, a topical composition is provided which includes a topical carrier. For example, thickeners, diluents, emulsifiers, dispersing aids or binders may be used as needed. The topical carrier is selected so as to provide the composition in the desired form, e.g., as a liquid, lotion, cream, paste, gel, powder, or ointment, and may be comprised of a material of either naturally occurring or synthetic origin. Examples of suitable topical carriers for use herein include water, alcohols and other nontoxic organic solvents, glycerin, mineral oil, silicone, petroleum jelly, lanolin, fatty acids, vegetable oils, parabens, *aloe vera*, waxes, and the like.

Ointments and creams can, for example, be formulated with an aqueous or oily base with the addition of suitable thickening and/or gelling agents. Lotions can be formulated with an aqueous or oily base and will in general also containing one or more emulsifying agents, stabilizing agents, dispersing agents, suspending agents, thickening agents, or coloring agents.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

Thickeners (viscosity increasing agents) which can be used to form pharmaceutical compositions and dosage forms include, but are not limited to, polyacrylate-13, polyisobutene, Acetamide MEA; acrylamide/ethalkonium chloride acrylate copolymer; acrylamide/ethyltrimonium chloride acrylate/ethalkonium chloride acrylate copolymer; acrylamides copolymer; acrylamide/sodium acrylate copolymer; acrylamide/sodium acryloyldimethyltaurate copolymer; acrylates/acetoacetoxyethyl methacrylate copolymer; acrylates/beheneth-25 methacrylate copolymer; acrylates/ C10-C30 alkyl acrylate crosspolymer; acrylates/ceteth-20 itaconate copolymer; acrylates/ceteth-20 methacrylate copolymer; acrylates/laureth-25 methacrylate copolymer; acrylates/palmeth-25 acrylate copolymer; acrylates/palmeth-25 itaconate copolymer; acrylates/steareth-50 acrylate copolymer; acrylates/steareth-20 itaconate copolymer; acrylates/steareth-20 methacrylate copolymer; acrylates/stearyl methacrylate copolymer; acrylates/vinyl isodecanoate crosspolymer; acrylic acid/acrylonitrogens copolymer; adipic acid/methyl DEA crosspolymer; agar; agarose; *alcaligenes* polysaccharides; algin; alginic acid; almondamide DEA; almondamidopropyl betaine; aluminum/magnesium hydroxide stearate; ammonium acrylates/acrylonitrogens copolymer; ammonium acrylates copolymer; ammonium acryloyldimethyltaurate/vinyl formamide copolymer; ammonium acryloyldimethyltaurate/VP copolymer; ammonium alginate; ammonium chloride; ammonium polyacryloyldimethyl taurate; ammonium sulfate; amylopectin; apricotamide DEA; apricotamidopropyl betaine; arachidyl alcohol; arachidyl glycol; *arachis hypogaea* (peanut) flour; ascorbyl methylsilanol pectinate; *astragalus gummifer* gum; attapulgite; *avena sativa* (oat) kernel flour; avocadamide DEA; avocadamidopropyl betaine; azelamide MEA; babassuamide DEA; babassuamide MEA; babassuamidopropyl betaine; behenamide DEA; behenamide MEA; behenamidopropyl betaine; behenyl betaine; bentonite; butoxy chitosan; *caesalpinia spinosa* gum; calcium alginate; calcium carboxymethyl cellulose; calcium carrageenan; calcium chloride; calcium potassium carbomer; calcium starch octenylsuccinate; C20-40 alkyl stearate; canolamidopropyl betaine; capramide DEA; capryl/capramidopropyl betaine; carbomer; carboxybutyl chitosan; carboxymethyl cellulose acetate butyrate; carboxymethyl chitin; carboxymethyl chitosan; carboxymethyl dextran; carboxymethyl hydroxyethylcellulose; carboxymethyl hydroxypropyl guar; carnitine; cellulose acetate propionate carboxylate; cellulose gum; *ceratonia siliqua* gum; cetearyl alcohol; cetyl alcohol; cetyl babassuate; cetyl betaine; cetyl glycol; cetyl hydroxyethylcellulose; chimyl alcohol; cholesterol/HDI/pullulan copolymer; cholesteryl hexyl dicarbamate pullulan; *citrus aurantium dulcis* (orange) peel extract; cocamide DEA; cocamide MEA; cocamide MIPA; cocamidoethyl betaine; cocamidopropyl betaine; cocamidopropyl hydroxysultaine; cocobetaine; coco-hydroxysultaine; coconut alcohol; coco/oleamidopropyl betaine; coco-Sultaine; cocoyl sarcosinamide DEA; cornamide/cocamide DEA; cornamide DEA; croscarmellose; crosslinked *bacillus*/glucose/sodium glutamate ferment; *cyamopsis tetragonoloba* (guar) gum; decyl alcohol; decyl betaine; dehydroxanthan gum; dextrin; dibenzylidene sorbitol; diethanolaminooleamide DEA; diglycol/CHDM/ isophthalates/SIP copolymer; dihydroabietyl behenate; dihydrogenated tallow benzylmonium hectorite; dihydroxyaluminum amino acetate; dimethicone/PEG-10 crosspolymer; dimethicone/PEG-15 crosspolymer; dimethicone propyl PG-betaine; dimethylacrylamide/acrylic acid/polystyrene ethyl methacrylate copolymer; dimethylacrylamide/sodium acryloyldimethyltaurate crosspolymer; disteareth-100 IPDI; DMAPA acrylates/acrylic acid/acrylonitrogens copolymer; erucamidopropyl hydroxysultaine; ethylene/sodium acrylate copolymer; gelatin; gellan gum; glyceryl alginate; glycine soja (soybean) flour; guar hydroxypropyltrimonium chloride; hectorite; hyaluronic acid; hydrated silica; hydrogenated potato starch; hydrogenated tallow; hydrogenated tallowamide DEA; hydrogenated tallow betaine; hydroxybutyl methylcellulose; hydroxyethyl acrylate/sodium acryloyldimethyl taurate copolymer; hydroxyethylcellulose; hydroxyethyl chitosan; hydroxyethyl ethylcellulose; hydroxyethyl stearamide-MIPA; hydroxylauryl/hydroxymyristyl betaine; hydroxypropylcellulose; hydroxypropyl chitosan; hydroxypropyl ethylene diamine carbomer; hydroxypropyl guar; hydroxypropyl methylcellulose; hydroxypropyl methylcellulose stearoxy ether; hydroxypropyl starch; hydroxypropyl starch phosphate; hydroxypropyl xanthan gum; hydroxystearamide MEA; isobutylene/sodium maleate copolymer; isostearamide DEA; isostearamide MEA; isostearamide mIPA; isostearamidopropyl betaine; lactamide MEA; lanolinamide DEA; lauramide DEA; lauramide MEA; lauramide MIPA; lauramide/myristamide DEA; lauramidopropyl betaine; lauramidopropyl hydroxysultaine; laurimino bispropanediol; lauryl alcohol; lauryl betaine; lauryl hydroxysultaine; lauryl/myristyl glycol hydroxypropyl ether; lauryl sultaine; lecithinamide DEA; linoleamide DEA; linoleamide MEA; linoleamide MIPA; lithium magnesium silicate; lithium magnesium sodium silicate; *macrocystis pyrifera* (kelp); magnesium alginate; magnesium/aluminum/hydroxide/carbonate; magnesium aluminum silicate; magnesium silicate; magnesium trisilicate; methoxy PEG-22/dodecyl glycol copolymer; methylcellulose; methyl ethylcellulose; methyl hydroxyethylcellulose; microcrystalline cellulose; milkamidopropyl betaine; minkamide DEA; minkamidopropyl betaine; MIPA-myristate; montmorillonite; Moroccan lava clay; myristamide DEA; myristamide MEA; myristamide MIPA; myristamidopropyl betaine; myristamidopropyl hydroxysultaine; myristyl alcohol; myristyl betaine; natto gum; nonoxynyl hydroxyethylcellulose; oatamide MEA; oatamidopropyl betaine; octacosanyl glycol isostearate; octadecene/MA copolymer; oleamide DEA; oleamide MEA; oleamide MIPA; oleamidopropyl betaine; oleamidopropyl hydroxysultaine; oleyl betaine; olivamide DEA; olivamidopropyl betaine; oliveamide MEA; palmamide DEA; palmamide MEA; palmamide MIPA; palmamidopropyl betaine; palmitamide DEA; palmitamide MEA; palmitamidopropyl betaine; palm kernel alcohol; palm kernelamide DEA; palm kernelamide MEA; palm kernelamide MIPA; palm kernelamidopropyl betaine; peanutamide MEA; peanutamide MIPA; pectin; PEG-800; PEG-crosspolymer; PEG-150/decyl alcohol/SMDI copolymer; PEG-175 diisostearate; PEG-190 distearate; PEG-15 glyceryl tristearate; PEG-140 glyceryl tristearate; PEG-240/HDI copolymer bis-decyltetradeceth-20 ether; PEG-100/IPDI copolymer; PEG-180/laureth-50/ TMMG copolymer; PEG-10/lauryl dimethicone crosspolymer; PEG-15/lauryl dimethicone crosspolymer; PEG-2M; PEG-5M; PEG-7M; PEG-9M; PEG-14M; PEG-20M; PEG-23M; PEG-25M; PEG-45M; PEG-65M; PEG-90M; PEG-115M; PEG-160M; PEG-180M; PEG-120 methyl glucose trioleate; PEG-180/octoxynol-40/TMMG copolymer; PEG-150 pentaerythrityl tetrastearate; PEG-4 rapeseedamide; PEG-150/stearyl alcohol/SMDI copolymer; *phaseolus angularis* seed powder; *polianthes tuberosa* extract; polyacrylate-3; polyacrylic acid; polycyclopentadiene; polyether-1; polyethylene/isopropyl maleate/MA copolyol; polyglyceryl-3 disiloxane dimethicone; polyglyceryl-3 polydimethylsiloxyethyl dimethicone; polymethacrylic acid; polyquaternium-52; polyvinyl alcohol; potassium alginate; potassium aluminum polyacrylate; potassium carbomer; potassium carrageenan; potassium chloride; potassium palmate; potassium polyacrylate; potassium sulfate; potato starch modified; PPG-2 cocamide; PPG-1 hydroxyethyl caprylamide; PPG-2 hydroxyethyl cocamide; PPG-2 hydroxyethyl coco/isostearamide; PPG-3 hydroxyethyl soyamide; PPG-14 laureth-60 hexyl dicarbamate; PPG-14 laureth-60 isophoryl dicarbamate; PPG-14 palmeth-60 hexyl dicarbamate; propylene glycol alginate; PVP/decene copolymer; PVP montmorillonite; *pyrus cydonia* seed; *pyrus malus* (apple) fiber; rhizobian gum; ricebranamide DEA; ricinoleamide DEA; ricinoleamide MEA; ricinoleamide MIPA; ricinoleamidopropyl betaine; ricinoleic acid/adipic acid/AEEA copolymer; *rosa multiflora* flower wax; sclerotium gum; sesamide DEA; sesamidopropyl betaine; sodium acrylate/acryloyldimethyl taurate copolymer; sodium acrylates/acrolein copolymer; sodium acrylates/acrylonitrogens copolymer; sodium acrylates copolymer; sodium acrylates crosspolymer; sodium acrylate/sodium acrylamidomethylpropane sulfonate copolymer; sodium acrylates/vinyl isodecanoate crosspolymer; sodium acrylate/vinyl alcohol copolymer; sodium carbomer; sodium carboxymethyl chitin; sodium carboxymethyl dextran; sodium carboxymethyl beta-glucan; sodium carboxymethyl starch; sodium carrageenan; sodium cellulose sulfate; sodium chloride; sodium cyclodextrin sulfate; sodium hydroxypropyl starch phosphate; sodium isooctylene/MA copolymer; sodium magnesium fluorosilicate; sodium oleate; sodium palmitate; sodium palm kernelate; sodium polyacrylate; sodium polyacrylate starch; sodium polyacryloyldimethyl taurate; sodium polygamma-glutamate; sodium polymethacrylate; sodium polystyrene sulfonate; sodium silicoaluminate; sodium starch octenylsuccinate; sodium stearate; sodium stearoxy PG-hydroxyethylcellulose sulfonate; sodium styrene/acrylates copolymer; sodium sulfate; sodium tallowate; sodium tauride acrylates/acrylic acid/acrylonitrogens copolymer; sodium tocopheryl phosphate; *solanum tuberosum* (potato) starch; soyamide DEA; soyamidopropyl betaine; starch/acrylates/acrylamide copolymer; starch hydroxypropyltrimonium chloride; stearamide AMP; stearamide DEA; stearamide DEA-distearate; stearamide DIBA-stearate; stearamide MEA; stearamide MEA-stearate; stearamide MIPA; stearamidopropyl betaine; steareth-60 cetyl ether; steareth-100/PEG-136/HDI copolymer; stearyl alcohol; stearyl betaine; *sterculia urens* gum; synthetic fluorphlogopite; tallamide DEA; tallow alcohol; tallowamide DEA; tallowamide MEA; tallowamidopropyl betaine; tallowamidopropyl hydroxysultaine; tallowamine oxide; tallow betaine; tallow dihydroxyethyl betaine; tamarindus indica seed gum; tapioca starch; TEA-alginate; TEA-carbomer; TEA-hydrochloride; trideceth-2 carboxamide MEA; tridecyl alcohol; triethylene glycol dibenzoate; trimethyl pentanol hydroxyethyl ether; *triticum vulgare* (wheat) germ powder; *triticum vulgare* (wheat) kernel flour; *triticum vulgare* (wheat) starch; tromethamine acrylates/acrylonitrogens copolymer; tromethamine magnesium aluminum silicate; undecyl alcohol; undecylenamide DEA; undecylenamide MEA; undecylenamidopropyl betaine; welan gum; wheat germamide DEA; wheat germamidopropyl betaine; xanthan gum; yeast beta-glucan; yeast polysaccharides and *zea mays* (corn) starch.

In some embodiments, one function of the carrier is to enhance skin penetration of the active ingredients. Permeation enhancers are compounds which promote skin permeability by altering the skin as a barrier to the flux of a desired penetrant. These may be classified as solvents, surfactants and miscellaneous chemicals. Suitable carriers are well known to skilled practitioners, and include liposomes, ethanol, dimethylsulfoxide (DMSO), petroleum jelly (petrolatum), mineral oil (liquid petrolatum), water, deimethylformamide, dekaoxyethylene-oleylether, oleic acid, 2-pyrrolidone, Azone® brand penetration enhancer (Upjohn), biologically acceptable glycols, diglycols, polyglycols; alkyoxy C2-C8 alcohols, ethoxydiglycol and dimethyl isosorbide. A skin penetration enhancer may be included at concentrations ranging from 5% to 95%, preferably 5% to 10% of the total composition.

In a further embodiment of the combinations described above, a topical formulation is prepared that comprises a composition for cosmetic or dermatological use, which composition comprises a cosmetically and/or dermatologically effective amount of the combination stated above.

In one embodiment, the compositions are in a form suitable for cosmetic application including, but not limited to, lotions, ointments, creams, sprays, spritzes, aqueous or aqueous-alcoholic mixture gels, mousses, patches, pads, masks, moistened clothes, wipes, solid sticks, clear sticks, lip sticks, aerosol creams, anhydrous powders, talcs, tonics, oils, emulsions or bath salts.

In another embodiment, the composition also contains irritation-mitigating additives to minimize or eliminate the possibility of skin irritation or skin damage resulting from the chemical compound to be administered, or other components of the composition. Suitable irritation-mitigating additives include for example: tocopherols, monoamine oxidase inhibitors (e.g., 2-phenyl-1-ethanol), glycerin, salicylates, ascorbates (e.g., tetrahexyldecyl ascorbate), ionophores (e.g., monensin), amphiphilic amines, animonium chloride, N-acetylcysteine, capsaicin, and/or chloroquine.

Modulation of Melanin Production

In some embodiments, the compositions disclosed herein modulate melanin product in a subject in need thereof. For example, the compositions disclosed herein may decrease melanin production to reduce pigmentation in a subject in need thereof. The compositions disclosed herein may also function to decrease the number of melanocytes present in the epidermis, effectively decreasing melanin production and reducing pigmentation in a subject in need thereof. A decrease in melanin production may be desirable in the skin, hair, pigmented pigmented tissue underlying the iris of the eye, or the stria vascularis of the inner ear. Administration or targeting of the compositions disclosed herein may act to locally effect melanin production and reduce pigmentation.

Hyperpigmentation or hypermelanosis disorders due to environmental stressors, such as hormonal imbalance, can also affect melanin or pigmentation levels in the skin. Hyperpigmentation or hypermelanosis disorders may also be due to physiological stressors or mechanical stressors.

Prostaglandin F2 alpha (PGF2 alpha) is a bioactive molecule in the prostanoid family of lipid mediators that regulate numerous processes in the body, including inflammation. While not wishing to be limited to a specific theory or mechanism of action, it is believed that the compositions disclosed herein may act in two (2) ways to modulate melanin distribution: 1) through the modulation of melanin production by melanocytes; and 2) by affecting melanin distribution by melanocytes.

4-ethoxybenzaldehyde has been demonstrated to affect a wide variety of inflammatory conditions, such as rheumatoid arthritis, febrile conditions, edema, hyperalgesia, inflammatory bowel disease, and periodontal disease. However, 4-ethoxybenzaldehyde has not previously been shown to be useful in the treatment of hyperpigmentation, including post-inflammatory hyperpigmentation, or to lighten skin.

In one aspect, provided herein is a method of treating hyperpigmentation or a hypermelanosis disorder in an individual, comprising administering to the individual in need thereof an effective amount of a composition comprising:

from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.5%.

In another aspect, provided herein is a method of treating hyperpigmentation or a hypermelanosis disorder in an individual, comprising administering to the individual in need thereof an effective amount of a composition comprising: about 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In another aspect, provided herein is a method of treating hyperpigmentation or a hypermelanosis disorder in an individual, comprising administering to the individual in need thereof an effective amount of a composition comprising: about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In some embodiments, the method reduces melanin distribution by about 10% to about 40%.

Application of the compositions in the methods described herein may be topical or transdermal administeration to the skin of the individual.

In one embodiment, the pharmaceutically or cosmetically acceptable carrier is a topical carrier. Topical carriers include, for example, a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

In one embodiment, hyperpigmentation may result from an environmental stressor (e.g., excessive sun exposure or chemical exposure), physiological stressor (e.g., a hormonal disorder), or mechanical stressor.

Compositions described herein for use in such methods may further include one or more additional active agents. For example, an additional active agent may be an antioxidant, a sunscreen, a sunprotectant, a sunblock, a skin-lightening agent, an anti-inflammatory agent, an anti-acne agent or mixtures thereof. Compositions described herein for use in such methods may further include one or more of a solvent, film former, preservative, viscosity increasing agent, fragrance, surfactant, chelating agent, humectant, permeation enhancer, excipients, or a combination thereof.

Exemplary antioxidants include vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, Tocopherol, *Dunaliella Salina* Extract or combinations thereof.

Exemplary skin-lightening agents include hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropyl-cetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

In another aspect, provided herein is a method of lightening skin in an individual, comprising administering to the individual in need thereof an effective amount of a composition comprising: from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.5%.

In another aspect, provided herein is a method of lightening skin in an individual, comprising administering to the individual in need thereof an effective amount of a composition comprising: about 0.1% to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In another aspect, provided herein is a method of lightening skin in an individual, comprising administering to the individual in need thereof an effective amount of a composition comprising: about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In one embodiment, the amount of substituted benzaldehyde in the composition is about 0.5%. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In some embodiments, the methods decrease the level of pigmentation by about 5%, by about 10%, by about 20%, by about 30% or by about 40%.

The methods may be used to treat hyperpigmentation or a hypermelanosis disorder. In one embodiment, hyperpigmentation may result from an environmental stressor (e.g., excessive sun exposure or chemical exposure), physiological stressor (e.g., a hormonal disorder), or mechanical stressor.

In some embodiments, the method reduces melanin distribution by about 10% to about 40%.

Application of the compositions in the methods described herein may be topical or transdermal administeration to the skin of the individual.

In one embodiment, the pharmaceutically or cosmetically acceptable carrier is a topical carrier. Topical carriers include, for example, a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

Compositions described herein for use in such methods may further include one or more additional active agents. For example, an additional active agent may be an antioxidant, a sunscreen, a sunprotectant, a sunblock, a skin-lightening agent, an anti-inflammatory agent, an anti-acne agent or mixtures thereof. Compositions described herein for use in such methods may further include one or more of a solvent, film former, preservative, viscosity increasing agent, fragrance, surfactant, chelating agent, humectant, permeation enhancer, excipients, or a combination thereof.

Exemplary antioxidants include vitamin E, Coenzyme Q10, idebenone, lycopene, green tea polyphenols, silybin, resveratrol, grape seed extract, Oregon grape root (*Mahonia aquifolium*) extract, pomegranate extract, genistein, pycnogenol, curcumin, curcuminoids, tetrahexyldecyl Tocopherol, *Dunaliella Salina* Extract or combinations thereof.

Exemplary skin-lightening agents include hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), phytic acid or combinations thereof.

Provided are methods of modifying melanin distribution by modulating prostaglandin F2 alpha (PGF2 alpha) in a cell, comprising contacting said cell with a composition comprising from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the cells being treated are located in skin of an individual.

Also disclosed are methods of modifying melanin distribution by modulating prostaglandin F2 alpha (PGF2 alpha) in skin cells in an individual, comprising administering to the individual in need thereof an effective amount of a composition comprising from about 0.01% to about 2% substituted benzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

In one embodiment, the amount of substituted benzaldehyde in the composition is about 0.5%.

Substituted benzaldehydes for use in the compositions include, for example, 2-ethoxybenzaldehyde, 4-ethoxybenzaldehyde, 4-allyloxybenzaldehyde or 4-propoxybenzaldehyde. In one embodiment, the substituted benzaldehyde is 4-ethoxybenzaldehyde, which may be present in the composition in an amount of about 0.5%.

In some embodiments, provided are methods of modifying melanin distribution by modulating prostaglandin F2 alpha (PGF2 alpha) in a cell, comprising contacting said cell with a composition comprising about 0.1 to about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the cells being treated are located in skin of an individual. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Provided are methods of modifying melanin distribution by modulating prostaglandin F2 alpha (PGF2 alpha) in a cell, comprising contacting said cell with a composition comprising about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In some embodiments, the cells being treated are located in skin of an individual. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate.

Also provided are methods of modifying melanin distribution by modulating prostaglandin F2 alpha (PGF2 alpha) in skin cells in an individual, comprising administering to the individual in need thereof an effective amount of a composition comprising about 0.5% 4-ethoxybenzaldehyde, about 0.01% to about 5.0% each of Retinol, Niacinamide, Tetrahexyldecyl Ascorbate, *Glycyrrhiza Glabra* (Licorice) Root Extract, Hexyl Resorcinol, ethyl linoleate, and a pharmaceutically or cosmetically acceptable carrier. In another embodiment, the composition comprises from about 0.1% to about 0.75%, from about 0.05% to about 1.0%, or from about 0.01% to about 2% Retinol. In another embodiment, the composition comprises from about 2.0% to about 8.0%, from about 1% to about 10%, or from about 0.5% to about 15.0% Niacinamide. In another embodiment, the composition comprises from about 1.0% to about 5.0%, from about 0.5% to about 8.0%, or from about 0.1% to about 15% Tetrahexyldecyl Ascorbate. In another embodiment, the composition comprises from about 0.001% to about 0.5%, from about 0.0005% to about 1.0% or from about 0.0001% to about 2% Licorice root extract. In another embodiment, the composition comprises from about 0.1% to about 3.0%, from about 0.05% to about 5.0%, or from about 0.01% to about 10.0% Resorcinol. In another embodiment, the composition comprises from about 0.1% to about 3.0%, from about 0.05% to about 5.0%, or from about 0.01% to about 10.0% ethyl linoleate. In some embodiments, the method reduces melanin distribution by about 10% to about 40%.

Application of the compositions in the methods described herein may be topical or transdermal administeration to the skin of the individual.

In one embodiment, the pharmaceutically or cosmetically acceptable carrier is a topical carrier. Topical carriers include, for example, a water-in-oil emulsion, cream, liquid, gel, oil, paste, ointment, suspension, foam, lotion, oil-in-water emulsion, water-in-oil-in-water emulsion, water-in-silicone emulsion, spray or serum carrier.

Compositions described herein for use in such methods may further include one or more additional active agents. For example, an additional active agent may be an antioxidant, a sunscreen, a sunprotectant, a sunblock, a skin-lightening agent, an anti-inflammatory agent, an anti-acne agent or mixtures thereof. Compositions described herein for use in such methods may further include one or more of a solvent, film former, preservative, viscosity increasing agent, fragrance, surfactant, chelating agent, humectant, permeation enhancer, excipients, or a combination thereof.

Exemplary antioxidants include vitamin E, Coenzyme Q10, idebenone, lycopene, green tea polyphenols, silybin, resveratrol, grape seed extract, Oregon grape root (*Mahonia*

*aquifolium*) extract, pomegranate extract, genistein, pycnogenol, curcumin, curcuminoids, Tocopherol, *Dunaliella Salina* Extract or combinations thereof.

Exemplary skin-lightening agents include hydroquinone, monobenzyl ether of hydroquinone, azelaic acid, kojic acid, mequinol, retinoids, soy proteins, alpha-hydroxy acids, trichloroacetic acid, salicylic acid, hydroquinone-beta-D-glucopyranoside, paper mulberry, glabridin, 4-isopropylcetchol, aleosin, N-acetyl-4-S-cycteaminylphenol, N-propionyl-4-S-cysteaminylphenol, N-acetyl glucosamine, tranexaminc acid, an alpha MSH antagonist (e.g. undecylenoyl phenylalanine), or phytic acid combinations thereof.

In one aspect, one patient population to be treated by the present methods is described below in Example 13. Representative patients include those with Fitzpatrick skin types I-IV. Fitzpatrick skin classification is based on the skin's unprotected response to the first 30 to 45 minutes of sun exposure after a winter season without sun exposure. The categories of skin types are as follows: (I): Always burns easily; never tans; (II): Always burns easily; tans minimally; (III): Burns moderately; tans gradually; (IV): Burns minimally; always tans well; (V): Rarely burns; tans profusely; and (VI): Never burns; deeply pigmented. Patients also may exhibit the presence of clinically determined moderate to severe dyspigmentation on the face as determined by a score of 4-9 from the Overall Hyperpigmentation scale. Individuals to be treated are in good general health and free of any disease state or physical condition (e.g., psoriasis, moderate to severe rosacea, hirsutism, scars, tattoos, etc.) which might increase the health risk to the subject by treatment. Individuals to be treated include those who have not used systemic retinoids (e.g., Tazorac, Soriataine, Accutane, etc.) and/or any other systemic medication known to affect melasma at least 60 days prior to treatment and are not to use these products during treatment. Individuals to be treated are not to use topical retinoids and/or all other topical medication (e.g., topical steroids, products containing benzoyl peroxide, alpha- or beta-hydroxy acids, hydroquinone, and/or any other over the counter (OTC) skin treatment medications) to the facial area known to affect melasma at least 14 days prior to treatment and are not to use these products during treatment. Patients should be willing to avoid extended periods of sun exposure during treatment. If brief (less than 20 minutes) periods of sun exposure cannot be avoided, then subjects are asked to use an SPF 30 product and wear protective clothing prior to and during exposure.

In another aspect, an individual will not be eligible for treatment if they meet any of the following exclusion criteria: Individuals with known allergies or sensitivities to skin lightening products, retinoids, hydroquinone, sulfites, moisturizers, or other facial products. Individuals with active symptoms of allergy, active psoriasis or eczema, sunburn, excessive scarring, tattoos, or other skin condition in the areas to be treated. Individuals who are nursing, pregnant, or planning to become pregnant during treatment. Individuals having uncontrolled disease such as diabetes, hypertension, hyper or hypo-thyroidism, active hepatitis, immune deficiency, or autoimmune disease as determined by the initial paperwork. Individuals who require electrolysis, waxing, or use depilatories on the face during conduct of the study. Individuals who have had a facial peel or a laser treatment of the face within 60 days prior to treatment. Individuals who have a pre-existing or dormant dermatologic condition (e.g., psoriasis, atopic dermatitis, advanced skin cancer, rosacea, other inflammatory disorder, etc.). Individuals who are receiving treatment for a skin disorder with another composition.

In another aspect, another patient population to be treated by the present methods is described below in Example 14. Representative patients include those with Fitzpatrick skin type III and those who are in general good health as determined by review of their health.

In another aspect, an individual will not be eligible for treatment if they meet any of the following exclusion criteria: Individuals with Fitzpatrick skin types I, II, IV, V and VI. Individuals that have been instructed by a physician, pharmacist, or health professional to avoid sunlight because of a medical condition and/or because of drug contraindications. Individuals with known abnormal responses to sunlight or UVR light sources. Individuals with a known allergy to any ingredient in a personal care product. Individuals with known atopic skin diseases or neurodermatitis. Women known to be pregnant, nursing, or planning to become pregnant within 6 months. Individuals known to be treated for cancer or have a history of cancer. Individuals with observable sunburn, suntan, scars, uneven tone/pigmentation, nevi or other dermal conditions on the areas to be treated that might influence the results. Individuals with uncontrolled high blood pressure, individuals with dermal hypersensitivity requiring treatments with medications. Individuals taking medication(s) which would interfere with the subject's treatment. Such medications include, but are not limited to, antihypertensive agents (hydrochorothiazide, furosemide, meticrane), ataractics (e.g., perphenazine), psychotropic agents (e.g., chlorpromazine), antihistamines (e.g., promethazine hydrochloride), oral hypoglycemic agents (e.g., tolubutamide, chlorpropamide), and tetracycline antibiotics (e.g., dimethylchlorotetracycline, tetracycline).

Method of Administration

In some embodiments, any composition described herein is administered in the form of a cosmetic composition. In some embodiments, the cosmetic composition can be prepared according to procedures well known in the cosmetic arts and comprise at least one active compound and two antioxidant agents.

In some embodiments, the cosmetic composition is administered topically. In specific embodiments, the cosmetic composition is administered transdermally so that the active agent and antioxidant agents contact the skin. In a further or additional embodiment, the composition is administered transdermally so as to deliver the compositions disclosed herein systemically.

The compositions disclosed herein contain one or more substituted benzaldehyde and an optional at least one additional active agent. The amounts used are amounts effective such that when administered to a subject for treating a disease, cosmetic or dermatological condition, is sufficient to effect such treatment for the disease, cosmetic or dermatological condition. Here, the amount will depend upon the endpoint desired, for example, the modification, for example the increase or reduction of melanin and/or melanocyte production and/or distribution. The endpoint can be measured in terms of the subjective interpretation of the subject being administered the disclosed compositions. For example, the endpoint may be a study by which a subject is queried if the treatment regimen is "satisfactory" or "unsatisfactory". Alternatively, the endpoint may be measured quantitatively in terms of the amount of melanin and/or melanocytes in a given subject or experimental procedure. The endpoint may be measured by a trained medical professional, for example a physician or nurse, or by a subject or other individual. The endpoint may additionally be determined remotely, for example, through comparisons of photographs or other recordings by a trained medical professional or other individual. Furthermore, the degree of modification of melanin production may be predetermined by a trained medical professional, for example, by assigning a predetermined degree of melanin and/or melanocyte presence as an endpoint value.

The "effective amount", however, will take into account any toxicity effects that may occur, for example, severe skin irritation with higher doses of the active agents disclosed herein. Suggested endpoints may first be measured in vitro or in an animal model to determine the acceptable range of active agents to be used in conjunction with the compositions disclosed herein. One of ordinary skill in the art can then extrapolate doses that will avoid toxicity but maintain efficacy in treated subjects, including humans. The "effective amount" can vary depending on the compound, the disease and its severity, and the age, weight, etc., of the subject to be treated.

In certain embodiments, the compositions disclosed herein comprises a substituted benzaldehyde in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 22% or about 25%. Preferably, the compositions disclosed herein comprises a substituted benzaldehyde in a concentration from about 0.01% to about 50%, from about 0.1% to about 30%, from about 0.1% to about 20%, from about 0.5% to about 20%, from about 0.5% to about 10%, from about 0.5% to about 5%, from about 0.5% to about 3%, from about 0.5% to about 2.0%, from about 0.5% to about 1.5%, from about 0.75% to about 10%, from about 0.75% to about 7.5%, from about 0.75% to about 5%, from about 1% to about 10%, from about 1% to about 5%, from about 1% to about 2.5%, from about 1% to about 2%, from about 0.1% to about 2%, from about 0.01% to about 2%, from about 0.01% to about 2%, from about 0.01% to about 2%, from about 0.1% to about 1%, from about 0.1% to about 0.5%, or from about 0.5% to about 2%.

The compositions disclosed herein may contain from about 0.01 mg to about 100 mg of substituted benzaldehyde or about 0.1 mg to about 10 mg of substituted benzaldehyde. In some embodiments, the compositions disclosed herein may contain from about 0.05 to about 5 mg of substituted benzaldehyde, or from about 0.1 to about 3 mg of substituted benzaldehyde. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of substituted benzaldehyde. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of substituted benzaldehyde. In some embodiments, the compositions disclosed herein will contain from about 0.3 mg to about 0.75 mg of substituted benzaldehyde.

In some embodiment, the compositions disclosed herein comprises 4-ethoxybenzaldehyde in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 22%, about 25%, about 30% or about 40%. Preferably, the compositions disclosed herein comprises a 4-ethoxybenzaldehyde in a concentration from about 0.01% to about 50%, from about 0.1% to about 30%, from about 0.1% to about 20%, from about 0.5% to about 20%, from about 0.5% to about 10%, from about 0.5% to about 5%, from about 0.5% to about 3%, from about 0.5% to about 2.0%, from about 0.5% to about 1.5%, from about 0.75% to about 10%, from about 0.75% to about 7.5%, from about 0.75% to about 5%, from about 1% to about 10%, from about 1% to about 5%, from about 1% to about 2.5%, from about 1% to about 2%, from about 0.1% to about 2%, from about 0.01% to about 2%, from about 0.01% to about 2%, from about 0.01% to about 2%, from about 0.1% to about 1%, from about 0.1% to about 0.5%, or from about 0.5% to about 2%.

The compositions disclosed herein may also have a concentration of 4-ethoxybenzaldehyde of from about 0.01 mg/ml to about 50 mg/ml, preferably from about 0.1 mg/ml to about 10 mg/ml. In some embodiments, the compositions disclosed herein may have a concentration of 4-ethoxybenzadehyde of from about 0.1 mg/ml to about 5 mg/ml, or from about 0.3 mg/ml to about 3 mg/ml. In some embodiments, the compositions will have a concentration of 4-ethoxybenzaldehyde of from about 0.1 to about 50 mg/ml, from about 0.1 to about 45 mg/ml, from about 0.1 to about 40 mg/ml, from about 0.1 to about 35 mg/ml, from about 0.1 to about 30 mg/ml, from about 0.1 to about 25 mg/ml, from about 0.1 to about 20 mg/ml, from about 0.1 to about 15 mg/ml, from about 0.1 to about 10 mg/ml, from about 0.1 to about 5 mg/ml, 0.5 to about 50 mg/ml, from about 0.5 to about 45 mg/ml, from about 0.5 to about 40 mg/ml, from about 0.5 to about 35 mg/ml, from about 0.5 to about 30 mg/ml, from about 0.5 to about 25 mg/ml, from about 0.5 to about 20 mg/ml, from about 0.5 to about 15 mg/ml, from about 0.5 to about 10 mg/ml, from about 0.5 to about 5 mg/ml, 1.0 to about 50 mg/ml, from about 1.0 to about 45 mg/ml, from about 1.0 to about 40 mg/ml, from about 1.0 to about 35 mg/ml, from about 1.0 to about 30 mg/ml, from about 1.0 to about 25 mg/ml, from about 1.0 to about 20 mg/ml, from about 1.0 to about 15 mg/ml, from about 1.0 to about 10 mg/ml, from about 1.0 to about 5 mg/ml, 2.5 to about 50 mg/ml, from about 2.5 to about 45 mg/ml, from about 2.5 to about 40 mg/ml, from about 2.5 to about 35 mg/ml, from about 2.5 to about 30 mg/ml, from about 2.5 to about 25 mg/ml, from about 2.5 to about 20 mg/ml, from about 2.5 to about 15 mg/ml, from about 2.5 to about 10 mg/ml, from about 2.5 to about 5 mg/ml of 4-ethoxybenzaldehyde. In some embodiments, the compositions disclosed herein will have a concentration of 4-ethoxybenzaldehyde of 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 13, 13.5, 14, 14.5, 15, 16, 17, 18, 19, 20, 25, 30, 35 40, 45 or 50 mg/ml.

In other embodiments, the compositions disclosed herein further includes an antioxidant in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of antioxidant from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of antioxidant or about 0.1 mg to about 10 mg of antioxidant. In some embodiments, the compositions disclosed herein may contain from about 0.05 to about 5 mg of antioxidant, or from about 0.1 to about 3 mg of antioxidant. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of antioxidant. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of antioxidant. In some embodiments, the compositions disclosed herein will contain from about 0.3 mg to about 0.75 mg of antioxidant.

In other embodiments, the compositions disclosed herein further comprises a skin-lightening agent in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of skin-lightening agents from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of skin-lightening agent or about 0.1 mg to about 10 mg of skin-lightening agent. In some embodiments, the compositions disclosed herein may contain from about 0.05 to about 5 mg of skin-lightening agent, or from about 0.1 to about 3 mg of skin-lightening agent. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of skin-lightening agent. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of skin-lightening agent. In some embodiments, the compositions disclosed herein will contain from about 0.3 mg to about 0.75 mg of skin-lightening agent.

In some embodiments, the compositions disclosed herein further comprises a sunscreen agent in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of sunscreen agents from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of a sunscreen agent or about 0.1 mg to about 10 mg of a sunscreen agent. In some embodiments, the compositions disclosed herein may contain from about 0.05 to about 5 mg of sunscreen agent, or from about 0.1 to about 3 mg of sunscreen agent. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of sunscreen agent. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of sunscreen agent. In some embodiments, the compositions disclosed herein will contain from about 0.3 mg to about 0.75 mg of sunscreen agent.

In some embodiments, the compositions disclosed herein further comprises an anti-acne agent in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of an anti-acne agent from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of anti-acne agent or about 0.1 mg to about 10 mg of anti-acne agent. In some embodiments, the compositions disclosed herein may contain from about 0.05 to about 5 mg of anti-acne agent, or from about 0.1 to about 3 mg of anti-acne agent. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of anti-acne agent. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of anti-acne agent. In some embodiments, the compositions disclosed herein will contain from about 0.3 mg to about 0.75 mg of anti-acne agent.

In some embodiments, the compositions disclosed herein further comprises an anti-inflammatory agent in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of anti-inflammatory agents from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of anti-inflammatory agent or about 0.1 mg to about 10 mg of anti-inflammatory agent. In some embodiments, the compositions disclosed herein may contain from about 0.05 to about 5 mg of anti-inflammatory agent, or from about 0.1 to about 3 mg of anti-inflammatory agent. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of anti-inflammatory agent. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of anti-inflammatory agent. In some embodiments, the compositions disclosed herein will contain from about 0.3 mg to about 0.75 mg of anti-inflammatory agent.

In some embodiments, the compositions disclosed herein further comprises an emollient in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of emollients from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of emollient or about 0.1 mg to about 10 mg of emollient. In some embodiments, the compositions disclosed herein may contain from about 0.05 to about 5 mg of emollient, or from about 0.1 to about 3 mg of emollient. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of emollient. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of emollient. In some embodiments, the compositions disclosed herein will contain from about 0.3 mg to about 0.75 mg of emollient.

In some embodiments, the compositions disclosed herein further comprises a film former in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of film formers from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of film former or about 0.1 mg to about 10 mg of film former. In some embodiments, the compositions disclosed herein may contain from about 0.05 to about 5 mg of emollient, or from about 0.1 to about 3 mg of film former. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of film former. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of film former. In some embodiments, the compositions disclosed herein will contain from about 0.3 mg to about 0.75 mg of film former.

In some embodiments, the compositions disclosed herein further comprises an occlusive in a concentration of about 0.01%, about 0.05%, about 0.08%, about 0.1%, about 0.15%, about 0.2%, about 0.5%, about 0.8%, about 1%, about 1.3%, about 1.5%, about 1.8%, about 2%, about 2.3%, about 2.5%, about 2.8%, about 3%, about 3.5%, about 4%, about 5%, about 8%, about 10%, about 13%, about 15%, about 18%, about 20%, about 23%, about 25%. In yet other embodiments, the compositions disclosed herein comprises a range of occlusives from about 0.1% to about 25%, from about 0.5% to about 20%, from about 0.5% to about 10%, from about 0.5% to about 5%, from about 0.5% to about 3%, from about 0.75% to about 10%, from about 0.75% to about 7.5%, from about 0.75% to about 5%, from about 1% to about 10%, from about 1% to about 5%, from about 1% to about 2.5%, or from about 1% to about 2%.

The compositions disclosed herein may contain from about 0.01 mg to about 100 mg of occlusive or about 0.1 mg to about 10 mg of film former. In some embodiments, the compositions disclosed herein may contain from about 0.05 to about 5 mg of occlusive, or from about 0.1 to about 3 mg of occlusive. In some embodiments, the compositions disclosed herein may contain from about 0.1 to about 50 mg, from about 0.1 to about 45 mg, from about 0.1 to about 40 mg, from about 0.1 to about 35 mg, from about 0.1 to about 30 mg, from about 0.1 to about 25 mg, from about 0.1 to about 20 mg, from about 0.1 to about 15 mg, from about 0.1 to about 10 mg, from about 0.1 to about 5 mg, from about 0.5 to about 50 mg, from about 0.5 to about 45 mg, from about 0.5 to about 40 mg, from about 0.5 to about 35 mg, from about 0.5 to about 30 mg, from about 0.5 to about 25 mg, from about 0.5 to about 20 mg, from about 0.5 to about 15 mg, from about 0.5 to about 10 mg, from about 0.5 to about 5 mg, from about 1.0 to about 50 mg, from about 1.0 to about 45 mg, from about 1.0 to about 40 mg, from about 1.0 to about 35 mg, from about 1.0 to about 30 mg, from about 1.0 to about 25 mg, from about 1.0 to about 20 mg, from about 1.0 to about 15 mg, from about 1.0 to about 10 mg, from about 1.0 to about 5 mg, from about 2.5 to about 50 mg, from about 2.5 to about 45 mg, from about 2.5 to about 40 mg, from about 2.5 to about 35 mg, from about 2.5 to about 30 mg, from about 2.5 to about 25 mg, from about 2.5 to about 20 mg, from about 2.5 to about 15 mg, from about 2.5 to about 10 mg, and from about 2.5 to about 5 mg of occlusive. In some embodiments, the compositions disclosed herein will contain from about 0.1 mg, 0.2 mg, 0.3 mg, 0.4 mg, 0.5, mg, 0.6 mg, 0.7 mg, 0.8 mg, 0.9 mg, 1.0 mg, 2.0 mg, 3.0 mg, 4.0 mg, 5.0 mg, 7.0 mg, 10.0 mg, 15.0 mg, 20 mg, 25 mg, 30 mg, 35 mg, 40 mg, 45 mg, 50 mg, 60 mg, 70 mg, 80 mg, 90 mg or 100 mg of occlusive. In some embodiments, the compositions disclosed herein will contain from about 0.3 mg to about 0.75 mg of occlusive.

In some embodiments, the compositions disclosed herein are administered twice daily, three times a day, four times a day or more. In other embodiments, the compositions disclosed herein are administered once a day, once every other day, once every three days, once every four days, once every five days, once every six days, once a week, once every two weeks, once a month, or less frequently. In some embodiments, the compositions administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Dosing Effects

In other embodiments, the compositions are administered in an amount to achieve a desired cosmetic effect. In some embodiments, the level of pigmentation is decreased by about 5%, by about 10%, by about 12%, by about 15%, by about 17%, by about 20%, by about 25%, by about 30%, by about 35%, by about 40%, by about 45%, by about 45%, by about 50%, by about 55%, by about 60%, by about 65%, by about 70%, by about 75%, by about 80% or more. In some embodiments, the methods decrease the level of pigmentation by about 5%, by about 10%, by about 20%, by about 30% or by about 40%. In some embodiments, the level of pigmentation is increased by about 5%, by about 10%, by about 12%, by about 15%, by about 17%, by about 20%, by about 25%, by about 30%, by about 35%, by about 40%, by about 45%, by about 45%, by about 50%, by about 55%, by about 60%, by about 65%, by about 70%, by about 75%, by about 80% or more.

In some embodiments, an even skin tone or pigmentation is desired, for example, in subjects afflicted with uneven pigmentation, such as vitiligo or uneven melanin distribution. In some embodiments, the level of pigmentation is uniformly increased or decreased in localized areas to achieve an even skin tone or pigmentation distribution. In some embodiments, the level of pigmentation in localized areas is decreased towards a more uniform distribution of melanin or melanocytes by about 1%, about 2%, about 3%, about 4%, about 5%, about 6%, by about 7%, about 7%, about 8%, about 9%, by about 10%, by about 12%, by about 15%, by about 17%, by about 20%, by about 25%, by about 30%, by about 35%, by about 40%, by about 45%, by about 45%, by about 50%, by about 55%, by about 60%, by about 65%, by about 70%, by about 75%, by about 80% or more. In some embodiments, the level of pigmentation in localized areas is increased towards a more uniform distribution of melanin or melanocytes by about 1%, about 2%, about 3%, about 4%, about 5%, about 6%, by about 7%, about 7%, about 8%, about 9%, by about 10%, by about 12%, by about 15%, by about 17%, by about 20%, by about 25%, by about 30%, by about 35%, by about 40%, by about 45%, by about 45%, by about 50%, by about 55%, by about 60%, by about 65%, by about 70%, by about 75%, by about 80% or more.

In some embodiments, levels of PGF-2alpha are decreased by about 1%, about 2%, about 3%, about 4%, about 5%, about 6%, by about 7%, about 7%, about 8%, about 9%, by about 10%, by about 12%, by about 15%, by about 17%, by about 20%, by about 25%, by about 30%, by about 35%, by about 40%, by about 45%, by about 45%, by about 50%, by about 55%, by about 60%, by about 65%, by about 70%, by about 75%, by about 80% or more.

EXAMPLES

Example 1

Inhibition of Prostaglandin F2 Alpha Levels

Human keratinocytes were harvested and exposed to with UVB light to induce PGF2 alpha release. Following exposure to UVB irradiation, the cells were treated with a composition comprising 1% 4-ethoxybenzaldehyde, Indomethacin (positive control) or left untreated (negative control). After 24 hours post-treatment, PGF2 alpha levels were measured by ELISA analysis. The composition comprising 4-ethoxybenzaldehyde provided dose-dependent inhibition of PGF2 alpha in UVB-induced cells (FIG. 1).

Example 2

Skin Tone Clinical Study

Approximately 30 healthy subjects, aged 20-64 years with Fitzpatrick Skin Types I-III, are enrolled in this single-center, double-blinded comparison study. Assignments of the test product or vehicle to subjects are randomized 2:1 to avoid bias. A total of approximately 15 subjects receive the test product and 15 subjects receive the vehicle. Subjects follow a twice-daily product application regiment for 4 weeks. No other moisturizers, lotions or products are allowed to be applied during the study. At the baseline visit, subjects are graded by a dermatologist for uneven skin tone on their facial skin. Standardized digital photographs of the test site (i.e., face) are also taken. At the end of week 2, subjects are graded by a dermatologist for uneven skin tone on their facial skin. Standardized digital photographs of the test site (i.e., face) are also taken. Twice-daily application of test product continues for another 14 days. At the end of 4 weeks, subjects are graded by a dermatologist for uneven skin tone on their facial skin. Standardized digital photographs of the test site (i.e., face) are also taken.

Example 3

Post-Inflammatory Hyperpigmentation Clinical Study

UV irradiation stimulates a variety of biochemical pathways in the skin, resulting in free radical formation as well as the release of inflammatory mediators. The short-term clinical effects observed from these pathways, include cutaneous inflammation and erythema, while long-term effects (for example, in the absence of treatment of the inflammatory response) result in photodamaged skin. UV irradiation may also cause the development of post-inflammatory hyperpigmentation since it induces an inflammatory response in the skin that can proceed to hyperpigmentation.

The 17 healthy female subjects, aged 26-63 years with Fitzpatrick Skin Types III-IV, were enrolled and completed this single-center, double-blinded comparison study. At baseline, test areas were marked onto the backs of the subjects: Untreated control, 1% w 4EB composition, antioxidant product, and other test products. Assignments of the test products to test areas were randomized to avoid site bias. The minimal erythemal dose (MED) for each subject was also determined, using a solar simulator with a spectral output comparable to that of natural solar radiation (UVB: 290-320 nm, UVA: 320-400 nm). Thirty micro liters of each test product were applied to the respective test sites by the study staff, once daily, for 4 days. On Day 5, test sites were irradiated with 1.0, 1.5, 2.0, and 2.5 MEDs. On Day 6, standardized digital photographs were taken of the test sites and test product application resumed for an additional eleven days. Standardized digital photographs were taken of the test sites on Day 20. The images were analyzed using a computer-aided colorimetry algorithm, according to the CIE color standard, to determine $a^*$ (redness) on Day 6 and $L^*$ (brightness) on Day 20.

Figure 2:
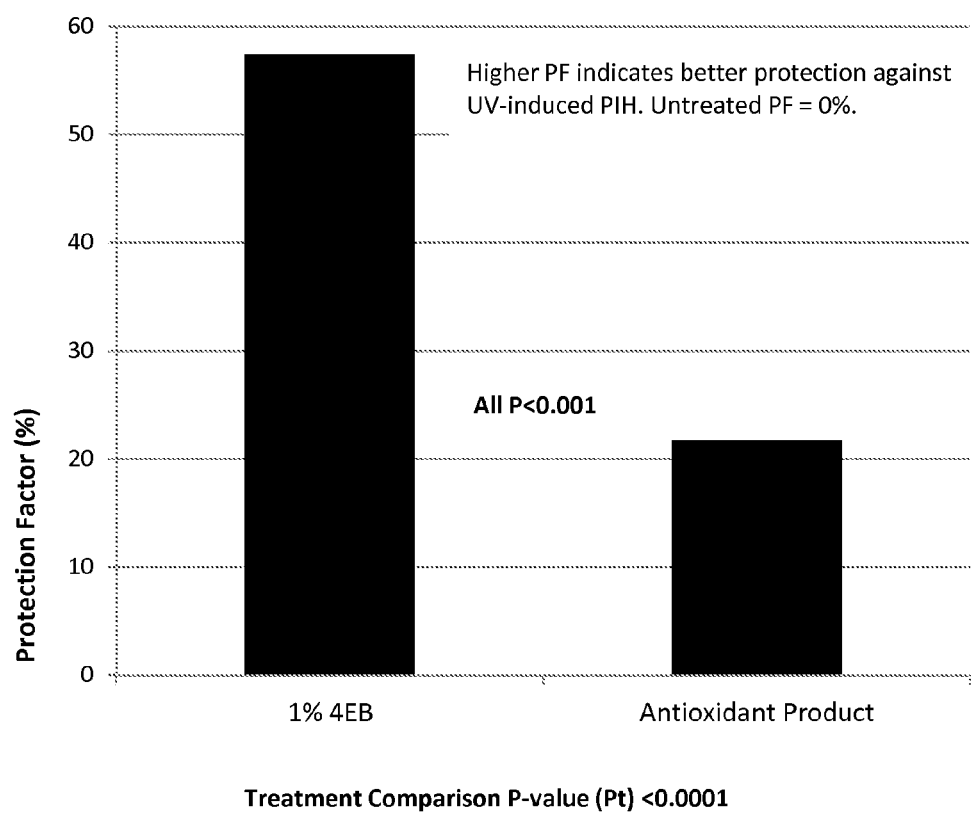
FIG. 2 is a graph depicting the protection factors assessed from the post-inflammatory hyperpigmentation clinical study.
Figure 3:
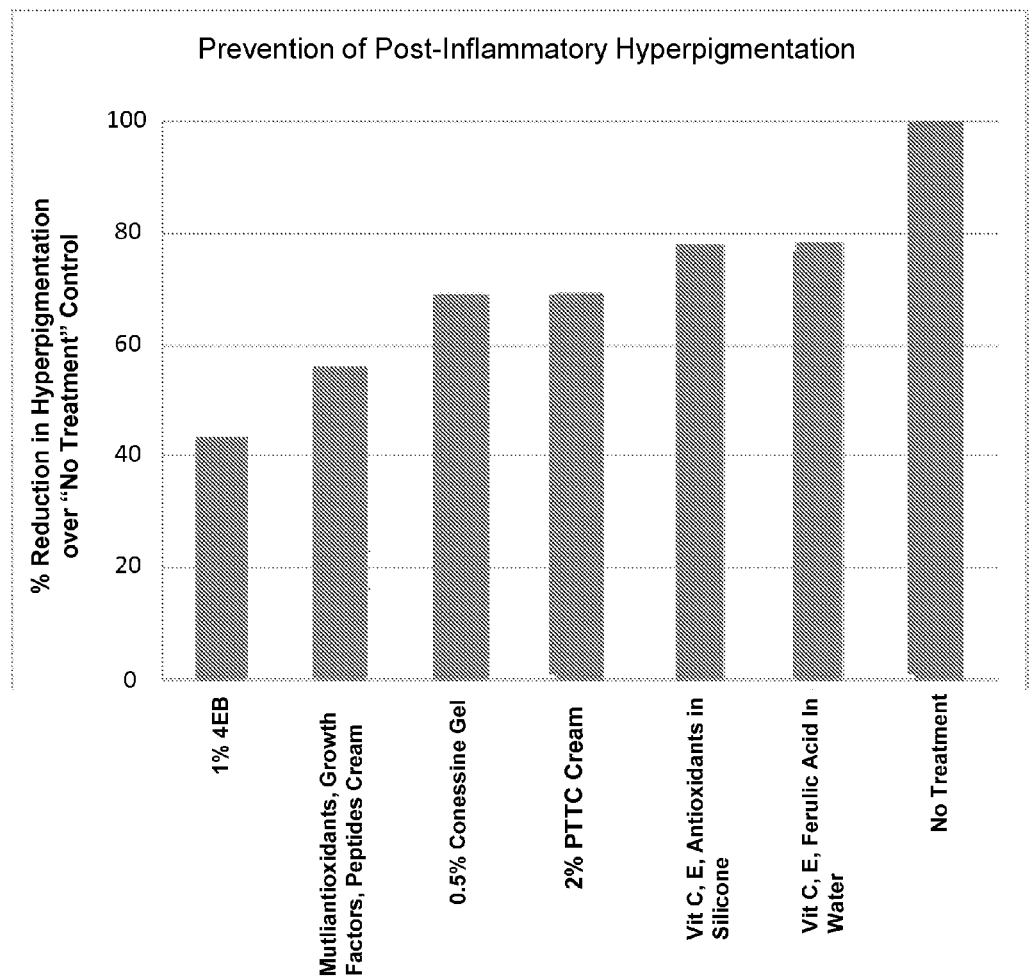
FIG. 3 is a graph depicting the reduction in hyperpigmentation assessed from the post-inflammatory hyperpigmentation clinical study.

Both the 1% 4EB product and the antioxidant product provided statistically significant protection from UV-induced erythema and post-inflammatory hyperpigmentation when compared to untreated control (all $P<0.01$). The 1% w 4EB composition provided significantly higher protection than the antioxidant product from UV-induced post-inflammatory hyperpigmentation (all $P<0.0001$, FIG. 2). The results from this clinical study suggest that topical 1% 4EB provides significant protection from UV-induced post-inflammatory hyperpigmentation when compared to the antioxidant product. The 1% w 4EB product provided a statistically significant reduction in hyperpigmentation (FIG. 3) and increase in skin brightness (FIG. 4) when compared to the untreated control sample and the other test products (all $P<0.0001$).

Figure 4:
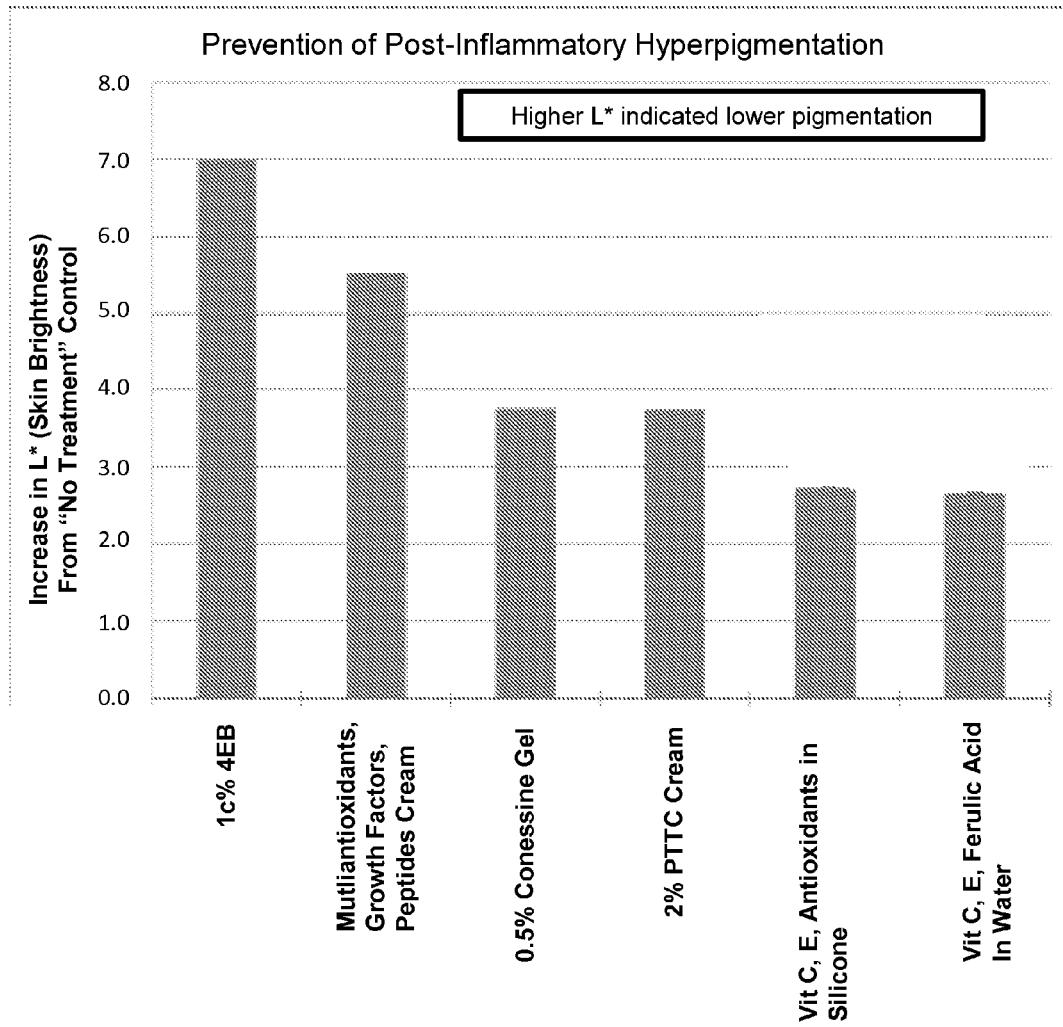
FIG. 4 is a graph depicting the increase in skin brightness (L*) assessed from the post-inflammatory hyperpigmentation clinical study.
Figure 5:
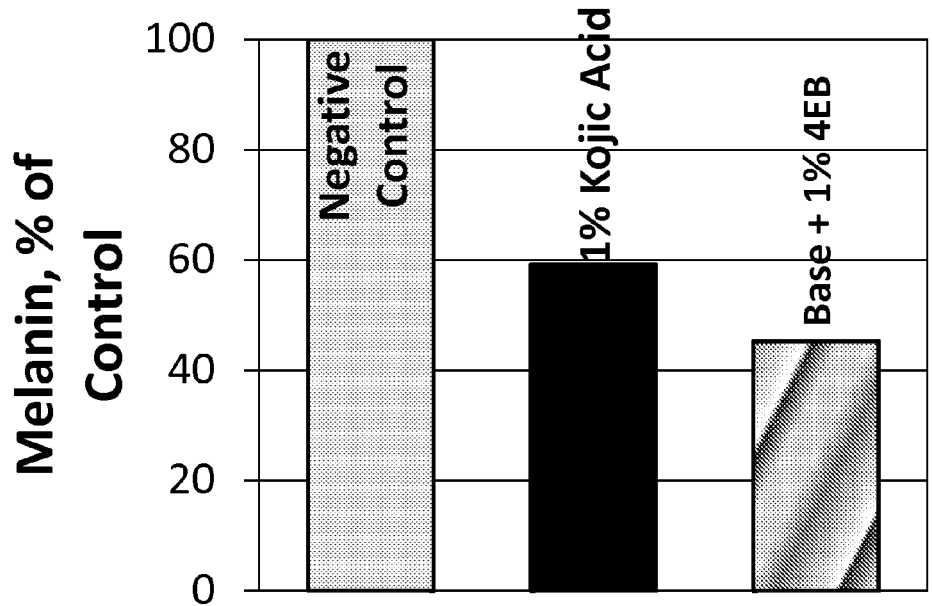
FIG. 5 is a graph depicting the reduction of melanin content in human skin equivalent treated with a negative control, positive control (1% Kojic acid) or Base+1% 4EB.

Results from this clinical study suggest that topical 1% 4EB may provide significant short-term and long-term protection from UV-induced post-inflammatory hyperpigmentation. The results depicted in FIG. 3 from the clinical study suggest that topical 1% 4EB provides a statistically significant reduction in hyperpigmentation when compared to the untreated control sample and the other test products (all $P<0.0001$). Additionally, as seen in FIG. 4, the 1% 4EB product provided a statistically significant increase in skin brightness when compared to the other test products (all $P<0.0001$).

Example 4

Topical Formulation

A mixture (Part A) of deionized water (69.30% by weight), glycerin-USP (3.00%), Glycereth-7 (2.50%), polyacrylamide (2.25%), and ethoxydiglycol (2.20%) was heated to 80° C. A separate mixture (Part B) of glyceryl stearate (5.00%), jojoba oil (3.00%), isocetyl stearate (3.25%), squalane (4.10%), cetyl ricinoleate (3.40%), 4-ethoxybenzaldehyde (1.00%), and phenoxyethanol (1.00%) was heated to 80° C. Part B was added to Part A with continuous mixing and stirring. The combined mixture was cooled to 30° C. with continuous mixing to yield a cosmetic or pharmaceutical composition.

Example 5

Topical Formulation

Stearyl alcohol and a white petrolatum is melted at about 75° C. and then a mixture of a compound of the invention, methylparaben, propylparaben, sodium lauryl sulfate, and propylene glycol were dissolved in water. The resulting mixture is stirred until it congeals.

Example 6

Topical Cream Formulation

To a commercial mineral oil-water cold cream base (100 gm) is added 0.75 grams of a compound of Formula I as a fine powder or liquid with continuous mixing and stirring to suspend the powder in the base and yield a cosmetic or pharmaceutical composition.

Example 7

Topical Cream Formulation

A cream composition containing 1% ethoxybenzaldehyde is formulated as follows. 1% ethoxybenzaldehyde (1% by weight), niacinamide (2% by weight), hydroquinone (2% by weight) is dissolved in propylene glycol (15 mL). The solution thus prepared is mixed with hydrophilic ointment, USP grade (85 gm) until a consistent cream is obtained.

Example 8

Topical Formulation

A therapeutic composition contain 1% ethoxybenzaldehyde and additional active agents is formulated as follows. Ethoxybenzaldehyde (1% by weight), niacinamide (2% by weight), and kojic acid (2% by weight) are dissolved in a mixture of ethanol (70 mL), water (10 mL) and propylene glycol until a clear solution is obtained.

Example 9

Tablet Formulation

A compound of Formula I is mixed with dry gelatin binder and starch diluent in a 0.1:1:1 weight ratio. A lubricating amount of magnesium stearate is added and the mixture is formed into 210 mg tablets containing 10 mg of the active substituted benzaldehyde.

Example 10

Capsule Formulation

A compound of Formula I is admixed as a dry powder with a starch diluent in an approximate 0.1:2 weight ratio. The mixture is filled into 210 mg capsules (10 mg of active compound per capsule).

Example 11

Transdermal Formulation

A compound of Formula I is admixed with a polymer matrix, a permeation enhancer and one or more other excipients. The formulation is place on a backing membrane.

Example 12

Exemplary Topical Formulation

An amount of 0.1-0.5% 4EB is admixed with 0.1-0.75% Retinol, 2.0-8.0% Niacinamide, 1.0-5.0% Tetrahexyldecyl Ascorbate, 0.001-0.5% Licorice root extract, 0.1-3.0% Resorcinol, and 0.1-3.0% ethyl linoleate and one or more other excipients.

Example 13

Half-Face Study to Assess the Efficacy and Tolerance of Four Topical Products in the Treatment of Facial Hyperpigmentation 1.0 Background Hyperpigmentation is an increase in pigmentation or color of the skin that is abnormally dark. Hyperpigmentation occurs when an excess amount of melanin is produced. Causes of hyperpigmentation include sun exposure, certain medications, hormonal changes, PIH (post inflammatory hyperpigmentation) or a congenital pigmentation disorder. Hyperpigmentation results in uneven skin color (tone) and a photoaged appearance. Dyspigmentation is identified as an abnormality in the formation or distribution of pigment, especially in the skin.

2.0 Purpose

This controlled clinical usage study will be conducted to evaluate and compare the tolerance and efficacy of four topical products designed to treat facial hyperpigmentation when used by females with moderate to severe dyspigmentation on the face.

Evaluations of efficacy will be made using clinical grading, Chroma Meter measurements, digital photography, and self-assessment questionnaires. Tolerance will be evaluated by clinical grading of objective irritation, subject assessment of subjective sensations, and monitoring of adverse events and reactions.

3.0 Assessments

The topical treatments will produce statistically significant improvements in clinical grading scores for efficacy parameters and have statistically non-significant changes objective irritation assessments after 12 weeks of use compared to baseline.

4.0 Study Endpoints 4.1 Primary Endpoints

Efficacy grading is conducted at baseline, week 4, week 8, and week 12. Efficacy grades is evaluated for statistical significance in: (1) changes from baseline (weeks 4, 8 and 12); and (2) comparisons to the other test products (weeks 4, 8 and 12).

Chroma Meter measurements are conducted at baseline, week 4, week 8, and week 12. Chroma Meter measurements are evaluated for statistical significance in: (1) changes from baseline (weeks 4, 8 and 12) and (2) comparisons to the other test products (weeks 4, 8 and 12). PL 4.2 Secondary Endpoints Self-assessment questionnaires are conducted at baseline, week 4, week 8, and week 12.

5.0 Test Material Information 5.1 Study Identification Procedures

Each study product(s) is assigned a unique test material identification number (TMIN) in order to provide proper identification in records and reports.

5.2 Study Product Description(s)

| Product Description | Code/Formula Number |
|---|---|
| Test Product #1 | Base + 0.5% 4EB + 0.1% Osthol |
| Test Product #2 | Base + 0.1% 4EB + 0.1% Osthol |
| Test Product #3 | Base + 0.5% 4EB |
| Test Product #4 | Hydroquinone 4% |

The base composition contains Retinol, Niacinamide, Tetrahexyldecyl Ascorbate, Licorice root extract, Resorcinol, and ethyl linoleate and a pharmaceutically/cosmetically acceptable carrier.

5.3 Method of Treatment Assignment

Subjects are numbered sequentially in the order in which they qualify for entry into the study.

Prior to the start of the study, the biostatistics department will generate a randomization list to establish treatment assignment. Subjects are assigned to use 2 of the 4 test materials according to a half-face design. One of the test materials is applied to the left side of the face and another test material is applied to the right side of the face, as determined by the randomization design. Randomization is based on a balanced incomplete block design with n=30 (approximately) for each treatment product.

All subjects are distributed a cleanser, moisturizer and sunscreen product to use throughout the study.

5.4 Instructions for Use

Sun exposure is to be avoided as much as possible. If sun exposure cannot be avoided, sunscreen SPF30 is to be re-applied to the facial skin prior to sun exposure.

It is important that the LEFT designated products are only applied on the LEFT side of your face, and the RIGHT designated products are only applied on the RIGHT side of the face.

In the morning and evening, the face is washed with the Facial Cleanser and gently patted dry.

Left Facial Side:

Using your LEFT hand, apply a thin amount of Test Product labeled LEFT onto your LEFT facial side only. Wait for product to absorb before applying moisturizer.

Using your LEFT hand, apply the provided Ultra Sheer Moisturizer onto your LEFT facial side.

Mornings only: using your LEFT hand, apply the provided All-Physical Sunscreen SPF30 to the LEFT side of face and throughout the day as needed.

Right Facial Side:

Using your RIGHT hand, apply a thin amount of Base Product labeled RIGHT onto your RIGHT facial side only. Wait for product to absorb before applying moisturizer.

Using your RIGHT hand, apply the provided Ultra Sheer Moisturizer onto your RIGHT facial side.

Mornings only: using your RIGHT hand, apply the provided All-Physical Sunscreen SPF30 to the RIGHT side of face and throughout the day as needed.

Avoid contact with eyes. If contact occurs, rinse thoroughly with water. If irritation or rash occurs, discontinue use and contact your doctor.

5.6 Treatment Blinding

The following procedures will be followed in order to maintain the double-blinded nature of this study and ensure appropriate evaluator blinding:

The study products will be dispensed by someone other than the investigator or other evaluator(s). Additionally, the person in charge of study product dispensation and the subject will be instructed not to discuss the study products with the Investigator or other evaluator(s).

The randomization list will be secured in a locked cabinet and/or computer file with restricted access to a data committee consisting of selected representatives from clinical services, quality assurance and the statistical department.

Subjects will not be made aware of treatment assignment.

Any study product that has a label indicating its identity will be covered and labeled as Test product #1, Test product #2, Test product #3 and Test product #4.

6.0 Subject 6.1 Number of Subjects

Sixty subjects meeting the eligibility requirements are expected to complete participation in the clinical trial. Each subject will use 2 of the 4 test materials, so that each test material will be used by approximately 30 subjects.

6.2 Informed Consent Agreement

An IRB approved informed consent agreement, consistent with the requirements in 21 CFR §50.25, is given to each subject before the start of this study according to standard procedures. Subjects are ineligible to participate in this study without a signed informed consent.

6.3 Subject Identification

Subjects are assigned a three-digit number which, when used in conjunction with the clinical study number, uniquely identifies every subject on the study. This number remains with the subject throughout the study and should be used in all references to the individual in this study. No number is reassigned once the study begins.

6.4 Eligibility Criteria

Individuals are admitted to study at the discretion of the Investigator or designated, and based on medical history and findings of the pre-study interview and examination. Individuals are screened for the eligibility criteria listed below prior to study enrollment.

Inclusion Criteria: a subject is eligible to participate if they meet all of the following inclusion criteria:

1. Females, between the ages of 30 and 65 years
2. Fitzpatrick skin type I-IV
   The Fitzpatrick skin classification is based on the skin's unprotected response to the first 30 to 45 minutes of sun exposure after a winter season without sun exposure. The categories of skin types are as follows:
   I. Always burns easily; never tans
   II. Always burns easily; tans minimally
   III. Burns moderately; tans gradually
   IV. Burns minimally; always tans well
   V. Rarely burns; tans profusely
   VI. Never burns; deeply pigmented
3. Presence of clinically determined moderate to severe dyspigmentation on the face as determined by a score of 4-9 from the Overall Hyperpigmentation scale.
4. Willing and able to provide informed consent and to cooperate and participate by following study requirements for the duration of the study and to report any adverse event symptoms immediately
5. Good general health and free of any disease state or physical condition (e.g., psoriasis, moderate to severe rosacea, hirsutism, scars, tattoos, etc.) which might impair evaluations of the test sites or increase the health risk to the subject by study participation.
6. Willingness to cleanse the face and remove all makeup at least 20 minutes prior to each scheduled clinic visit. No other topical products should be applied to the face until the study visit has been completed.
7. Individuals who have not used systemic retinoids (e.g., Tazorac, Soriataine, Accutane, etc.) and/or any other systemic medication known to affect melasma at least 60 days prior to the study entry and will not use these products throughout the duration of the study
8. Individuals who have not used topical retinoids and/or all other topical medication(e.g., topical steroids, products containing benzoyl peroxide, alpha- or beta-hydroxy acids, hydroquinone, and/or any other OTC skin treatment medications) to the facial area known to affect melasma at least 14 days prior to study entry and will not use these products throughout the duration of the study.
9. Willingness to not use any other skin lightening products for the duration of the study. Subjects may continue to use regular cosmetic products (as long as they meet inclusion criteria #7 and #8), but may not begin the use of any new facial products other than the provided materials for the duration of the study. Regular use is defined as products used for a minimum of one month prior to enrollment without any incidence of irritation.
10. If subjects are taking hormone replacement or hormones for birth control, then they must be willing not to stop or change this medication for the duration of the study. Individuals who are not taking hormones at the start of the study must be willing not to start their use during the course of the study.
11. Women of childbearing potential must be willing to use a medically proven method of birth control for the duration of the study.
12. Willingness to avoid extended periods of sun exposure for the duration of the study (including tanning beds), especially from 10 AM to 2 PM. If brief (less than 20 minutes) periods of sun exposure cannot be avoided, then subjects are asked to use an SPF 30 product and wear protective clothing prior to and during exposure. Any extended sun exposure must be recorded on the diary.
13. Willingness to have facial exams and digital photos performed on the face.

Exclusion Criteria: a subject will not be eligible to participate if they meet any of the following exclusion criteria:

1. Individuals with known allergies or sensitivities to skin lightening products, retinoids, hydroquinone, sulfites, moisturizers, or other facial products.
2. Individuals with active symptoms of allergy, active psoriasis or eczema, sunburn, excessive scarring, tattoos, or other skin condition in the test areas that would interfere with the assessments of this study.

-continued

3. Individuals who are nursing, pregnant, or planning to become pregnant during the study.
4. Uncontrolled disease such as diabetes, hypertension, hyper or hypo-thyroidism, active hepatitis, immune deficiency, or autoimmune disease as determined by the initial paperwork.
5. Individuals who have a pre-existing or dormant dermatologic condition (e.g., psoriasis, atopic dermatitis, advanced skin cancer, rosacea, acne vulgaris, atopic dermatitis, discoid lupus erythematosus, fixed drug eruption, general drug eruption, idiopathic eruptive macular pigmentation, impetigo, vitiligo, insect bites, irritant and allergic contact and photocontact dermatitis, lichen planus, lichen simplex chronicus, morphea, pityrasis rosea, polymorphous light eruption, psoriasis, etc.)
6. Individuals who require electrolysis, waxing, or use depilatories on the face during conduct of the study.
7. Individuals who have had a facial peel or a laser treatment of the face within 60 days prior to the start of the study.
8. Subjects who participated on another facial usage study within the last 30 days, or who are currently participating on another usage study.
9. Subjects currently on or planning to participate on any type of research study at another facility or a doctor's office during this study.

Individuals are admitted to study at the discretion of the Investigator or his/her designate based on medical history and findings of the pre-study interview and examination.

7.0 Study Design
7.1 Description

This controlled clinical usage study is conducted to evaluate and compare the efficacy and tolerance (safety) of the 4 test materials in improving the clinical signs of facial skin hyperpigmentation. The study is conducted over the course of 12 weeks and will consist of 4 visits, at baseline, week 4, week 8, and week 12.

Women with clinically determined dyspigmentation of the facial skin are recruited for this study. Subjects will use 2 of the 4 test materials according to a half-face design, as assigned by a randomization schedule. Test material evaluations are conducted using clinical grading, bioinstrumentation (Chroma Meter measurements), digital photography, and self-assessment questionnaires.

7.2 Outline of Procedures 8.2 Visit 1: Baseline

Candidate subjects are screened for qualifying criteria. Subjects that pass the screening are assigned a screening number and graded for the remaining efficacy evaluations and tolerance (safety) evaluations as outlined in Sections 9.1 and 9.2.

Candidate subjects will complete an Eligibility and Health Questionnaire, a Confidentiality Agreement and a HIPAA form. Those who pass eligibility requirements are enrolled into the study and assigned a subject number.

Those who qualify will be enrolled in the study and assigned a subject number.

Subjects will have Chroma Meter measurements and digital photography procedures performed as described in Sections 9.3 and 9.4. Subjects will complete a self-assessment questionnaire as described in Section 9.5.

Subjects are distributed pre-weighed units of 2 of the test materials, according to a randomization design. One of the

| Procedures: | Visit 1 Baseline | Visit 2 Week 4 | Visit 3 Week 8 | Visit 4 Week 12 |
|---|---|---|---|---|
| Qualification screening (facial exam) and eligibility paperwork | X | | | |
| Clinical evaluations on the right and left sides of the face by Expert Grader: Efficacy Parameters: overall hyperpigmentation, investigator's global assessment, global improvement Tolerance Parameters: objective and subjective irritation (erythema, scaling, burning/stinging, itching, tightness, tingling) | X | X | X | X |
| Chroma Meter measurements on the right and left sides of the face of a hyperpigmented area | X | X | X | X |
| Full-face Right and Left face digital images (cross polarized and standard lighting) using VISIA CR | X | X | X | X |
| Subject Self-assessment Questionnaire completed by subjects regarding various skin condition parameters for the right and left sides of the face | X | X | X | X |

8.0 Conduct of Study
8.1 Pre-Study Procedures

Candidate subjects are screened with the eligibility requirements by telephone prior to Visit 1.

Candidate subjects are instructed to wash their faces and remove all makeup at least 20 minutes prior to arrival at the clinic of the baseline visit.

Candidate subjects are assigned an appointment time for visiting the clinic.

test materials is applied to the right side of the face and the other test material is applied to the left side of the face. Test material units are clearly labeled as "Left" and "Right". Subjects are also distributed a cleanser, moisturizer and sunscreen to use throughout the study.

Usage instructions are discussed with subjects and written usage instructions are provided. Subjects are also provided with a calendar of study visits and a daily diary to record test material application times and comments.

8.3 Visit 2: Week 4 and Visit 3: Week 8

A clinician records concomitant medications and asks subjects if they have experienced any changes in their health since the last visit.

Daily diaries are collected and reviewed for compliance. Subjects that are non-compliant are counseled that if they continue to be non-compliant they will be dropped from the study. New diaries are distributed as needed.

Subjects participate in the following procedures: efficacy evaluations as described in Section 9.1; tolerability evaluations described in Section 9.2; Chroma Meter measurements as described in Section 9.3; and digital photography as described in Section 9.4. Subjects will complete a self-assessment questionnaire as described in section 9.5.

8.4 Visit 4: Week 12

A clinician records concomitant medications and asks subjects if they have experienced any changes in their health since the last visit.

Daily diaries will be collected and reviewed for compliance.

Subjects participate in the following procedures: efficacy evaluations as described in Section 9.1; tolerability evaluations described in Section 9.2; Chroma Meter measurements as described in Section 9.3; and digital photography as described in Section 9.4. Subjects will complete a self-assessment questionnaire and a final product evaluation questionnaire as described in section 9.5.

9.0 Assessments 9.1 Efficacy Evaluations

At baseline, week 4, week 8, and week 12, an expert clinical grader evaluates subjects on the right and left sides of the face for the following efficacy parameters using the indicated grading scales (half-points may be used for all scales below to better describe a condition):

| Overall Hyperpigmentation | |
|---|---|
| 0 | None |
| 1 to 3 | Mild |
| 4 to 6 | Moderate |
| 7 to 9 | Severe |

Subjects will be required to have a score of 4 to 9 for overall hyperpigmentation on both sides of the face to qualify for study participation.

Investigator's Global Assessment-Hyperpigmentation:

| Score | Rating | Description |
|---|---|---|
| 0 | Clear | No brown spots or areas of discoloration |
| 1 | Almost clear | Overall there are a few brown spots with increased pigmentation; they are very small in size and only very slightly darker than surrounding skin |
| 2 | Mild | Several brown spots with increased pigmentation; they are small in size and slightly darker than surrounding skin |
| 3 | Moderate | Many brown spots with increased pigmentation; they are medium in size and much darker than surrounding skin |
| 4 | Severe | Many large brown spots with increased pigmentation; they are large in size and markedly darker than surrounding skin |

Investigator's Global Improvement Assessment:

| | |
|---|---|
| 1 | Worse |
| 2 | No Improvement |
| 3 | Mildly Improved |
| 4 | Moderately Improved |
| 5 | Markedly Improved |

9.2 Tolerability Evaluations

At baseline, week 4, week 8, and week 12, the following tolerance/safety parameters are scored on the right and left sides of each subject's face:

| | |
|---|---|
| Objective parameters (clinically graded) | erythema, scaling |
| Subjective parameters (assessed by subjects) | burning/stinging, itching, tightness, tingling |

Results of the tolerance assessments will be recorded using the following scale (with half-point scores used as necessary):

| | |
|---|---|
| 0 | None |
| 1 | Mild |
| 2 | Moderate |
| 3 | Severe |

9.3 Chroma Meter Measurements

The Minolta Chroma Meter CR-400, in conjunction with a computer, is used to instrumentally assess skin color. The following values are recorded:

| | |
|---|---|
| $L^*$ | Values describe the relative brightness on a gray scale from black to white; scores increase as the skin tone becomes brighter |
| $a^*$ | Values describe the color hue ranging from red to green; scores increase with vascularization or blood flow |
| $b^*$ | Values describe the color hue ranging from blue to yellow; scores increase with the amount of melanin in the skin |

Chroma Meter measurements are performed at baseline, week 4, week 8, and week 12. A single measurement is taken on the right and left sides of each subject's face on a hyperpigmented area selected by the expert grader. The location is recorded on a facial diagram to ensure consistency in measurement location at each visit.

9.4 Digital Photography

Digital photography using a Nikon camera (Canfield VISIA-CR Camera System) is performed at baseline, week 4, week 8, and week 12, to document visible changes in facial hyperpigmentation. For each subject, a full-face image is taken of the right and left sides of the face (2 images per subject) with standard and cross-polarized lighting/filter conditions. The focus revolves around the brown channel images (derived from the cross-polarized images) and the standard lighting photos.

Photos taken at weeks 4, 8 and 12 are compared to the baseline photo to ensure consistent focus, lighting, placement and color. At each photography visit, color standards are photographed prior to beginning each day's photography.

9.5 Self-Assessment Questionnaires

At baseline, week 4, week 8, and week 12, subjects will complete a self-assessment questionnaire regarding various skin condition parameters on the right and left sides of the face.

10.0 Adverse Events 10.1 Definition of an Adverse Event

An adverse event (AE) is any untoward medical occurrence in a clinical investigation where a subject is administered a pharmaceutical product/biologic (at any dose), OTC, cosmetic product or medical device and which does not necessarily require a causal relationship with a test article. An AE can therefore be any unfavorable and unintended sign (including an abnormal laboratory finding, for example), symptom or disease temporally associated with the use of a medicinal product whether or not considered related to the medicinal product. Adverse events will be recorded on the appropriate case report forms and source documents.

10.2 Assessment of Severity and Relationship

The investigator or his medical staff will evaluate all adverse events as to their severity and relation to the test article. The severity of adverse events will be graded as follows:

| | |
|---|---|
| Mild: | Awareness of a sign or symptom but easily tolerated |
| Moderate: | Discomfort sufficient to cause interference with usual activity or to affect clinical status |
| Severe: | Incapacitating with inability to do usual activity or to significantly affect clinical status |

Assessment of Causality: the Investigator and/or trained staff member will also assess the relationship of any adverse event to the use of the study article, based upon available information, using the following guidelines:

| | | |
|---|---|---|
| 0 | Unlikely | No temporal association, or the cause of the event has been identified, or the test article cannot be implicated |
| 1 | Possible | Temporal association, but other etiologies are likely to be the cause; however, involvement of the test article cannot be excluded |
| 2 | Probable | Temporal association, other etiologies are possible, but not likely |
| 3 | Definite | Clear-cut temporal association |

10.3 Definition of a Serious Adverse Event (SAE)

A serious adverse event is any experience or reaction occurring at any dose that results in any of the following outcomes: death, is life threatening, inpatient hospitalization or prolongation of hospitalization, a persistent or significant disability/incapacity, or a congenital anomaly/birth defect.

Important medical events that may not result in death, be life-threatening, or require hospitalization may be considered a serious adverse event when, based upon appropriate medical judgment, they may jeopardize the patient or subject and may require medical or surgical intervention to prevent one of the outcomes listed in this definition. The term "life-threatening" refers to an event in which the subject was at risk of death at the time of event; it does not refer to an event that hypothetically might have caused death if it was more severe.

Hospitalization solely for the purpose of diagnostic tests, even if related to an adverse event, elective hospitalization for an intervention which was already planned before the inclusion of the subject in the study, and admission to a day-care facility may not themselves constitute sufficient grounds to be considered as a serious adverse event. Hospitalization is defined as being admitted to a hospital as an in-patient for greater than 24 hours.

10.4 Procedures for Reporting Adverse Events

At each visit, the subjects are questioned about adverse events using an open question (e.g., "Have you noticed any change in your health since the last visit?").

Directed questioning and examination will be performed when appropriate. All reported adverse events are documented on the appropriate forms without omitting any requested and known information. Every time a concomitant therapy is reported during the study, an Adverse Event Form will be completed if appropriate and the reason for the treatment noted.

When an adverse event persists at the end of the study, the investigator conducts a follow-up of the subject until the event is satisfactorily resolved.

All adverse events are recorded by the Investigator onto the Adverse Event page of the source documents describing the adverse event, onset and stop date, severity, opinion of causality, the course of action taken, if any, as well as any pertinent data necessary to allow a complete evaluation of the adverse event. For serious adverse events, an additional report (SAE Report Form) is completed.

10.5 Procedures for Reporting Serious Adverse Events

Any serious adverse event that occurs during the study whether related to the treatment or not, expected or not, is reported.

10.6 Unanticipated Adverse Events

Unanticipated adverse effect is defined as any serious adverse effect on health or safety, any life-threatening problem or death caused by, or associated with, the test article if that effect, problem, or death was not previously identified in nature, severity, or degree of incidence in the application; or any other unanticipated serious problem associated with the test article that relates to the rights, safety, or welfare of subjects.

10.7 Anticipated Reactions

The test material when applied to the face may produce mild to moderate, transient erythema, dryness, burning, stinging and/or itching. The responses discussed above will not be treated as adverse reactions. These conditions may or may not resolve over time. Symptoms that are persistent and moderate to severe in nature, or that involve elevation (e.g., edema, papules, vesicles, spreading) are considered adverse events (AEs).

11.0 Biostatistics and Data Management

Statistical Analysis

The per protocol (PP) population is the primary population for efficacy and tolerance testing. The PP population includes all subjects who were randomized and completed all study procedures. Clinical grading scores and Chroma Meter measurement values at week 4, week 8, and week 12 are compared to baseline scores/values using a paired t-test. The average percent change from baseline is calculated for all parameters at each post-baseline time point. Comparisons among the three test materials are performed using analysis of variance (ANOVA) with paired comparisons using Fisher's Least Significant Difference (LSD). All differences are considered to be statistically significant at the $p<0.05$ level.

Subject Self-assessment questionnaires regarding skin condition parameters completed by subjects at all visits are analyzed using descriptive statistics presenting the percentages for each question.

Data Management

Clinical grading and Chroma Meter measurements are performed using electronic data capture system (EDC) which documents the identity of the evaluator as well as the time and date of all entries, or all corrected entries.

The electronic data capture system (EDC) is a computerized system designed for the collection of clinical data in electronic format. The 3 major aspects of EDC are a graphical user interface for data entry, a validation component to check for user data and a reporting tool for analysis of the collected data. Statistical analyses are performed using SAS software version 9 series (SAS Statistical Institute).

The self-assessment questionnaires are completed by subjects electronically using HIPAA compliant Zoomerang online survey software.

Data review and analyses is performed by an independent data committee. The data committee will consist of selected representatives from clinical services, quality assurance and the statistical department.

12.0 Results

Figure 7:
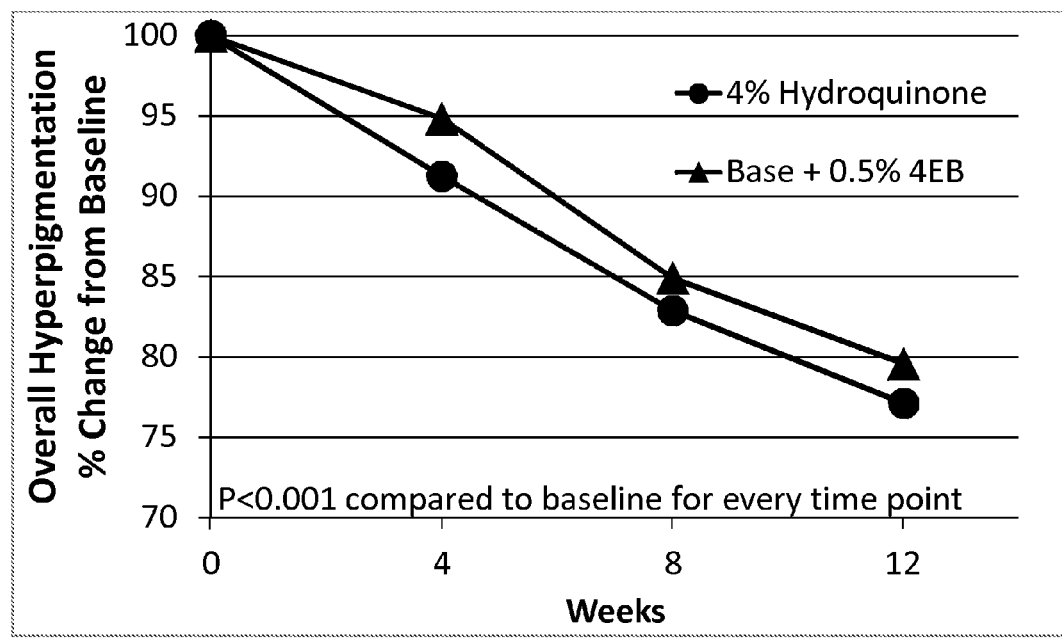
FIG. 7 is a graph depicting the decrease in hyperpigmentation compared to baseline after treatment with 4% hydroquinone or Base+0.5% 4EB.
Figure 8:
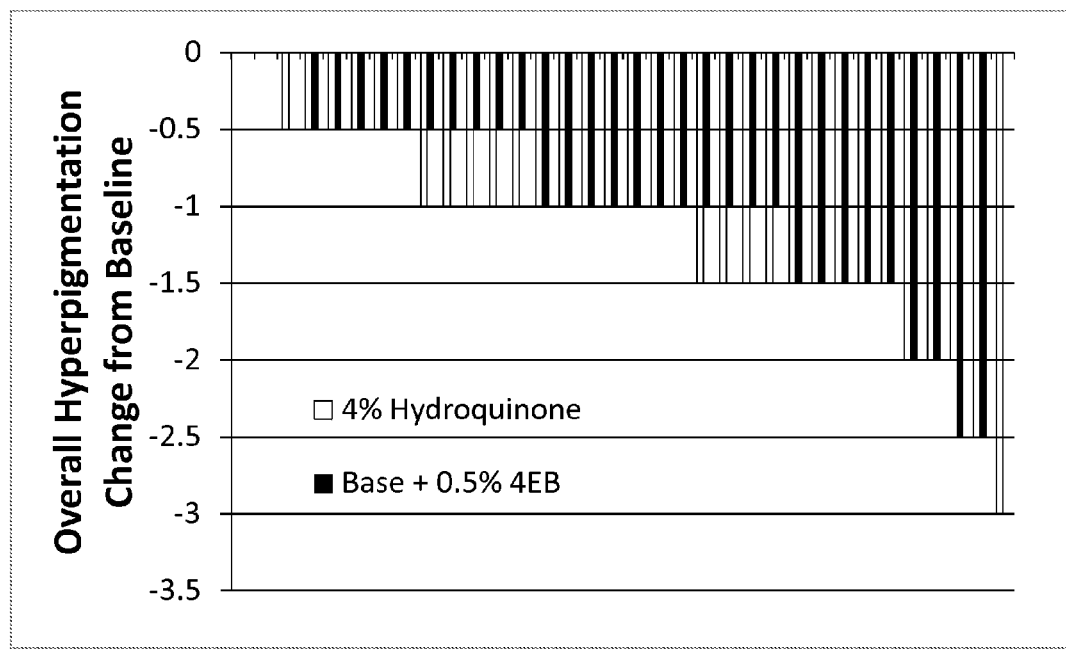
FIG. 8 is a graph depicting the distribution of results in individual subjects after treatment with 4% hydroquinone or Base+0.5% 4EB.
Figure 9:
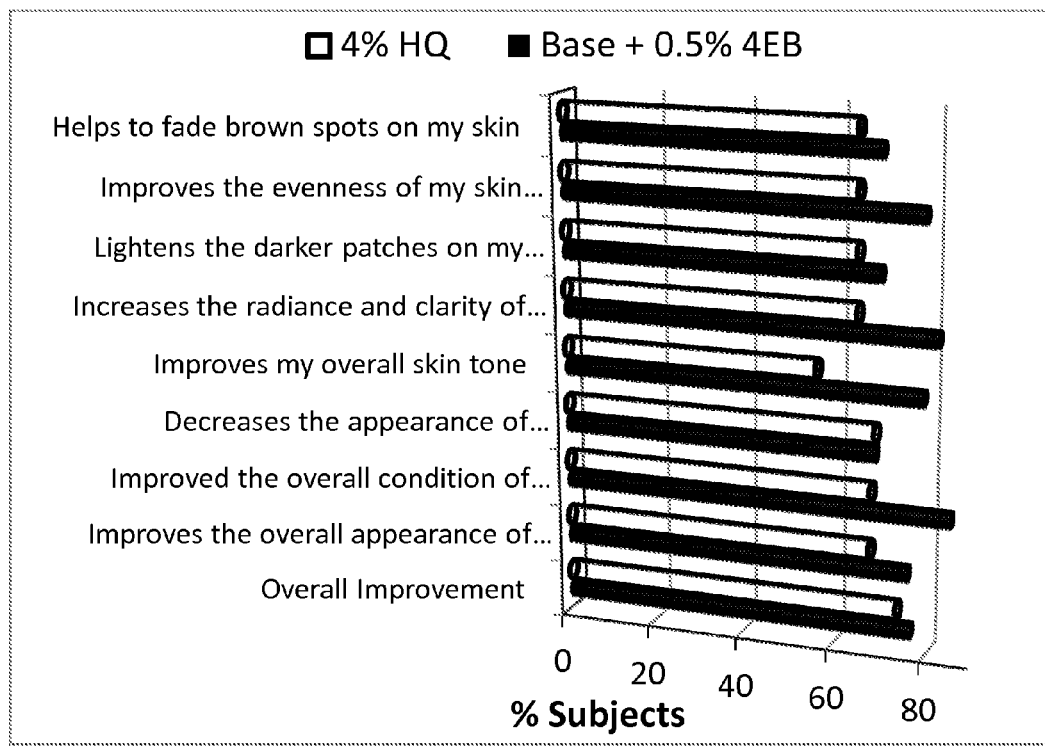
FIG. 9 is a graph depicting the results from the patient self-assessment questionnaire after treatment with 4% hydroquinone or Base+0.5% 4EB.

FIGS. 7, 8 and 9 provide the results from this study. Overall, 4% hydriquinone and Base+0.5% 4EB both significantly reduced hyperpigmentation compared to baseline for every time point (See FIG. 7).

FIG. 8 illustrates the overall level of hyperpigmentation as a change from baseline. Sites treated with 4% hydriquinone and Base+0.5% 4EB demonstrated comparable distribution of results in individuals.

FIG. 9 provides the results of the patient self-assessment questionnaires. Better subject preference was observed with treatment with Base+0.5% 4EB than with 4% Hydroquinone.

Example 14

An Open Application Trial Evaluating the Efficacy of Six Topical Whitening Formulations to UVR Induced Tanning 1.0 Background The following example examines acute exposure to ultraviolet radiation (UVR) stimulates melanogensis resulting in skin darkening, or hyperpigmentation.

2.0 Purpose

This study evaluates the effectiveness of six (6) test materials to reduce UV-induced tanning (hyper pigmentation) after receiving varying doses of UVR using a post-exposure regimen.

3.0 Assessment

The topical formulations being tested will protect human skin from the harmful effects of ultraviolet (UV) radiation compared to an untreated site as measured by changes in colorimetry ("L* and b*" values, or degree of tanning according to the International Commission on Illumilation (CIE) color standard).

4.0 Endpoints

Primary Endpoint: Significant changes in L* values compared to the untreated area Secondary Endpoint: Significant changes in b* values compared to untreated area, 5.0 Test Material Information 5.1 Study Identification Procedures Each study product(s) is assigned a unique test material identification number (TMIN) in order to provide proper identification in records and reports.

5.2 Study Product Description(s)

|                 | Product Description                |
| --------------- | ---------------------------------- |
| Test Product #1 | Base                               |
| Test Product #2 | Base + 1% 4EB                      |
| Test Product #3 | Base + 0.5% 4EB                    |
| Test Product #4 | Base + 1% 4EB + 0.2% DSE extract   |
| Test Product #5 | Base + 1% 4EB + 0.1% Osthol        |
| Test Product #6 | 4% hydroquinone                    |

The base composition contains Retinol, Niacinamide, Tetrahexyldecyl Ascorbate, Licorice root extract, Resorcinol, and ethyl linoleate and a pharmaceutically/cosmetically acceptable carrier.

5.3 Method of Treatment Assignment

Subjects are numbered sequentially in the order in which they qualify for entry into the study.

Prior to the start of the study, the biostatistics department generates a randomization based on a site rotational basis to avoid skin site bias. The irradiated, untreated site is to be included in the randomization assignment.

UV Radiation

UV radiation is supplied by an artificial source, which has a spectral output in the ultraviolet range comparable to that of the natural solar spectrum (UVB: 290-320 nm and UVA: 320-400 nm). The artificial light source used complies with the source spectral specifications as described in published testing guidelines. UV irradiation is performed with a single port solar simulator (Model 16S, Solar UV Simulator, Solar Light Co., Philadelphia) with a 150 watt xenon arc lamp. UVB+UVA radiation is obtained by using a combination of the UG-11/1 mm and WG-320 filters (Schott Glass Technologies) that are placed in the radiation path of the solar simulator.

An adjustable patient stop is used to keep the distance from solar simulator to the radiated surface constant. At a distance of approximately 6.5 cm from the lamp housing, the radiated surface is exposed to a 1.0 cm diameter spot of UVA/UVB light. Exposures are performed by varying the time of exposure (in seconds) while keeping the energy level constant. Opening and closing of the light shutter is performed manually. The radiation output of the xenon bulb is measured using the 3D-600 meter (Solar Light Co.). If a different radiometer is used for determination of radiation output, then a description of the model and accessories is included in the report. The xenon arc lamp is ignited and left on for at least 10 minutes prior to use in the study. Measurements are taken after lamp warm-up.

5.4 Product Application

Thirty (30) microliters (μl) of each test material is applied to designated sites using an open application technique with rubbing.

One irradiated, untreated site does not receive product application.

6.0 Subject Enrollment

Number of Subjects

Fifteen (15) subjects meeting the eligibility requirements are expected to complete participation in the clinical trial.

Informed Consent Agreement

An informed consent agreement, consistent with the requirements in 21 CFR §50.25, is given to each subject before the start of this study according to standard procedures.

Subject Identification

Subjects are assigned a three-digit number which, when used in conjunction with the clinical study number, uniquely identifies every subject on the study. This number remains with the subject throughout the study and is used in all references to the individual in this study. No number is reassigned once the study begins.

Eligibility Criteria

Individuals are admitted to study at the discretion of an Investigator or designated, and based on medical history and findings of the pre-study interview and examination. Individuals are screened for the eligibility criteria listed below prior to study enrollment.

| | Inclusion Criteria |
|---|---|
| 1 | Age: 18 years or older |
| 2 | Gender: Male or female |
| 3 | Fitzpatrick skin type III |
| | The Fitzpatrick skin classification is based on the unprotected response of the skin to the first 30 to 45 minutes of sun exposure after a winter season without sun exposure. The categories of skin types are as follows: |
| | I. Always burns easily; never tans |
| | II. Always burns easily; tans minimally |
| | III. Burns moderately; tans gradually |
| | IV. Burns minimally; always tans well |
| | V. Rarely burns; tans profusely |
| | VI. Never burns; deeply pigmented |
| 4 | General good health as determined by review of the health and eligibility questionnaire. |
| 5 | Willingness to cooperate and participate by following study requirements for the duration of the study and to report any adverse symptoms immediately. |

| | Exclusion Criteria |
|---|---|
| 1 | Individuals with Fitzpatrick skin types I, II, IV, V and VI. |
| 2 | Individuals that have been instructed by a physician, pharmacist, or health professional to avoid sunlight because of a medical condition and/or because of drug contraindications (see exclusion #10). |
| 3 | Individuals with known abnormal responses to sunlight or UVR light sources. |
| 4 | Individuals with a known allergy to any ingredient in a personal care product. |
| 5 | Individuals with known atopic skin diseases or neurodermatitis. |
| 6 | Women known to be pregnant, nursing, or planning to become pregnant within 6 months. |
| 7 | Individuals known to be treated for cancer or have a history of cancer. |
| 8 | Individuals with observable sunburn, suntan, scars, uneven tone/pigmentation, nevi or other dermal conditions on the test areas that might influence the test results. |
| 9 | Any disease or condition that the examining Investigator deems inappropriate for participation (e.g., uncontrolled high blood pressure, individuals with dermal hypersensitivity requiring treatments with medications in exclusion #10, etc.). |
| 10 | Individuals taking medication(s) which in the opinion of the Investigator, would interfere with the subject's participation on the study. Such medications include (but are not limited to) antihypertensive agents (hydrochorothiazide, furosemide, meticrane), ataractics (e.g., perphenazine), psychotropic agents (e.g., chlorpromazine), antihistamines (e.g., promethazine hydrochloride), oral hypoglycemic agents (e.g., tolbutamide, chlorpropamide), and tetracycline antibiotics (e.g., dimethylchloroteteacycline, tetracycline). |

Individuals are admitted to the study at the discretion of the Investigators based on medical history and findings of the pre-study interview and examination. Each subject is expected to complete the full course of the study.

7.0 Study Design

Description

This open application clinical study is conducted to evaluate the effectiveness of six (6) test materials to suppress the development of skin pigmentation after receiving varying doses of UVR using a pre-exposure/post-exposure regimen. Procedures are conducted as outlined in the table of procedures.

Outline of Procedures

| | Visit 1 Day 1 | Visit 2 Day 2 | Off Days 3-7, 14, 21, 28 and 35 | Visits 3, 7, 10, 13, 15, 18, 21, 24, 27 Days 8, 12, 16, 19, 22, 25, 29, 32, 36 | Visits 3-26 Days 8-13, 15-20, 22-27, 29-34 | Visit 27 Day 36 |
|---|---|---|---|---|---|---|
| Paperwork and Screening | X | | | | | |
| MED Determination | X | | | | | |
| Grade MED | | X | | | | |
| 1.0, 1.5, 2.0 and 2.5 MED Exposure | | X | | | | |
| Test Material Application | | | | | X | |
| Chromameter | | | | X* | | X |
| Photography | | | | X* | | X |

*Photography and Chromameter is done prior to test material application.

8.0 Conduct of Study 8.1 Visit 1: Baseline: Day 1

Individuals are given an informed consent (IC) document to read. They have all of their study related questions answered by the Investigator or his/her designated staff and if they agree, they sign two copies of the IC.

Subjects complete a health and eligibility questionnaire, a confidentiality agreement-photographic release form, and a HIPAA release form.

The Investigator or his/her designated staff examine the back (test site area) for evenness of skin tone (Fitzpatrick skin type III only) and to ensure the lack of uneven suntan, sunburn, scars, birthmarks, moles, vitiligo, keloids, skin abnormalities, or any other dermal markings.

Eligible individuals are enrolled into the study and assigned a subject number.

Subjects receive 5-7 irradiation exposures expressed as J/sq cm (adjusted to the erythema action spectrum) on adjacent unprotected skin sites on the lower back. Each exposure represents a 25% increase in energy over the previous exposure.

Seven (7) 3.0 cm×5.0 cm areas are marked on the lower back.

8.2 Visit 2: Day 2

1. Test sites from Visit 1 are examined using either a tungsten or warm white fluorescent light that provides 450 to 550 lux of illumination.
2. Sites are scored for erythema using the scale outlined in section 9.1 for MED Determination.
3. Using the determined MED value, UVR exposures are calculated. The amount of UVR delivered to each subject's test sites depends on this value.
4. Each area is exposed to UVR in doses of 1.0×, 1.5× and 2.0× and 2.5× the previously determined MED.
5. Subjects have a rest period of 5 days while tanning develops at the irradiated sites. Subjects resume study procedures on Day 8.

8.3 Visits 3, 7, 10, 13, 15, 18, 21 & 24: Days 8, 12, 16, 19, 22, 25, 29 & 32

Digital photography will be conducted as outlined in section 9.3

Chromameter measurements will be conducted as outlined in section 9.2

Test Materials are applied as outlined in Section 5.4. A seventh site serves as an irradiated untreated control.

8.4 Visits 4-6, 8, 9, 11, 12, 14, 16, 17, 19, 20, 22, 23, 25 & 26: Days 9-11, 13, 15, 17, 18, 20, 23, 24, 26, 27, 30, 31, 33 & 34

Test Materials will be applied as outlined in Section 5.4. A seventh site will serve as an irradiated untreated control.

8.5 Visit 27: Day 36

Digital photography are conducted as outlined in section 9.3 and chromameter measurements are conducted as outlined in section 9.2

9.0 Assessments

9.1 MED Determination Scoring

| | |
|---|---|
| − | no visible erythema |
| ? | questionable response; unclear |
| + | erythema, extending to the borders |
| ++ | erythema, with or without edema present |

The site receiving the lowest dose of combined UV that produced mild redness reaching the borders of the site will receive a score of +, and will be recorded as the MED (US) for that subject.

Each subject's MED may be different, but will likely be approximately 70 mJ/cm2. The intensity of UVR delivered to each subject's test sites depends on this value.

9.2 Chromameter Measurements

The Minolta Chroma Meter CR-400, in conjunction with a computer, is used to assess skin color. L* values describe the relative brightness on a gray scale from black to white, and scores increase as the skin tone becomes brighter/lighter. b* values describe the color hue ranging from blue to yellow and scores increase with the amount of melanin in the skin. One measurement is taken at each of the six treated sites and the untreated irradiated control site.

9.3 Imaging Procedures

Digital photography is performed on the six treated sites and the untreated irradiated control site using a Nikon D300 camera and Micro Nikkor lens. Test and control sites are clearly labeled for each individual, and color standards are visible in each subject's photograph. Images are saved as raw data (NEF files) and also as JPEG files, arranged by subject. Photographs are analyzed for colorimetry using Image Pro Analysis software.

10.0 Adverse Events

10.1 Definition of an Adverse Event

An adverse event (AE) is any untoward medical occurrence in a clinical investigation where a subject is administered a pharmaceutical product/biologic (at any dose), OTC, cosmetic product or medical device and which does not necessarily require a causal relationship with a test article. An AE can therefore be any unfavorable and unintended sign (including an abnormal laboratory finding, for example), symptom or disease temporally associated with the use of a medicinal product whether or not considered related to the medicinal product.

10.2 Assessment of Severity and Relationship

The investigator or his/her medical staff evaluates all adverse events as to their severity and relation to the test article. The severity of adverse events is graded as follows:

| | |
|---|---|
| Mild | Awareness of a sign or symptom but easily tolerated |
| Moderate | Discomfort sufficient to cause interference with usual activity or to affect clinical status |
| Severe | Incapacitating with inability to do usual activity or to significantly affect clinical status |

The Investigator and/or trained staff member also assesses the relationship of any adverse event to the use of the study article, based upon available information, using the following guidelines:

| | | |
|---|---|---|
| 0 | Unlikely | No temporal association, or the cause of the event has been identified, or the test article cannot be implicated |
| 1 | Possible | Temporal association, but other etiologies are likely to be the cause; however, involvement of the test article cannot be excluded |
| 2 | Probable | Temporal association, other etiologies are possible, but not likely |
| 3 | Definite | Clear-cut temporal association |

10.3 Definition of a Serious Adverse Event (SAE)

A serious adverse event is any experience or reaction occurring at any dose that results in any of the following outcomes: death; is life threatening; inpatient hospitalization or prolongation of hospitalization; a persistent or significant disability/incapacity; or a congenital anomaly/birth defect.

Important medical events that may not result in death, be life-threatening, or require hospitalization may be considered a serious adverse event when, based upon appropriate medical judgment, they may jeopardize the patient or subject and may require medical or surgical intervention to prevent one of the outcomes listed in this definition. The term "life-threatening" refers to an event in which the subject was at risk of death at the time of event; it does not refer to an event that hypothetically might have caused death if it was more severe.

Hospitalization solely for the purpose of diagnostic tests, even if related to an adverse event, elective hospitalization for an intervention which was already planned before the inclusion of the subject in the study, and admission to a day-care facility may not themselves constitute sufficient grounds to be considered as a serious adverse event. Hospitalization is defined as being admitted to a hospital as an in-patient for greater than 24 hours.

10.4 Procedures for Reporting Adverse Events

At each visit, the subject is questioned about adverse events using an open question (e.g., "Have you noticed any change in your health since the last visit?").

Directed questioning and examination is performed when appropriate. All reported adverse events are documented on the appropriate forms without omitting any requested and known information.

Every time a concomitant therapy is reported during the study, an Adverse Event Form is completed if appropriate and the reason for the treatment noted.

When an adverse event persists at the end of the study, follow-up of the subject is conducted until the event is satisfactorily resolved.

10.5 Unanticipated Adverse Events

Unanticipated adverse effect is defined as any serious adverse effect on health or safety, any life-threatening problem or death caused by, or associated with, the test article if that effect, problem, or death was not previously identified in nature, severity, or degree of incidence in the application; or any other unanticipated serious problem associated with the test article that relates to the rights, safety, or welfare of subjects.

10.6 Anticipated Reactions

The test material when applied to the skin may produce mild irritation such as erythema, tanning, scaling/dryness, burning and/or stinging at the test site or surrounding the test sites. The responses discussed above will not be treated as adverse reactions. If sites begin to show mild levels of erythema, then product applications may be skipped as needed in order to avoid redness, which would interfere in the assessment of product efficacy. The UV exposure will create sunburn and possible discomfort. Hypo- or hyperpigmentation may occur at the skin sites, and the skin may show irritation where test material or vehicle is applied. These conditions may or may not resolve over time. Symptoms that are persistent and moderate to severe in nature, or that involve elevation (e.g., edema, papules, vesicles, spreading) will be considered adverse events (AEs).

11.0 Biostatistics and Data Management

Digital photographs will be taken of the entire treatment and control areas under standardized conditions. Images will be analyzed via a computer-aided colorimetry algorithm to determine L* values and b* values. The L* values of the treated areas and untreated areas from the images and Chromameter measurements will be compared to provide a "Skin Lightening Factor."

The "L* and b' colorimeter values are expected to be different between the test material-treated and untreated, irradiated area. Since each patient will serve as his own control, p-values will be determined by the two-tailed Student t-test.

Appendix 2

Exemplary Study Calendar

| SUNDAY | MONDAY | TUESDAY | WEDNESDAY | THURSDAY | FRIDAY | SATURDAY |
|---|---|---|---|---|---|---|
| 17 | 18<br>V1/D1<br>10:00-12:00<br>4:30-6:00<br>Paperwork<br>MED | 19<br>V2/D2<br>10:00-1:00<br>4:00-6:00<br>Irradiation | 20<br>D3<br>OFF | 21<br>D4<br>OFF | 22<br>D5<br>OFF | 23<br>D6<br>OFF |
| 24<br>D7<br>OFF | 25<br>V3/D8<br>11:00-1:00<br>4:30-6:00<br>Photos<br>Chromameter<br>Product App | 26<br>V4/D9<br>11:30-12:30<br>5:00-6:00<br>Product App | 27<br>V5/D10<br>11:30-12:30<br>5:00-6:00<br>Product App | 28<br>V6/D11<br>11:30-12:30<br>5:00-6:00<br>Product App | 29<br>V7/D12<br>11:00-1:00<br>4:30-6:00<br>Photos<br>Chromameter<br>Product App | 30<br>V8/D13<br>10:00-12:00<br>Product App |
| 1<br>D14<br>OFF | 2<br>V9/D15<br>11:30-12:30<br>5:00-6:00<br>Product App | 3<br>V10/D16<br>11:00-1:00<br>4:30-6:00<br>Photos<br>Chromameter<br>Product App | 4<br>V11/D17 11:30-12:30<br>5:00-6:00<br>Product App | 5<br>V12/D18 11:30-12:30<br>5:00-6:00<br>Product App | 6<br>V13/D19<br>11:00-1:00<br>4:30-6:00<br>Photos<br>Chromameter<br>Product App | 7<br>V14/D20<br>10:00-12:00<br>Product App |
| 8<br>D21<br>OFF | 9<br>V15/D22<br>11:00-1:00<br>4:30-6:00<br>Photos<br>Chromameter<br>Product App | 10<br>V16/D23<br>11:30-12:30<br>5:00-6:00<br>Product App | 11<br>V17/D24<br>11:30-12:30<br>5:00-6:00<br>Product App | 12<br>V18/D25<br>11:00-1:00<br>4:30-6:00<br>Photos<br>Chromameter<br>Product App | 13<br>V19/D26<br>11:30-12:30<br>5:00-6:00<br>Product App | 14<br>V20/D27<br>10:00-12:00<br>Product App |
| 15<br>D28 OFF | 16<br>V21/D29<br>11:00-1:00<br>4:30-6:00<br>Photos<br>Chromameter<br>Product App | 17<br>V22/D30<br>11:30-12:30<br>5:00-6:00<br>Product App | 18<br>V23/D31<br>11:30-12:30<br>5:00-6:00<br>Product App | 19<br>V24/D32<br>11:00-1:00 4:30-6:00<br>Photos<br>Chromameter<br>Product App | 20<br>V25/D33<br>11:30-12:30<br>5:00-6:00<br>Product App | 21<br>V26/D34<br>10:00-12:00<br>Product App |
| 22<br>D35<br>OFF | 23<br>V27/D36<br>11:00-1:00<br>4:30-6:00<br>Photos<br>Chromameter | 24 | 25 | 26 | 27 | 28 |

12.0 Results

Figure 6:
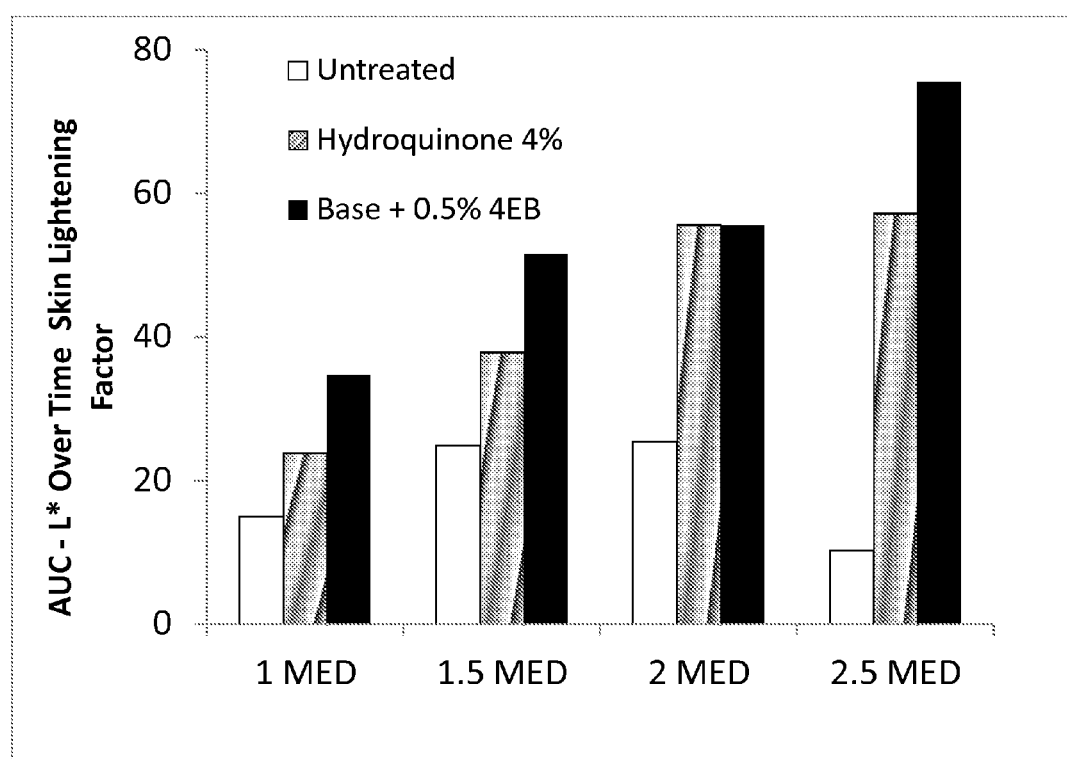
FIG. 6 is a graph depicting the increase in brightness of UV-induced pigmentation where human skin is left untreated, or is treated with 4% hydroquinone or Base+0.5% 4EB.

An increase in brightness of UV-induced pigmentation was observed in patient sites treated with Base+0.5% 4EB compared to 4% hydroquinone (See FIG. 6).

Example 15

MelanoDerm Model

The following example provides a validated model for melanin production using human skin equivalent.

Melanogenesis study: The melanoderm tissues (MEL-300B) were obtained from MatTek Corporation and cultured for 14 days at specified conditions. The tissues were treated with 15 µl of formulations or with 25 µl of positive (1% Kojic acid solution) and negative (DI water) controls every other day during this period. Tissues were taken out in between this period at specific days and fixed for histological imaging, light microscopy or for melanin quantification.

As seen in FIG. 6, Base+1% 4EB was more effective than Kojic Acid in reducing the melanin content of the skin equivalent.

While preferred embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments described herein may be employed in practicing the embodiments. It is intended that the following claims define the scope of the embodiments and that methods and structures within the scope of these claims and their equivalents be covered thereby.

What is claimed:

1. A method of treating hyperpigmentation or a hypermelanosis disorder in an individual, comprising administering to the individual in need thereof an effective amount of a composition comprising: from about 0.01% to about 2% substituted benzaldehyde, selected from the group consisting of 2-ethoxybenzaldehyde, 4-ethoxybenzaldehyde, 4-allyloxybenzaldehyde and 4-propoxybenzaldehyde, and a pharmaceutically or cosmetically acceptable carrier.

2. The method of claim 1, further comprising administering to the individual in need thereof an effective amount of from about 0.01% to about 5.0% of an additional agent, wherein the additional agent is selected from the group consisting of retinol, niacinamide, tetrahexyldecyl ascorbate, *glycyrrhiza glabra* (licorice) root extract, hexyl resorcinol, ethyl linoleate, or mixtures thereof.

3. The method claim 1, wherein the amount of substituted benzaldehyde in the composition is about 0.5%.

4. The method of claim 1, wherein the method reduces melanin distribution by about 10% to about 40%.

5. The method of claim 1, wherein the composition is topically or transdermally administered to the skin of the individual.

6. The method of claim 1, wherein the composition further comprises one or more additional active agents.

7. The method of claim 6, wherein the additional active agent is an antioxidant, a sunscreen, a sunprotectant, a sunblock, a skin-lightening agent, an anti-inflammatory agent, an anti-acne agent or mixtures thereof.

* * * * *